United States Patent [19]

Toyoda et al.

[11] Patent Number: 5,272,268
[45] Date of Patent: Dec. 21, 1993

[54] DIPEPTIDE DERIVATIVES

[75] Inventors: Tatsuo Toyoda, Kawanishi; Toshihiro Fujioka, Kitakatsuragi; Kunio Hayashi, Kadoma; Masuhisa Nakamura, Takarazuka; Naofumi Hashimoto, Daito, all of Japan

[73] Assignee: Shionogi & Co., Ltd., Osaka, Japan

[21] Appl. No.: 974,211

[22] Filed: Nov. 10, 1992

Related U.S. Application Data

[62] Division of Ser. No. 719,492, Jun. 24, 1991, Pat. No. 5,194,608.

[30] Foreign Application Priority Data

Jun. 28, 1990 [JP] Japan .................. 2-172050

[51] Int. Cl.$^5$ .................. C07D 401/06; C07D 413/06; C07D 277/18; C07D 249/14
[52] U.S. Cl. .................. 544/137; 544/238; 544/335; 544/406; 546/146; 546/168; 546/209; 546/275; 548/200; 548/214; 548/215; 548/253; 548/255; 548/266.8
[58] Field of Search ............... 544/137, 238, 406, 335; 546/146, 168, 209, 275; 548/200, 214, 215, 253, 255, 266.8

[56] References Cited

U.S. PATENT DOCUMENTS 4,791,102 12/1988 Bernat et al. .................. 544/168

Primary Examiner—Johann Richter
Attorney, Agent, or Firm—Wenderoth, Lind & Ponack

[57] ABSTRACT

A following dipeptide derivative of the following formula (I) is provided, which is capable of inhibiting the enzymatic activity of renin and thereby depressing the renin-angiotensin system and lowering the blood pressure.

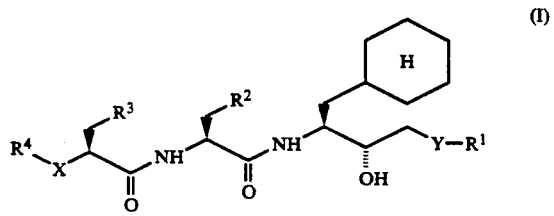

(I)

wherein:
$R^1$ is $C_1$–$C_{12}$ alkyl, $C_2$–$C_6$ alkenyl, $C_2$–$C_6$ alkynyl, $C_3$–$C_{10}$ cycloalkyl, aryl, or heterocyclic radical;
$R^2$ is carbamoyl, aryl, 5- or 6-membered heterocyclic radical, $C_1$–$C_{12}$ alkyl-S—, $C_1$–$C_{12}$ alkyl-S—$CH_2$—, or $C_3$–$C_{10}$ cycloalkyl-S—;
$R^3$ is aryl or 5- or 6-membered heterocyclic radical;
$R^4$ is $R^{4'}$—$SO_2$ or $R^{4'}$—CO;
$R^{4'}$ is aryl, $C_1$–$C_{12}$ alkyl, $C_2$–$C_6$ alkenyl, $C_2$–$C_6$ alkynyl; $C_3$–$C_{10}$ cycloaklyl, or heterocyclic radical;
X is $CH_2$, NH, O, or S; and
Y is CO or $NHSO_2$, wherein $R^1$, $R^2$, $R^3$ and $R^{4'}$ each may be substituted with one to three substituents.

1 Claim, No Drawings

DIPEPTIDE DERIVATIVES

This is a divisional application of Ser. No. 07/719,492, filed on Jun. 24, 1991 now U.S. Pat. No. 5,194,608.

FIELD OF THE INVENTION

This invention relates to dipeptide derivatives capable of inhibiting the renin activity.

PRIOR ART

The renin (EC3.4.23.15) is a protease which catalyzes the hydrolysis of angiotensinogen into angiotensin I. The angiotensin I is a biologically inactive decapeptide, though it is enzymatically converted into angiotensin II by an angiotensin converting enzyme in pulmonal vascular endotheliocytes. This system is "the renin-angiotensin system". The angiotensin II induces hypertension through at least two routes, that is, contractive action on smooth muscles of peripheral vasculars and stimulation of secretion of adrenal hormone which inhibits sodium ion excretion. More particularly, it stimulates the secretion of aldosterone, an inhibitor of the excretion of $Na^+$ ion, resulting in an increase of the volume of extracellular body fluid, which is one of causes hypertension. Accordingly, compounds capable of depressing or inhibiting the renin-angiotensin system are expected to be potent anti-hypertensive substance. Many peptide analogues which seemed to be useful in the regulation of hypertensive diseases on the basis of renin-inhibiting activity have been developed and disclosed [for example, U.S. Pat. No. 4,656,269, EP-A-274259 and AU-A-8822959].

As mentioned above, the renin inhibitor inhibits the synthesis of Angiotensin I and thereby depressing the renin-angiotensin system and lowering the blood pressure. Owing to the physiological activity, renin inhibitors have been used in the treatment of hypertension. However, since the hypertension is one of the most popular disorders and causes many serious conditions and diseases, a development of more and more novel anti-hypertensive substances including renin inhibitors has been demanded to treat hypertension effectively.

SUMMARY OF THE INVENTION

The present inventors have now discovered a class of novel dipeptide compounds capable of inhibiting the catalytic activity of renin both in vitro and in vivo.

DETAILED DESCRIPTION

In particular, the present invention provides a dipeptide derivative of formula (I):

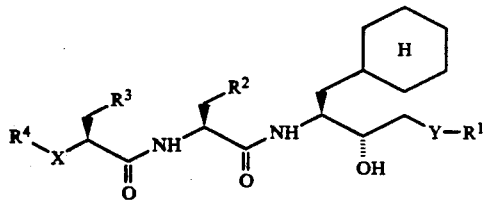

wherein:

$R^1$ is $C_1-C_{12}$ alkyl, $C_2-C_6$ alkenyl, $C_2-C_6$ alkynyl, $C_3-C_{10}$ cycloalkyl, aryl, or heterocyclic radical;

$R^2$ is carbamoyl, aryl, 5- or 6-membered heterocyclic radical, $C_1-C_{12}$ alkyl-S—, $C_1-C_{12}$ alkyl-S—$CH_2$—, or $C_3-C_{10}$ cycloalkyl-S—;

$R^3$ is aryl or 5- or 6-membered heterocyclic radical;

$R^4$ is $R^{4'}$—$SO_2$ or $R^{4'}$—CO;

$R^{4'}$ is aryl, $C_1-C_{12}$ alkyl, $C_2-C_6$ alkenyl, $C_2-C_6$ alkynyl; $C_3-C_{10}$ cycloakIyl, or heterocyclic radical;

X is $CH_2$, NH, O, or S; and

Y is CO or $NHSO_2$, wherein $R^1$, $R^2$, $R^3$ and $R^{4'}$ each may be substituted with one to three substituents selected independently from a group consisting of hydroxy; halogen; trifluoromethyl; —CN; heterocyclic radical; $C_1-C_6$ alkyl; $C_3-C_{10}$ cycloalkyl; —O—$C_1-C_6$ alkyl; —S—$C_1-C_6$ alkyl; —SO—$C_1-C_6$ alkyl; —$SO_2$—$C_1-C_6$ alkyl; $C_1-C_6$ alkylenedioxy; —CO—O—$C_1-C_6$ alkyl; —NHCO—$C_1-C_6$ alkyl; —$NHSO_2$—$C_1-C_6$ alkyl; —$NR^5R^6$; —O—CO—$NR^5R^6$; —CO—$NR^5R^6$; —O—$C_1-C_6$ alkyl $NR^5R^6$; $R^5$ and $R^6$ are independently hydrogen, formyl or $C_1-C_6$ alkyl, or $R^5$ and $R^6$, when taken together with the nitrogen to which they are attached, form a cyclic amino group, or an acid addition salt thereof.

As an another aspect of the present invention, it also provides a compound of formula (II):

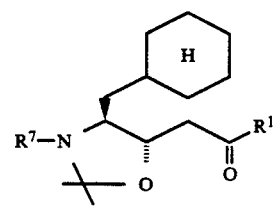

wherein, $R^1$ is as defined above, and $R^7$ is hydrogen or an amino protecting group, which compound is useful as an intermediate for the production of the compound of formula (I).

For the purpose of the present invention, as disclosed and claimed herein, the following terms are defined as below.

The term "$C_1-C_{12}$ alkyl" refers to a straight or branched saturated hydrocarbon radical having one to twelve carbon atoms, including methyl, ethyl, n-propyl, isopropyl, n-butyl, isobutyl, s-butyl, t-butyl, n-pentyl, isopentyl, 2-methylbutyl, t-pentyl, neopentyl, isopentyl, 1-ethylpropyl, n-hexyl, isohexyl, heptyl, octyl, nonyl, decyl, undecyl, dodecyl, and the like.

The term "$C_1-C_6$ alkyl" refers to a straight or branched saturated hydrocarbon radical having one to six carbon atoms as defined above.

The term "$C_2-C_6$ alkenyl" refers to a straight or branched unsaturated hydrocarbon radical having two to six carbon atoms and one or more double bonds, including vinyl, allyl, 1-propenyl, isopropenyl, 2-butenyl, 1,3-butadienyl, 2-pentenyl, 1-hexenyl, and the like.

The term "$C_2-C_6$ alkynyl" refers to a straight or branched unsaturated hydrocarbon radical having two to six carbon atoms and one or more triple bonds, including ethynyl, 1-propynyl, 2-propynyl, 2-butynyl, 1,3-butadiynyl, 2-pentynyl, 1-hexynyl, and the like.

The term "$C_1-C_6$ alkylenedioxy" refers to methylenedioxy, ethylenedioxy, triethylenedioxy, tetramethylenedioxy, pentamethylenedioxy, hexamethylenedioxy, and the like.

The term "C$_3$-C$_{10}$ cycloalkyl" refers to cyclopropyl, cyclobutyl, cyclopentyl, cyclohexyl, cycloheptyl, cyclooctyl, cyclononyl, cyclodecyl, and the like.

The term "aryl" refers to aryl radicals having 6 to 10 carbon atoms, including phenyl, indenyl, naphthyl and the like.

The term "halogen" refers to halogen atoms such as fluorine, chlorine, bromine, and iodine.

The term "cyclic amino" refers to monocyclic or bicyclic amino groups such as pyrrolidino, 2-pyrazolidinyl, piperidino, 1-piperazinyl, 1-indolinyl, 2-indolinyl, morpholino, and the like.

The term "heterocyclic group" refers to a group of saturated or unsaturated monocyclic or condensed ring which contains one or more heteroatoms selected from nitrogen, oxygen and sulfur. Examples of heterocyclic groups include, for example, 2-thienyl, 3-thienyl, 2-furyl, 3-furyl, 2-pyrrolyl, 3-pyrrolyl, 2-imidazolyl, 1-pyrazolyl, 2-pyridyl, 3-pyridyl, 4-pyridyl, 2-pyrimidyl, 3-pyridazinyl, 2-pyrazinyl, 3-triazolyl, 2-thiazolyl, 4-thiazolyl, 5-tetrazolyl, 3-isothiazolyl, 2-pyrrolidinyl, 2-imidazolidinyl, 4-pyrazolidinyl, 4-piperidyl, 2-piperadinyl, 4-indolyl, 7-indolyl, 5-quinolyl, 8-quinolyl, 8-isoquinolyl, morpholine and the like.

The term "5- or 6-membered heterocyclic groups" refers to 5- or 6-membered heterocyclic groups as defined above.

The term "carbamoyl" refers to carbamoyl or carbamoyl substituted with one or two substituents selected from a group consisting of C$_1$-C$_6$ alkyl or C$_3$-C$_{10}$ cycloalkyl, for example, carbamoyl, methylcarbamoyl, dimethylcarbamoyl, cyclohexylcarbamoyl, and the like.

In the definition of R$^1$, preferred "C$_1$-C$_{12}$ alkyl" is methyl, ethyl, propyl, isopropyl, t-butyl, pentyl, hexyl, heptyl, or the like; preferred "C$_1$-C$_6$ alkyl" is methyl, ethyl, propyl, isopropyl, t-butyl, or the like; preferred "C$_2$-C$_6$ alkenyl" is vinyl, or the like; preferred "C$_2$-C$_6$ alkynyl" is ethynyl, or the like; preferred "C$_3$-C$_{10}$ cycloalkyl" is cyclopropyl, cyclobutyl, cyclopentyl, cyclohexyl, or the like; preferred "aryl" is phenyl, naphtyl, or the like. Preferred "heterocyclic group" is 5-or 6-membered heterocyclic group such as 2-thienyl, 2-furyl, 2-pyrrolyl, 2-thiazolyl, 4-thiazolyl, 5-tetrazolyl, 4-pyridyl, 5-pyrimidinyl, 2-pyrazinyl, 2-pyrroldinyl, 4-piperidyl, or the like or condensed heterocyclic group such as 8-quinolyl, or the like.

Examples of preferable R$^1$ include phenyl, o-tolyl, p-tolyl, m-tolyl, 2-chlorophenyl, 3-chlorophenyl, 4-chlorophenyl, 2,4-dichlorophenyl, 2,6-dichlorophenyl, 2-bromophenyl, 3-bromophenyl, 4-bromophenyl, 2,4-dibromophenyl, 2,6-dibromophenyl, 2-fluorophenyl, 3-fluorophenyl, 4-fluorophenyl, 2,4-difluorophenyl, 2,6-difluorophenyl, 2-tolufluoromethyl, 3-tolufluoromethyl, 4-tolufluoromethyl, 2-hydroxyphenyl, 3-hydroxyphenyl, 4-hydroxyphenyl, 2-methoxyphenyl, 3-methoxyphenyl, 4-methoxyphenyl, 3,4-dimethoxyphenyl, 3,4-methylenedioxyphenyl, 3-methylaminophenyl, 3-(N-formyl)methylaminophenyl, 2-dimethylaminophenyl, 3-dimethylaminophenyl, 4-dimethylaminophenyl, 2-morpholinophenyl, 3-morpholinophenyl, 4-morpholinophenyl, 2-(4-methylpiperazyno)phenyl, 3-(4-methylpiperazyno)phenyl, 4-(4-methylpiperazyno)phenyl, 2-acetamidophenyl, 3-acetamidophenyl, 4-acetamidophenyl, 2-methylsulfonylaminophenyl, 3-methylsulfonylaminophenyl, 2-methylsulfonylaminophenyl, 2-isopropoxycarbonylphenyl, 3-isopropoxycarbonylphenyl, 4-isopropoxycarbonylphenyl, 2-morpholinocarbonylphenyl, 3-morpholinocarbonylphenyl, 4-morpholinocarbonylphenyl, 2-morpholinocarbonyloxyphenyl, 3-morpholinocarbonyloxyphenyl, 4-morpholinocarbonyloxyphenyl, 2-morpholinoethoxyphenyl, 3-morpholinoethoxyphenyl, 4-morpholinoethoxyphenyl, 2-cyanophenyl, 3-cyanophenyl, 4-cyanophenyl, naphtyl, 2-pyrrolyl, 3-pyrrolyl, 1-methyl-2-pyrrolyl, 5-tetrazolyl, 1-methyl-5-tetrazolyl, 2-furyl, 3-furyl, 2-thienyl, 3-thienyl, 2-pyridyl, 3-pyridyl, 4-pyridyl, 1-methyl-4-pyridyl, 2-methyl-4-pyridyl, 3-methyl-4-pyridyl, 1-chloro-4-pyridyl, 2-chloro-4-pyridyl, 3-chloro-4-pyridyl, 1-fluoro-4-pyridyl, 2-fluoro-4-pyridyl, 3-fluoro-4-pyridyl, 2-pyrimidinyl, 5-pyrimidinyl, 2-pyrazinyl, 2-pyrrolidinyl, 3-pyrrolidinyl, 1-methyl-2-pyrrolidinyl, 1-methyl-3-pyrrolidinyl, 2-piperidyl, 3-piperidyl, 4-piperidyl, 1-methyl-2-piperidyl, 1-methyl-3-piperidyl, 1-methyl-4-piperidyl, 8-quinolyl, methyl, ethyl, isopropyl, butyl, isobutyl, tert-butyl, pentyl, hexyl, heptyl, octyl, dimethylaminomethyl, morpholinomethyl, 1-morpholinoisopropyl, 1-morpholinoethoxyisopropyl, 1-piperidinomethyl, cyclopropyl, cyclopentene, cyclohexyl, cycloheptyl, cyclooctyl, 2-morpholinocyclohexyl, 3-morpholinocyclohexyl, 4-morpholinocyclohexyl, 2-methylaminocyclohexyl, 3-methylaminocyclohexyl, 4-methylaminocyclohexyl, 2-dimethylaminocyclohexyl, 3-dimethylaminocyclohexyl, 4-dimethylaminocyclohexyl, and the like.

Examples of preferable R$^2$ include 5-membered heterocyclic group containing two heteroatoms such as two nitrogen atoms, nitrogen and oxygen atoms, or nitrogen and sulfur atoms, for example, 4-imidazolyl, 4-thiazolyl, 4-oxazolyl, or the like, wherein said heterocyclic group may be substituted with methyl, ethyl, isopropyl, tert-butyl, amine, methylamine, dimethylamine, diethylamine, 1-pyrrolidinyl, piperidino, or the like; C1–C12 alkyl-S— such as methylthio, ethylthio, cyclohexylthio, or the like; C1–C12 alkyl-S—CH$_2$13 such as methylthiomethyl, or the like; carbamoyl or substituted carbamoyl such as methylcarbamoyl, dimethylcarbamoyl, or the like.

Examples of preferable R$^4$ include sulfonyl or carbonyl substituted with methyl, ethyl, isopropyl, dimethylamino, tert-butyl, N-morpholino or N-morpholinomethyl, or the like.

Examples of more preferable R$^1$ are shown below.

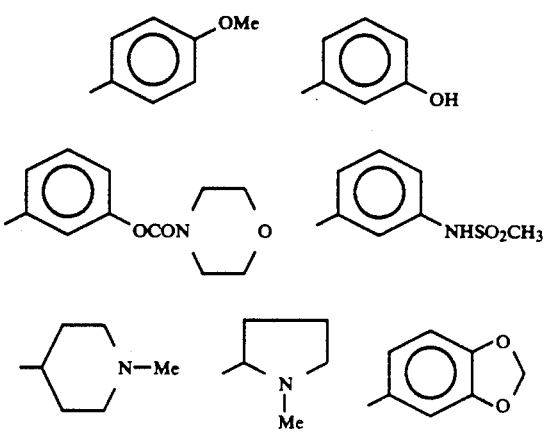

-continued

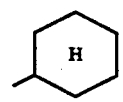 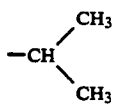 

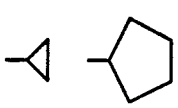 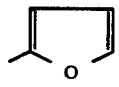 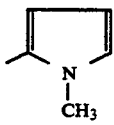

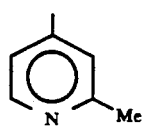 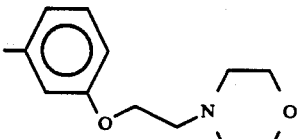

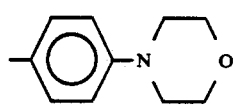 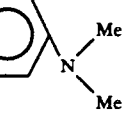

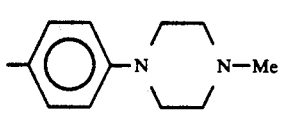 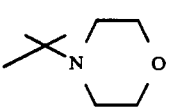

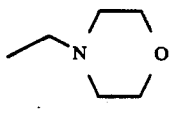 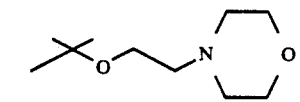

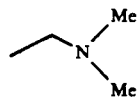 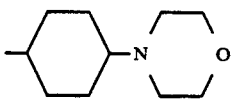

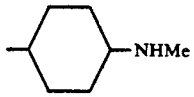 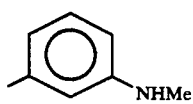

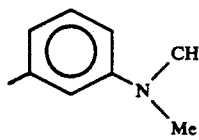 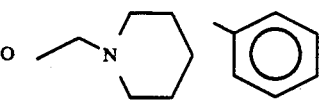

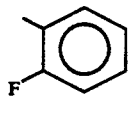 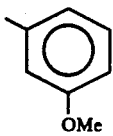 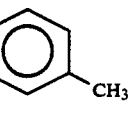

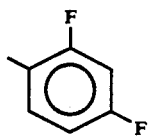 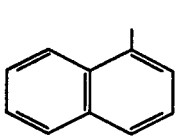 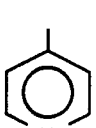

-continued

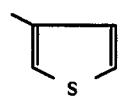  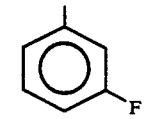 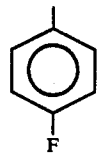

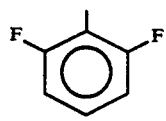 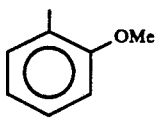 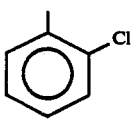

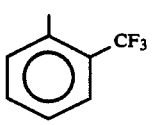 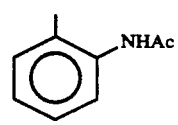 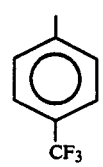

 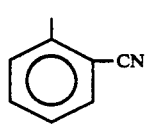

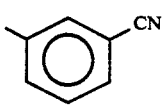 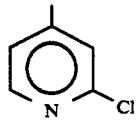 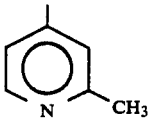

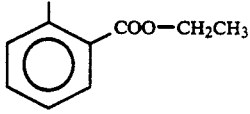 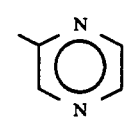

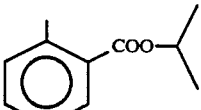 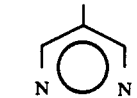 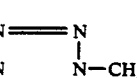

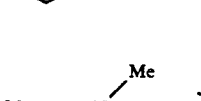 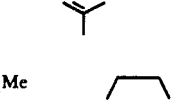

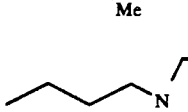 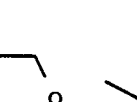 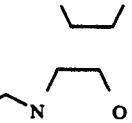

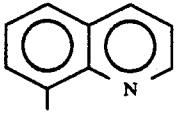 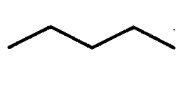

Especially preferred compounds are those wherein $R^2$ is an optionally substituted 5- or 6-membered heterocyclic group; $R^3$ is an optionally substituted aryl; $R^4$ is morpholinosulfonyl; and X is NH.

The pharmaceutically acceptable acid addition salts of compounds of formula (I) include salts derived from a mineral acid such as hydrochloric acid, sulfuric acid, p-toluenesulfonic acid, or the like; carboxylic acid such as oxalic acid, maleic acid, citric acid, or the like. Preferable acid addition salts are those derived from mineral acids such as hydrochloric acid, sulfuric acid, toluenesulfonic acid, and the like.

All the compounds of the present invention are novel and can be prepared according to either of two processes described below on the basis of what Y represents.

PROCESS I

Preparation of compounds wherein Y is CO

The process is schematically shown as below.

Step 1

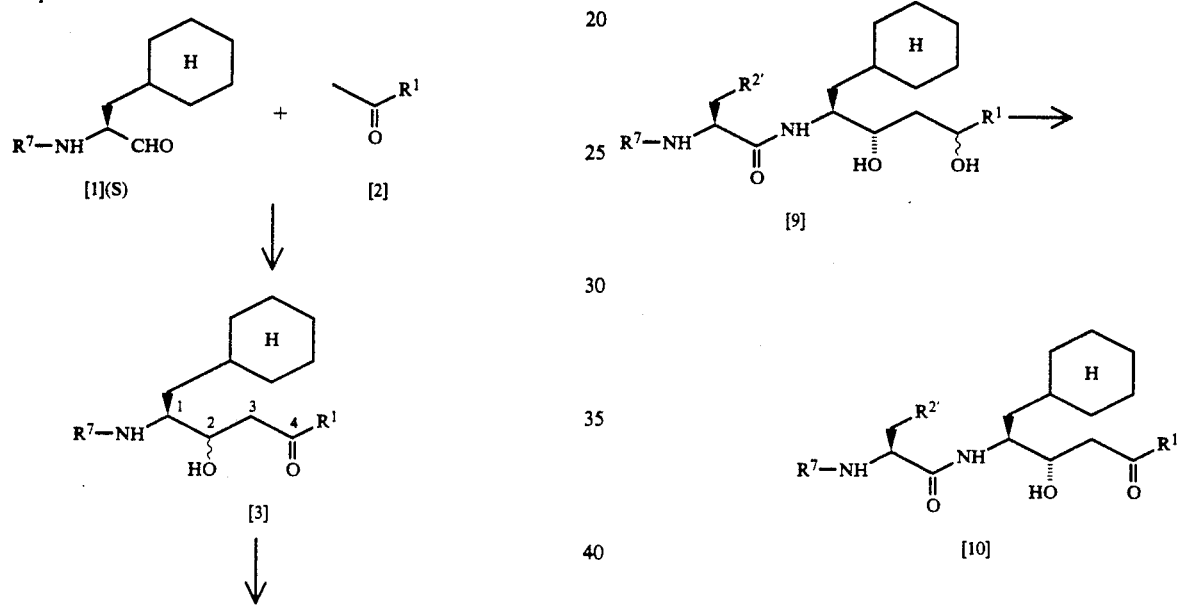

Step 2a

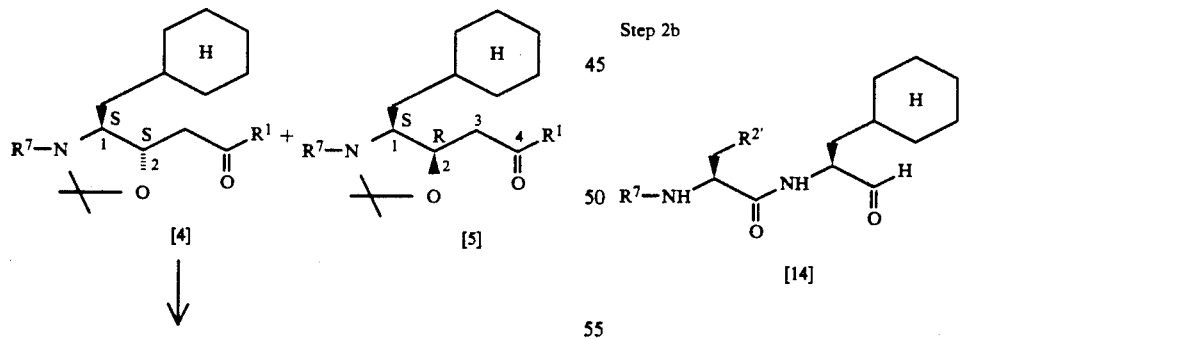

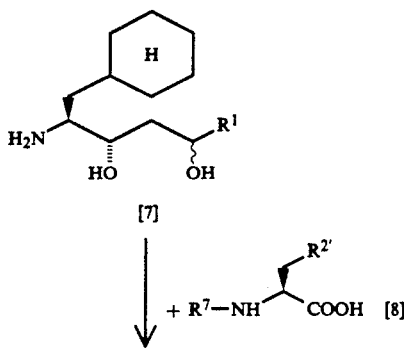

[7]

+ $R^7$—NH—CH($R^{2'}$)—COOH  [8]

[9]

[10]

Step 2b

[14]

Step 2c

[19]

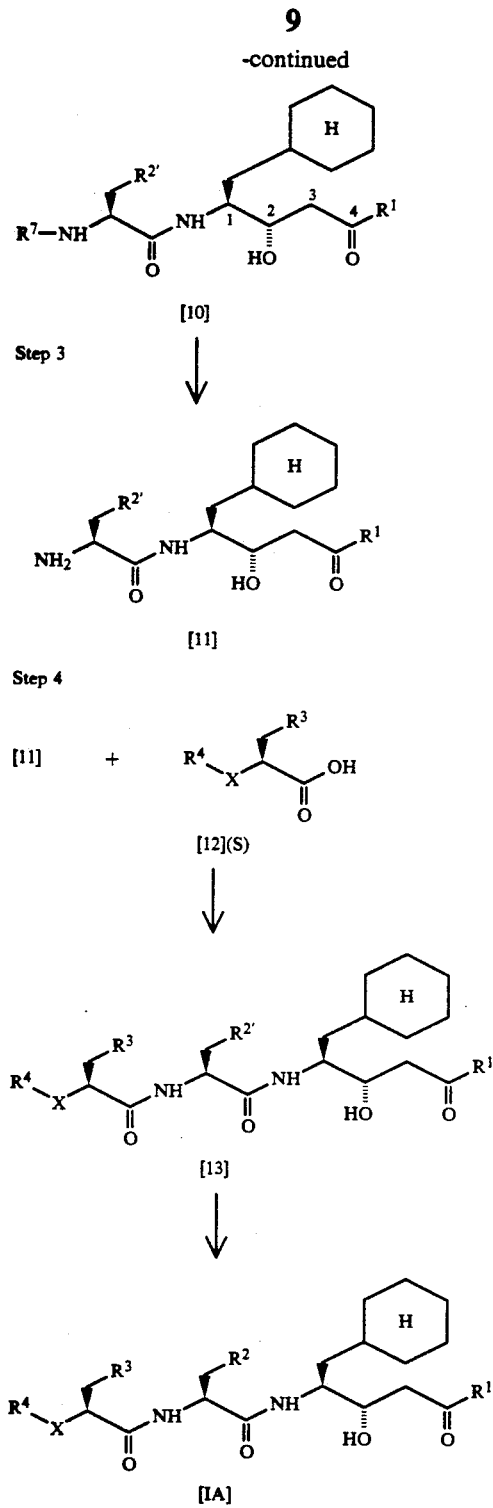

In the above reaction schemes, $R^1$, $R^2$ and $R^3$ are as defined above, $R^{2'}$ is optionally protected $R^2$ and $R^7$ is amino-protecting group.

The amino protecting group which is shown by $R^7$ can be selected from those groups generally used in the peptide synthesis. Examples of amino protecting groups include benzyloxycarbonyl (it is referred to as Z), 2,6-dichlorobenzyloxycarbonyl (Z(Cl)$_2$), 4-nitrobenzyloxycarbonyl ((Z(NO$_2$)), 4-methoxybenzyloxycarbonyl (Z(OMe)), t-butoxycarbonyl (Boc), t-amyloxycarbonyl (Aoc), isobornyloxycarbonyl, adamantyloxycarbonyl (Adoc), 2-(4-biphenyl)-2-propyloxycarbonyl (Bpoc), 9-fluorenylmethoxycarbonyl (Fmoc), methylsulfonylethoxycarbonyl (Msc), trifluoroacetyl, phtalyl, formyl, 2-nitrophenylsulfenyl (NPS), diphenylphosphinothioyl (Ppt), dimethylphosphinothioyl (Mpt), and the like.

Examples of the optionally protected $R^2$ shown by $R^{2'}$ are 4-imidazoyl, 4-aminothiazolyl and $R^2$ as defined above, which are optionally protected with a group selected from benzyl (Bzl), benzyloxycarbonyl (Z), toluenesulfonyl (tosyl or Ts), trimethylsilyl (trityl, Trt), dinitrophenyl (Dnp), 2,2,2-trifluoro-1-benzyloxycarbonylaminoethyl (Tfz), 2,2,2-trifluoro-1-t-butoxycarbonyl (TfBoc), adamantyloxycarbonyl (Adoc), piperidinocarbonyl, t-butoxycarbonyl(Boc), and the like.

STEP 1

1. Preparation of Compound [3] by Aldol Reaction a) The optically active aldehyde [1], a required starting compound, can be prepared from, for example, Boc-L-phenylalanine using any of known methods described in literatures such as [1](T. Shioiri et al., *J. Org. Chem.* 52:1252 (1987) and J. Boger et al., *J. Med. Chem.* 28:1779 (1985)).

The aldol condensation between an aldehyde [1] and a ketone [2] is carried out by a novel stereoselective method of the present invention. The reaction is conducted using metal amide, as a base, in an organic solvent in the presence of a crown ether at a temperature of about $-78°$ C. Amides which may be used include sodium bis-trimethylsilylamide (NaN(TMS)$_2$), potassium bis-trimethylsilylamide (KN(TMS)$_2$), lithium diisopropylamide, lithium bis-trimethylsilylamide, and the like. Crown ethers which may be used include 15-crown-5, 12-crown-4, 18-crown-6, and the like. Although all the combinations of amides and crown ethers described above are suited for the stereoselective aldol reaction of the invention, a certain combinations are especially preferable in connection with the stereoselectivity of the product [3] which is expressed by the ratio of the product of 2S form to 2R form, i.e., diastereoselectivity, 2S:2R. Thus, NaN(TMS)$_2$, when used in association with 15-crown-5, gives the most favorable result shown by the 2S:2R value of about 2.4 to about 16.0, while other amides, when used alone or in combination with a crown ether, give inferior results shown by the 2S:2R value of less than 2.

Solvents which may be used include ethers such as diethyl ether, tetrahydrofuran (THF), dimethoxyethane, and the like with a preference for THF. When toluene is used, the stereoselectivity may be relatively decreased.

The reaction is carried out at a temperature ranging from about $-20°$ to about $-100°$ C., preferably about $-78°$ C.

b) Alternatively, the stereoselective aldol condensation reaction can be carried out using metal alkoxide as a base in an inert solvent in the presence of a quarternary ammonium salt at a temperature of about $-78°$ C.

Metal alkoxide which may be used include potassium t-butoxide (t-BuOK), potassium t-amyloxide (Et(Me)$_2$COK) or sodium ethoxide (EtONa), and the like.

Quarternary ammonium salts which may be used include tetrabutyl ammonium bromide ((n-Bu)$_4$NBr), tetramethyl ammonium bromide ((Me)$_4$NBr), tributylbenzylammonium bromide((Bn(n-Bu)$_3$NBr), and the like. All the reagents are suited to the stereoselective aldol reaction of the invention and the best result can be obtained by the combination of t-BuOK and n-Bu$_4$NBr giving the 3S/3R value of about 3.3-6.5. This method is useful even in the absence of quarternary ammonium salt and gives the ratio of 3S/3R of about 3 to 5.

Solvents which may be used include THF, toluene, dichloroethane, dichloromethane, and the like with a preference for dichloromethane. When THF or toluene is used, the stereoselectivity may be decreased. The reaction can be conducted under a similar temperature as described in above a).

2) Separation of Stereoisomer (1S, 2S) [4]

The desired stereoisomer [3]-(2S) can be separated from a mixture of isomers shown by formula [3] by a known resolving procedure, for example, a column chromatography on silica gel. For the purpose of the invention, the desired isomer can be conveniently separated by reacting the mixture [3] with 2-methoxypropene or 2,2-dimethoxypropane in the presence of a catalytic amounts of p-toluene sulfonic acid or pyridinium p-toluene sulfonate in a solvent such as THF or dichloroethane at a temperature ranging from room temperature to the refluxing temperature for about 1 to 8 hours to obtain a product containing a mixture of ring-closed compounds [4] and [5] which differ in the crystallizing properties from a certain solvents. Thus, when the product is recrystallized from ethyl acetate or diisopropyl ether in which the desired stereoisomer [4] is hardly soluble and the undesired isomer [5]-(2R) is soluble, the former can be separated as a crystalline solid, while the latter remains in the mother liquor. A column chromatography on, for example, silica gel, can be used when the compound [4] is not separated by recrystallization in ease. The so obtained compound [4] in (1S, 2S) form is a novel and useful compound as an intermediate for the production of the compound (I).

Alternatively, the product [3], without further treatment to form acetonide, can be directly subjected to a column chromatography on silica gel to yield the stereoisomer [3]-(2S), which is then converted into dihydric alcohol of formula [7].

STEP 2a

Before the deprotection of C1 amino group, the compound [4] should be reduced to avoid the possibility of ring closing reaction between the deprotected amino group and the C4 carbonyl group. The reducing reaction can be carried out using any of known methods in the art. However, it is efficiently conducted by reacting a solution of the ketone [4] in ethanol, methanol, THF or toluene with a reducing reagent such as sodium borohydrate, L-selectride or Red-Al at room temperature or under cooling for about 0.5 to 2 hours. Preferably, the latter reagent is used slightly in excess, that is, about 1.0 to 1.3 mole to 1.0 mole of ketone [4]. The resultant product [6], a mixture of diastereoisomers (1:1 to 3:1), is used in the next deprotection step without further purification.

The deprotection of amino group can be carried out using any of following procedures. When the protecting group is Boc, and the like, the compound [6] is deprotected by dissolving into THF or dioxane, adding 6N HCl thereto, and stirring at room temperature for about 1 to 4 hours. Alternatively, the compound [6] is treated with an acid such as aluminium chloride, trifluoroacetic acid or formic acid in the presence of anisole to yield the dihydric aminoalcohol [7].

When the protecting group is a member of benzyloxycarbonyl groups such as benzyloxycarbonyl (hereinafter, it is referred to as Z), 2,6-dichlorobenzyloxycarbonyl (Z(Cl)$_2$), or 4-nitrobenzyloxycarbonyl ((Z(NO$_2$)), the deprotection can be effected by catalytic reduction using palladium-containing catalyst, and the like. When the protecting group is Fmoc (9-fluorenylmethoxycarbonyl), Msc (methylsulfonylethoxycarbonyl), or the like, the deprotection can be effected by treating the compound [6] by piperidine, diethylamine, or the like.

The resulting dihydric alcohol of formula [7] is subjected to the next condensation reaction without purification. The condensation can be carried out using any procedure generally used in the field of peptide synthesis. For example, to a solution of compound [7] in an appropriate solvent such as dichloromethane is added commercially available N-Boc-amino acid [8] or its DCHA salt, and the mixture is allowed to react at room temperature for about 1 to 4 hours in the presence of a slightly in excess of a coupling reagent such as 1.0 to 1.3 mole equivalent of diethyl cyanophosphphate (DEPC) and, if desired, a tertiary amine such as N-methyl morpholine to obtain a coupled compound [9]. Examples of coupling reagents are DCC, EDC, DEPA, BOP, DCC-HOBt, DCC-HOSu, ethyl chlorocarbonate, isobutyl chlorocarbonate, isopropyl chlorocarbonate, diethyl chlorophosphate, diphenyl chlorophosphate, 2-chloro-4,6-dimethoxy-1,3,5-triazine, and the like. The compound [8] may be protected at the heterocyclic ring with a protecting group generally used in the field of peptide synthesis.

The resultant diastereisomer [9] is also converted into the corresponding ketone [10] without separation by dissolving the compound [9] into dichloromethane or DMF, adding about 3 to 10 times amounts of active manganese dioxide to the mixture and reacting at room temperature for 2 to 8 hours. This reaction proceeds very smoothly when fine crystal starting material [9] is used. The characteristic of this reaction is that the hydroxyl group at the C4 position of benzyl compound can be selectively oxidized.

STEP 2b

Compound [10] can be also prepared through an aldol reaction according to a procedure described in step 1 from a starting compound [2] and a dipeptide aldehyde of formula [14] obtainable from a corresponding dipeptide alcohol in the same manner as that used for the preparation of compound [1]. The reaction however proceeds without stereoselectivity and differs from that of step 1 in this regard. The product being a 1:1 mixture of compound [10] in 2S and 2R isomers, chromatographic procedure is required for the separation of desired [10]-(2S)-isomer. The characteristic of the method of step 2b is that it is applicable when the method of above step 2a is not effective because a compound resists the selective oxidization with manganese dioxide.

STEP 2c

The compound [10] can be prepared by reacting a chloromethyl ketone of formula [19] with an amine. The characteristic of the method of step 2c is that it is useful in the introduction of N-substituted methylketone residue to the C-terminal moiety.

STEP 3

The deprotection of ketone compound [10] can be carried out in the same manner as described in the preparation of amino dihydric alcohol [7] from compound [6]. For example, when the protecting group is Boc, it is carried out by adding excess aluminium chloride to an anisole solution of compound [10] and stirring the mixture for about 1 to 3 hours at a temperature ranging from ice-cooled temperature to room temperature. The deprotection can also be effected by treating the compound [10] with either of excess trifluoroacetic acid in anisole or 6N HCl in THF to yield the desired compound [11]. The resultant ketone [11] with carbonyl group at the C4 position is novel and important as an intermediate for preparing the compound of formula (I) of the present invention.

STEP 4

The compound [11] is reacted with sulfonyl propionic acid derivatives, N-sulfamyl, N-carbamoyl, or N-acyl amino acid of formula [12] which can be prepared according to a known method such as described in a literature (J. L. Stanton et al., *J. Med. Chem.* 31:1839 (1988)) under a condition for the coupling reaction and then deprotected if necessary to give the desired compound (IA) as the final product.

The coupling reaction is preferably conducted using 1.0 to 1.3 mole equivalent of diethyl cyanophosphonate (DEPC) in the presence of N-methyl morpholine (NMM) in a solvent such as dichloromethane at room temperature for about 1 to 8 hours. Examples of coupling reagents are DCC, EDC, DEPA, BOP, DCC-HOBt, ethyl chlorocarbonate, isobutyl chlorocarbonate, isopropyl chlorocarbonate, diethyl chlorophosphate, diphenyl chlorophosphate, 2-chloro-4,6-dimethoxy-1,3,5-triazine, and the like.

The deprotection of the compound [13] is carried out using any of known procedures depending on the protecting group. When the protecting group of $R^{2'}$ is tosyl, it can be carried out by stirring a mixture of a solution of compound [13] in DMF in the presence of 5 to 12 mole equivalent of pyridinium hydrochloride at room temperature for about 1 to 4 hours. The depotection can be effected by means of trifluoroacetic acid (at 15° C. for about 30 minutes), HBr/acetic acid (at room temperature for about 30 minutes), conc.ammonia (at room temperature for about 1 hour), conc.HCl, or the like.

PROCESS II

Preparation of compounds (I) wherein Y is NHSO2

The process is schematically shown as below.

Step 1

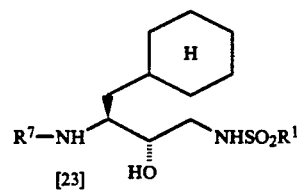

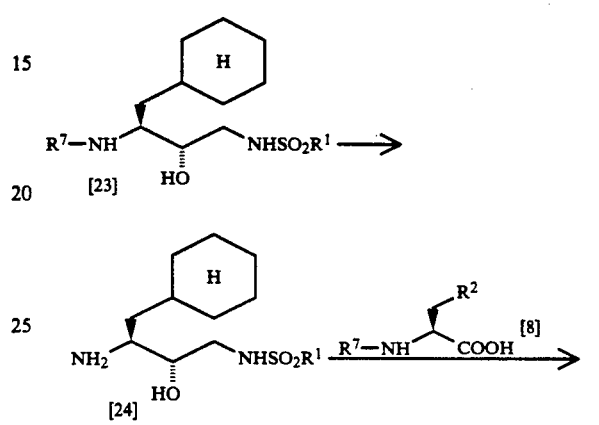

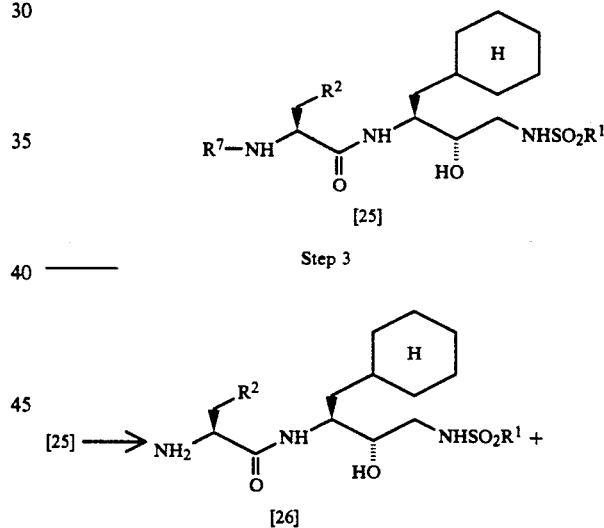

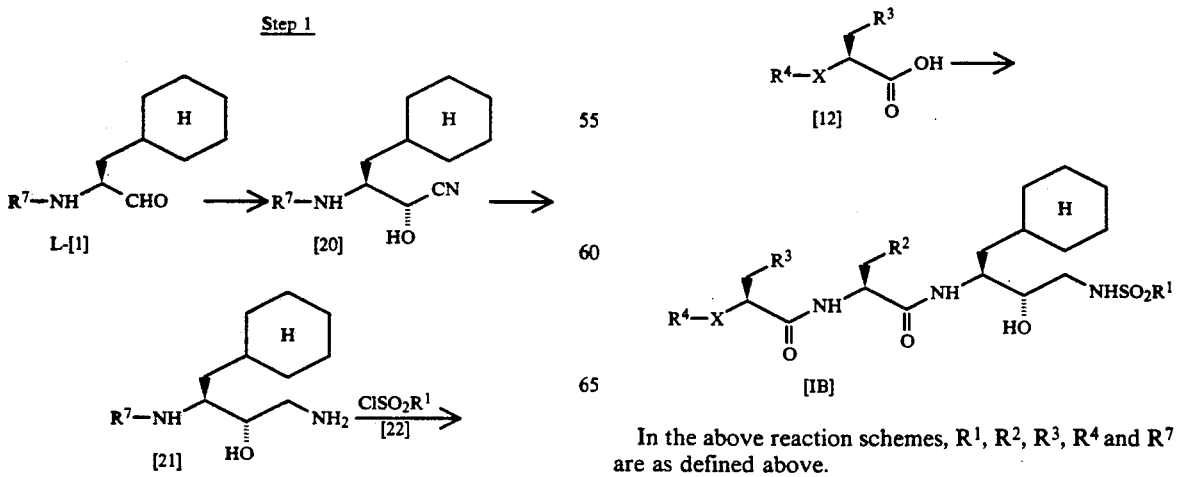

In the above reaction schemes, $R^1$, $R^2$, $R^3$, $R^4$ and $R^7$ are as defined above.

STEP 1

The optically active aldehyde [1], a required starting compound, can be prepared in the same manner as described in above Process I.

The preparation of cyanhydrin [20] from aldehyde [1] is carried out substantial in accordance with a procedure described in literatures. Thus, the aldehyde [1] is allowed to react with an acidic sodium sulfite to obtain an additive, which is then reacted with KCN in ethyl acetate at room temperature to yield the cyanhydrin [20] stereoselectively (2R/2S=3/1). The product is then resolved into each stereoisomer by a column chromatography on silica gel. The desired (2R)-isomer is a crystalline solid and can be purified by recrystallization while the undesired (2R)-isomer is an oil. Therefore, alternatively, the desired product [20]-2R can be obtained conveniently by adding a seed crystal to the reaction mixture, collecting the precipitate, and recrystallizing from a solvent before subjecting to the chromatography.

The cyanhydrin [20] is then converted into an amino alcohol [21] by reducing the nitrile group. The reduction is carried out effectively by dissolving cyanhydrin [20] into an ethereal solvent, preferably THF, adding about 2 to 2.5 mole of lithium aluminium hydride thereto. The resulting amino alcohol [21] is then, without purification, reacted with sulfonyl chloride [22] to obtain sulfonyl amide of formula [23]. The reaction is conducted by reacting the amino alcohol [21] and sulfonyl chloride [22] in an appropriate solvent such as dichloromethane in the presence of tertiary amine such as triethylamine at room temperature for overnight.

STEP 2

The deprotection of compound [23] can be carried out in a similar manner as described in the above Process I. The deprotected compound [24] is, without purification, dissolved into an appropriate solvent such as $CH_3CN$, or the like, and subjected to a condensation with N-protected-amino acid [8] in the same manner as the coupling reaction described in the above process I to yield a dipeptide analogue [25].

STEP 3

The compound [25] is then deprotected in the similar manner as that used for the deprotection of compound [23] in the above Process II, step 2. The product [26] is, without purification, subjected to the condensation reaction with a modified carboxylic acid [12] in the exactly same manner as described in the Process I to obtain the final product [IB].

As can be seen from the above reaction schemes, the present invention provides a dipeptide in which one peptide bond is formed through a coupling reaction between, for example, a free carboxyl group of an amino-protected amino acid and an amino group of an amino dihydric alcohol of formula [7] prepared from an oxazolidine derivative of formula [4]. The compound [4], an important intermediate for preparing the compound of formula (I), is obtained by a stereoselective aldol condensation method of the present invention. The other peptide bond is formed by a coupling reaction between a carboxylic group of, for example, sulfonyl propionic acid of formula [12] with a free amino group of a deprotected amino ketone [11] such as histidine as can be seen in the step 4.

As will be hereinafter described in the Experiment, the compounds of the invention have been demonstrated to be an effective renin inhibitor, whereby it suppresses the renin-angiotensin system (one of in vivo causes of hypertension) and lower the blood pressure. The compounds of the invention are low toxic and useful in the treatment of hypertension or cardiac dysfunction through their renin inhibitory activity. The compounds may be administered either orally or parenterally. It is characteristic benefit of the compounds that they are effective even when orally administered.

When the compounds of the invention are used to treat renin-associated disorders, a therapeutically effective amount of a compound of formula (I) is formulated into a composition of an appropriate form by known procedures using pharmaceutically acceptable carriers, diluents, or excipients. The administration may be conducted orally, intranasally, intravenously, subcutaneously, or the like.

For preparing the compositions for the oral administration, an active compound (I) is mixed with one or more standard adducts such as excipient, stabilizer, or inert diluent, and the like. The mixture is then formulated into an appropriate form such as tablet, coated tablet, hard gelatin capsule, or an aqueous, alcoholic or oily suspension, or an aqueous, alcoholic or oily solution. Examples of inert excipients which can be used include various cyclodextrins, preferably $\beta$-cyclodextrin, acacia gum, magnesium carbonate, potassium phosphate, lactose, glucose, magnesium stearyl fumarate, starch, and the like. Either of dry or wet granules can be used. Examples of oily excipients or solvents include vegetable oil such as sunflower oil and fish liver oil.

For subcutaneous or intravenous administration, an active compound or a pharmaceutically acceptable salt thereof is dissolved, dispersed or emulsified into an appropriate solvent with the aid of any substances generally used in such a purpose, for example, solubilizing agent, emulsifying agent, or other adjuncts to obtain solution, suspension or emulsion.

Examples of appropriate solvents include water, physiological saline, alcohols such as ethanol, propanediol or glycerol, a sugar solution such as a solution of glucose or mannitol, or a mixture thereof, or Tween 80. Examples of solubilizing agents include above-mentioned cyclodextrins, preferably $\beta$-cyclodextrin.

The abbreviations used are as follows:
Boc=tertiary-butoxycarbonyl; Red-Al=sodium bis(2-methoxyethoxy)aluminium, L-Selectride=lithium tri-sec-butylborohydride; Boc His(Ts)·DCHA=$N^\alpha$-Boc-$N^\tau$-tosyl-L-histidine dicyclohexylamine; BOP=-benzotriazol-1-yl-oxy-tris-(dimethylamino)phosphoniumhexafluorophosphate; DCC-HOBt=dicyclocarbodiimide-1-hydroxybenzotriazole; DCC-HOSu=-dicyclohexylcarbodiimide-N-hydroxysuccineimide; DEPC=diethyl cyanophosphonate; NMM=N-methylmorpholine; PPTS=pyridinium paratoluenesulphonate; Tala=(4-thiazolyl)-L-alanine; rt=room temperature; Ts=tosyl; TMS=trimethylsilane; DMAP=4-dimethylaminopyridine; DCHA=Dicyclohexylamine; DCC=Dicyclohexylcarbodiimide; EDC=1-Ethyl-3-(3-dimethylaminopropyl)carbodiimide; DEPA=Diethyl phosphorylazide; BOP=Benzotriazol-1-yl-oxy-tris(dimethylamino)-phosphonium hexafluorophosphate The following Examples further illustrate the compounds of the invention and the process preparing the same. The Examples are not intended to be limiting to the scope of the invention in any respect and should not so construed. Unless otherwise noted, the NMR spectra were measured in CDCl₃ at 200 MHz (internal standard=TMS) and IR spectra in CHCl₃. All amino acid used is in the L-isomer.

PREPARATION 1

3-Boc-4-(S)-cyclohexylmethyl-2,2-dimethyl-5(S)-[2-oxo-2-(4-pyridyl)ethyl]oxazolidine [4a]

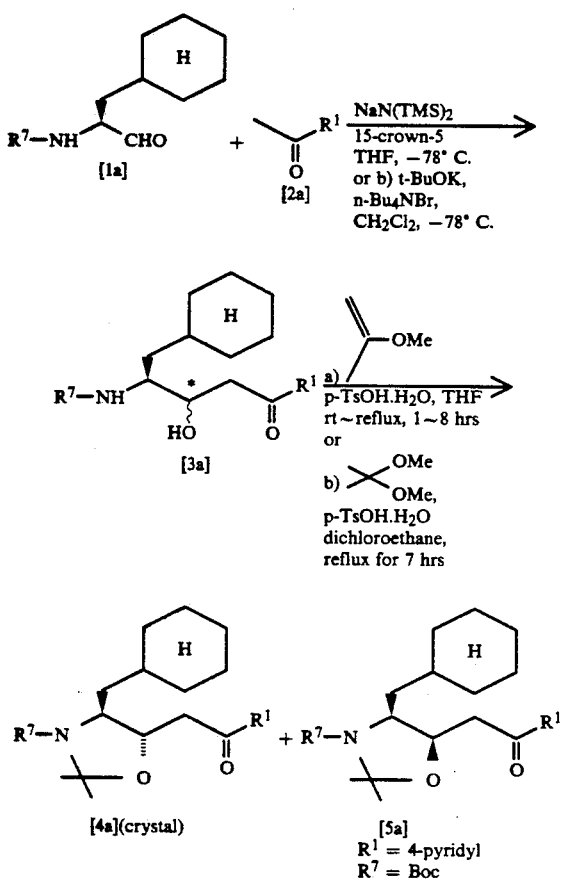

1. a) To a 36 ml (36 mmol, 1.5 eq) solution of 1N NaN(TMS)₂ in THF is added a solution of 4.34 g (36 mmol, 1.5 eq) of 4-acetylpyridine [2a] in 20 ml of THF at −78° C. over 10 minutes under nitrogen atmosphere. After 10 minutes stirring, a solution of 7.898 g (36 mmol, 1.5 eq) of 15-crown-5 in 10 ml of THF is added thereto and stirred for 5 minutes. To the mixture is added 6.108 g (24 mmol) of N-Boc-L-cyclohexylalaninal [1a] in 50 ml of THF over 15 minutes and stirred for 1 hour at −78° C. The reaction mixture is added to a mixture of saturated aqueous solution of ammonium chloride and ethyl acetate with stirring and extracted three times with ethyl acetate. The extract is washed with saturated brine, dried over magnesium sulfate and concentrated to dryness in vacuo. The residue, upon purification by column chromatography on silica gel (eluent; dichloromethane/methanol=98.5:1.5) gives N-Boc-1 (S)-cyclohexylmethyl-2-hydroxy-4-oxo-4-(4-pyridyl)-butylamine [3a] (5.94 g; yield=66.0%) as a colorless powder. The product is a mixture of compound of 2(S)-isomer (desired isomer) and 2(R)-isomer (the ratio of 2(S):2(R)=5.24:1).

b) To a stirring solution of 32 g (125.3 mmol) of N-Boc-L-cyclohexylalaninal [1a], 22.8 g (188 mmol, 1.5 eq) of N-acetylpyridine, and 60.6 g (188 mmol, 1.5 eq) of tetrabutyl ammnonium bromide in 700 ml of dichromethane is added each one fourth portions of t-BuOK (21.1 g in total, 188 mmol, 1.5 eq.) at 10 minutes interval under cooling at −78° C. and the stirring is continued for another 1.5 hours at the same temperature. The reaction mixture is added to a mixture of saturated aqueous ammonium chloride and dichloromethane with stirring and extracted three times with dichloromethane. The extract is treated with citric acid to purify the basic substances to obtain a crude product [3a] (37 g; yield=79%; 2(S)/2(R)=7:1).

2. a) To a solution of 5.908 g (15.7 mmol) of purified alcohol [3a] in 50 ml of THF are added 2 ml (20.9 mmol, 1.3 eq) of 2-methoxypropene and 299 mg (1.57 mmol, 0.1 eq) of p-toluenesulfonic acid monohydrate and the mixture is heated to reflux for 4 hrs. The reaction mixture is concentrated under a reduced pressure, and the residue is alkalified with 4% sodium bicarbonate and extracted 3 times with dichloromathane. The extract is washed once with saturated brine, dried over magnesium sulfate, and concentrated to dryness. The residue is decolorized by column chromatography on silica gel using a short column (eluent; dichloromethane/acetonitrile=5:1) and recrystallized from ethyl acetate to obtain 4.66 g (yield=68.6%) of the title compound [4a] as a colorless solid.

b) A mixture of 72 g (195.6 mmol) of the crude alcohol [3a], 150 ml (122.0 mmol, 6.2 eq) of 2,2-dimethoxypropane and 2.73 g (14.4 mmol, 0.073 eq) of p-toluenesulfonic acid monohydrate in 150 ml of dichloroethane is heated to reflux for 16 hours. After cooling, the mixture is made basic with 4% aqueous sodium bicarbonate and extracted 3 times with dichloromethane. The extract is washed once with saturated brine, dried over magnesium sulfate, concentrated to dryness in vacuo. The crude product, upon recrystallization from isopropyl ether, gives 23.5 g (29.5%) of the compound [4a] as a white crystal. The mother liquor, when treated by a column chromatography on 300 g of silica gel (eluent; dichloromethane/ethyl acetate=7:1) and recrystallized in the same manner as above, gives 2.5 g (3.1%) of compound [4a].

m.p.=115°−116° C.

[α]$_D$= −18.5° (C=1.0; CHCl₃; 23.5° C.)

IRνmax(CHCl₃):1692, 1596, 1557, 1477, 1450, 1172, 1086 cm⁻¹ NMRδ (CDCl₃):1.48(9H,s), 1.52(3H,s), 1.60(3H,s), 0.78−1.90(13H,m), 3.14(1H,dd,J=16.8,6.8Hz), 3.41(1H,dd,J=16.7,6.1Hz), 3.84(1H,m), 4.52(1H,t like m), 7.73(2H,m), 8.83(2H,m)

Elemental analysis (as C₂₄H₃₆N₂O₄); Calcd. (%): C:69.20; H:8.71; N:6.73; Found (%) C:69.20; H:8.75; N:6.76.

PREPARATION 2-20

Compounds [4], the desired stereoisomers, were prepared according to the method described in above Preparation 1 by preparing compound [3a] and separating the desired isomer [3]-(S) therefrom. The results are shown in the following Table 1. Among the compounds listed in the Table 1, compound Nos. 13 and 14 are separated chromatographically because the corresponding compounds of formula [4] do not crystallize under the conditions used.

TABLE 1

$$\text{Boc-NH}-\overset{H}{\underset{\text{CHO}}{C}}-\text{Cy} + \overset{O}{\underset{R^1}{C}} \longrightarrow \text{Boc-NH}-\overset{1}{C}-\overset{2}{\underset{OH}{C}}-\overset{3}{C}-\overset{4}{\underset{O}{C}}-R^1 \longrightarrow \text{Boc-N}-\overset{S}{\underset{O}{C}}-R^1$$

[1]    [2]    [3]    [4]

| Compd. of Prep. No. | R¹ | [3] Yield % | [3] C-2 S/R | [4] Yield % | [4] mp °C. | [4] $[\alpha]_D$ C = 1.0, CHCl₃ (°C.) | [4] Elemental analysis | [4] Calcd. | [4] Found | [4] IR $\nu_{max}$ cm⁻¹ |
|---|---|---|---|---|---|---|---|---|---|---|
| 2 | phenyl | 71 | 3.1 | 70 | 111~113 | −17.4 (23.5) | C₂₅H₃₇NO₄ | C: 72.25 H: 8.98 N: 3.37 | C: 72.25 H: 8.99 N: 3.36 | 1686, 1650, 1582, 1478, 1450, 1172, 1088 |
| 3 | o-fluoro-phenyl | 68 | 4.8 | 75 | 95~97 | −18.5 (24.0) | C₂₅H₃₆NO₄F | C: 69.25 H: 8.37 N: 3.23 F: 4.38 | C: 69.12 H: 8.10 N: 3.23 F: 4.45 | 1686, 1610, 1577, 1480, 1453, 1173, 1100, 1086, 990, 848 |
| 4 | m-methoxy-phenyl | 75 | 2.7 | 80 | 117~119 | −6.2 (23.5) | C₂₆H₃₉NO₅ | C: 70.08 H: 8.82 N: 3.14 | C: 70.05 H: 8.74 N: 3.15 | 1689, 1600, 1585, 1488, 1465, 1456, 1430, 1394, 1369, 1290, 1255, 1172, 1139, 1088, 1050 |
| 5 | p-methyl-phenyl | 78 | 2.4 | 69 | 132~134 | −23.5 (24.0) | C₂₆H₃₉NO₄ | C: 72.69 H: 9.15 N: 3.26 | C: 72.66 H: 9.08 N: 3.20 | 1687, 1610, 1573, 1480, 1450, 1174, 1088. |
| 6 | 2,4-difluoro-phenyl | 91 | 4.8 | 69 | 136~137 | −19.1 (23.5) | C₂₅H₃₅NO₄F₂ | C: 66.49 H: 7.81 N: 3.10 F: 8.42 | C: 66.31 H: 7.82 N: 3.04 F: 8.38 | 1687, 1612(1595), 1498, 1477, 1450, 1430, 1172, 1140, 1098, 971, 855 |
| 7 | 1-naph-thyl | 90 | 1.7 | 60 | 127~128 | −11.7 (24.0) | C₂₉H₃₉NO₄ | C: 74.81 H: 8.44 N: 3.01 | C: 74.84 H: 8.43 N: 3.06 | 1687, 1595, 1508, 1477, 1449, 1393, 1379, 1368, 1250, 1172, 1138, 1098, 1085 |
| 8 | 3-thienyl | 80 | 2.7 | 62 | 113–114 | −13.5 (25) | C₂₃H₃₅NO₄S | C: 65.52 H: 8.37 N: 3.32 S: 7.61 | C: 65.75 H: 8.28 N: 3.31 S: 7.57 | 1685, 1510, 1477, 1450, 1172, 1088 |
| 9 | 2-thia-zolyl | 75 | 16 | 72 | 128~129 | −10.7 (23.5) | C₂₂H₃₄N₂O₄S | C: 62.53 H: 8.11 N: 6.63 S: 7.59 | C: 62.28 H: 7.79 N: 6.53 S: 7.36 | 1690, 1480, 1448, 1170, 1075, 945 |

| Compd. of Prep. No. | R¹ | [3] Yield % | [3] C-2 S/R | [3](S) or [4] Yield % | [3](S) or [4] mp °C. | [3](S) or [4] $[\alpha]_D^{24}$ C = 1.0, CHCl₃ (°C.) | [3](S) or [4] Elemental analysis | [3](S) or [4] Calcd. | [3](S) or [4] Found | [3](S) or [4] IR $\nu_{max}$ cm⁻¹ or NMR (δ) |
|---|---|---|---|---|---|---|---|---|---|---|
| 10 | m-fluoro-phenyl | 82 | 3.9 | 71 | 103~105 | −15.7° | C₂₅H₃₆N₁O₄F | C: 69.25 H: 83.7 N: 3.23 F: 4.38 | C: 69.36 H: 8.41 N: 3.25 F: 4.22 | 1690, 1610, 1590, 1485, 1475, 1443, 1392, 1170, 1086 |
| 11 | p-fluoro-phenyl | 83 | 2.8 | 61 | 137~138 | −15.7° | C₂₅H₃₆N₁O₄F | C: 69.25 H: 8.37 N: 3.23 F: 4.38 | C: 69.14 H: 8.35 N: 3.14 F: 4.41 | 1685, 1600, 1505, 1475, 1450, 1392, 1170, 1155, 1085 |
| 12 | 2,6-difluoro-phenyl | 88 | 13.0 | 83 | 51~54 | −18.8° | C₂₅H₃₅N₁O₄F₂ | C: 66.50 H: 7.81 N: 3.10 F: 8.41 | C: 66.40 H: 7.79 N: 3.34 F: 8.69 | 1691, 1624, 1588, 1467, 1450, 1394, 1369, 1279, 1174, 1139, 1089, 1030, 982, 860 |
| 13 | o-methoxy-phenyl | 79 | 2.8 | [3](S) 53 | | | | | | 0.75~1.93(13H, m), 1.45(9H, s), 3.10(1H, dd, J=9.9, 18.3Hz), 3.70(1H, m), 4.16(1H, m), 4.82(1H, d, J=10Hz), 7.00(2H, m), 7.50(1H, td, J=2.5, 7Hz), 7.75(1H, dd, J=2.5, 7Hz) |
| 14 | o-chloro-phenyl | 86 | 3.0 | [3](S) 57 | | −36.8° | | | | 0.74~1.90(13H, m), 1.44(9H, m), 3.18(2H, m), 3.71(1H, m), 4.20(1H, m), 4.75(1H, d, J=10Hz), 7.22~7.59(4H, m) |
| 15 | m-cyano-phenyl | 70 | 2.8 | 68 | 114~117 | −14.7° | C₂₆H₃₆N₂O₄ | C: 70.88 H: 8.24 N: 6.36 | C: 70.87 H: 8.27 N: 6.16 | 2236, 1693, 1602, 1479, 1450, 1394, 1369, 1172, 1088 |
| 16 | o-methyl-sulfonyl amino- | 67 | 1.5 | 51 | 131~132 | −3.3° | C₂₆H₄₀N₂O₆S | C: 61.39 H: 7.93 N: 5.51 | C: 61.00 H: 7.85 N: 5.48 | 1691, 1656, 1607, 1578, 1496, 1453, 1394, 1369, 1342, 1279, 1156, 1089, 967, 918 |

TABLE 1-continued

|         |              |         |     | phenyl |          |          | S: 6.30 | S: 6.22 |         |
|---------|--------------|---------|-----|--------|----------|----------|---------|---------|---------|

| Compd. of Prep. No. | $R^1$ | Yield % | C-2 S/R | Yield % | mp °C. | $[\alpha]_D$° CHCl$_3$ (°C.) | Elemental analysis | C = 1.0, Calcd. | Found | IR $\nu_{max}$cm$^{-1}$ |
|---|---|---|---|---|---|---|---|---|---|---|
| 17 | p-tri-fluoro-methyl-phenyl | 75 | 4.9 | 80 | 128~130 | −1.6 (24) | $C_{26}H_{36}F_3NO_4$ | C: 64.58<br>H: 7.50<br>N: 2.90<br>F: 11.79 | C: 64.83<br>H: 7.54<br>N: 2.89<br>F: 12.02 | 1690, 1582, 1510, 1450, 1325, 1172, 1137, 1066 |
| 18 | m-morpho-lino-carbonyl-phenyl | 70 | 2.7 | 80 | 154~157 | −3.6 (23) | $C_{30}H_{44}N_2O_6$ | C: 68.16<br>H: 8.39<br>N: 5.30 | C: 68.04<br>H: 8.44<br>N: 5.36 | 1690, 1632, 1484, 1451, 1438, 1394, 1369, 1303, 1277, 1172, 1141, 1116, 1087, 1025 |
| 19 | m-(N-morpho-lino)-ethoxy-phenyl | 71 | 3.0 | 39 | 117~119 | −13.5 (23.5) | $C_{31}H_{48}N_2O_6 \cdot \frac{1}{4} H_2O$ | C: 67.33<br>H: 8.90<br>N: 5.10 | C: 67.55<br>H: 8.72<br>N: 5.06 | 1686, 1650, 1582 |
| 20 | m-(N-2-formyl)-methyl-amino-phenyl | 85 | 2.8 | 53 | 117~118 | −16.5 (24.0) | $C_{27}H_{40}N_2O_5$ | C: 68.62<br>H: 8.53<br>N: 5.93 | C: 68.68<br>H: 8.43<br>N: 5.93 | 1680, 1602, 1585, 1486, 1476, 1447, 1393, 1378, 1367 |

PREPARATION 21

Boc-His(Ts)-1(S)-cyclohexylmethyl-2(S)-hydroxy-4-oxo-4-(4-pyridyl)butylamide [10a]

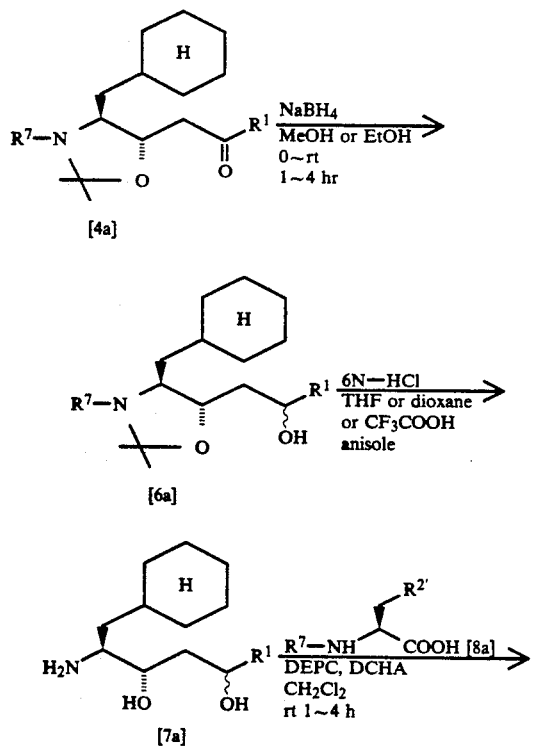

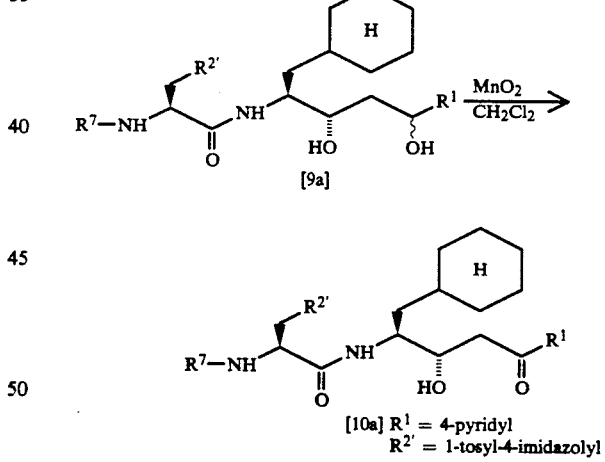

[10a] $R^1$ = 4-pyridyl
$R^{2'}$ = 1-tosyl-4-imidazolyl

To a 3-Boc-4-(S)-cyclohexylmethyl-2,2-dimethyl-5(S)-[2-oxo-2-(4-pyridyl)ethyl]oxazolidine[4a](4.66 g, 11.18 mmol) is dissolved in ethanol (20 ml) is added sodium borohydride (508 mg, 13.42 mmol) with stirring and ice-cooling and the mixture is allowed to react at room temperature for one hour. The solvent is removed in vacuo. To the residue are added ice water and saturated aqueous ammonium chloride, and the mixture is extracted with dichloromethane three times. The organic layer is washed with saturated aqueous sodium chloride, dried over MgSO$_4$, and evaporated to dryness in vacuo to obtain 3-Boc-4(S)-cyclohexylmethyl-2,2-dimethyl-5(S)-[2-hydroxy-2-(4-pyridyl)ethyl]oxazolidine [6a](4.88 g, quantitative amount) in colorless powder. The product is then, without further purification, dissolved in THF (2 ml), and 6N HCl (16 ml) is added thereto, and the mixture is stirred at room temperature for one hour. The reaction mixture is neutralized with 6N NaOH, alkalified with sodium bicarbonate, and then extracted five times with dichloromethane containing 10% methanol. The extract is dried over MgSO₄ and evaporated to dryness in vacuo to obtain 1(S)-cyclohexylmethyl-2(S), 4-dihydroxy-4-(4-pyridyl)butylamine [7a] (3.3 g, quantitative amount, diastereomer ratio 1:1) in colorless powder. The product (3.30 g) is then, without further purification, dissolved in dichloromethane (100 ml). To the solution are added Boc-His(Ts)·DCHA [8a] (8.3 g, 14.05 mmol, 1.3 eq) and diethyl cyanophosphonate (2.29 g, 14.05 mmol, 1.3 eq), and the mixture is stirred for 6 hours at room temperature. The reaction mixture is evaporated to dryness in vacuo, and the residue is purified with silica gel chromatography (CH₂Cl₂:MeOH=95:5) to obtain Boc-His(Ts)-1(S)-cyclohexylmethyl-2(S), 4-dihydroxy-4-(4-pyridyl)-butylamide [9a] (6.00 g, 80%) as a mixture of two diastereomers. The product [9a] may be used in the following reaction without separation of the two isomers.

To the solution of product [9a] (1.0 g, 1.45 mmol) in dichloromethane (3 ml) is added MnO₂ (5 g) at room temperature, and the mixture is stirred for six hours. The resultant black suspension is filtered on a Celite layer overlaid with active carbon, and insoluble material on the layer is thoroughly washed with CH₂Cl₂—MeOH (10:1). The filtrate is evaporated to dryness in vacuo and purified with silica gel chromatography (CH₂Cl₂:MeOH=95:5) to obtain the title compound [10a] (683 mg, 69%) in colorless powder.

NMRδ(CDCl₃): 1.34(9H,s), 0.70-2.20(13H,m), 2.45(3H,s), 2.99(2H,m), 3.03(1H,dd,J=17.8,2.3Hz), 3.34(1H,dd,J=17.8,9.6Hz),
4.04(1H,ddd,J=8.7,8.7,8.7Hz), 4.23(1H,m), 4.30(1H,ddd,J=5.8,5.8,5.8Hz), 6.16(1H,m), 6.47(1H,d,J=10Hz), 7.11(1H,s), 7.36(2H,d,J=8Hz), 7.80(2H,m), 7.81(2H,d,J=8.6Hz), 7.92(1H,s), 8.82(2H,d,J=5Hz).

IR ν(CHCl₃)max cm⁻¹: 3680, 3420, 3300(br), 1700, 1670, 1625, 1598, 1555, 1492, 1450, 1410, 1385, 1370, 1180, 1080, 1010.

PREPARATION 22

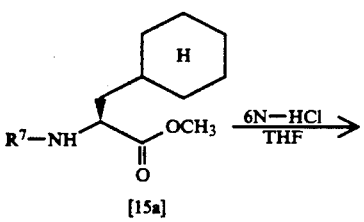

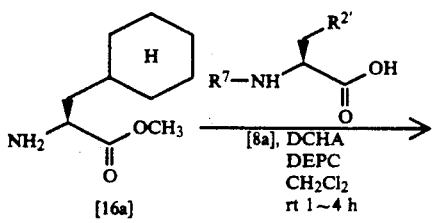

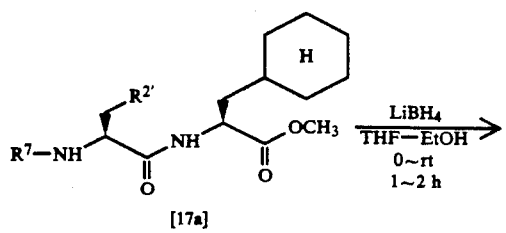

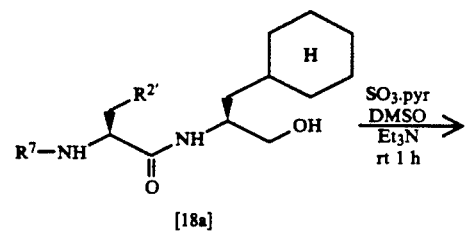

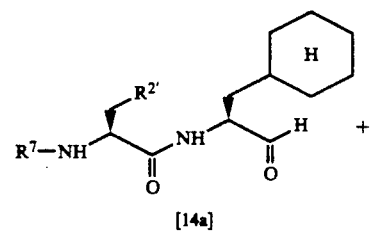

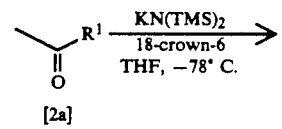

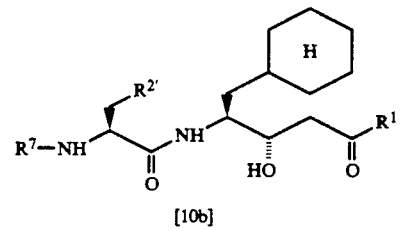

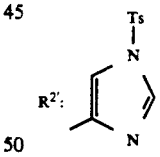

A solution of N-Boc-3-cyclohexyl-alanine methyl ester [15a] (4.00 g, 13.93 mmol) in THF (10 ml) is stirred in the presence of 6N HCl (40 ml) at room temperature for four hours. The reaction mixture is made alkaline with powdery sodium bicarbonate and extracted with dichloromethane containing 5% methanol (100 ml×4).

The extract is dried over MgSO₄ and evaporated to dryness in vacuo to quantitatively obtain 3-cyclohexylalanine methyl ester [16a] as an oil. The product is then, without further purification, dissolved in dichloromethane (50 ml) To the solution are added Boc-His(Ts) DCHA [8a] (10.7 g, 18.11 mmol, 1.3 eq) and diethyl cyanophosphonate (2.95 g, 18.1 mmol, 1.3 eq), and the mixture is stirred for 1.5 hours at room temperature. The reaction mixture is subjected to silica gel chromatography (SiO₂:300 g, CH₂Cl₂:MeOH=99:1) to give a purified Boc-His(Ts)-3-cyclohexylalanine methyl ester [17a] (7.43 g, 93%) as an oil. To a solution of the dipeptide ester [17a] (3.0 g, 5.2 mmol) in THF (6 ml) and ethanol (6 ml) is added a 2N solution of lithium borohydride in THF (3 ml, 6 mmol) with stirring and ice-cooling. After 20 minutes stirring, the mixture is allowed to react at room temperature for additional one hour. The solvent is removed in vacuo and the residue added ice water and saturated aqueous ammonium chloride is extracted with dichloromethane (20 ml×3). The organic layer is washed with saturated aqueous sodium chloride, dried over MgSO4, evaporated to dryness in vacuo and the residue is purified by silica gel chromatography (SiO2:200 g, CH2Cl2:MeOH=98:2) to obtain Boc-His(Ts)-3-cyclohexyl-alaninol [18a] (2.06 g, 72%) as an oil.

To a mixture of the dipeptide alcohol [18a] (2.0 g, 3.65 mmol), triethylamine (1.30 g, 12.85 mmol, 3.5 eq) and DMSO (6 ml) is added at room temperature SO3.-pyridine (2.03 g, 12.75 mmol, 3.5 eq) in DMSO (6 ml) and the mixture is stirred for 35 minutes. The reaction mixture is poured on ice, and the resultant aqueous mixture is extracted with ethyl acetate (20 ml×3). The organic layer is subsequently washed with 10% aqueous citric acid, saturated aqueous sodium chloride (×2), 7% aqueous sodium bicarbonate, and saturated aqueous sodium chloride, dried over MgSO4, and concentrated to dryness in vacuo. The resultant residue is purified with silica gel chromatography (SiO2:100 g, CH2Cl2:MeOH=95:5) to obtain Boc-His(Ts)-3-cyclohexylalaninal [14a] (1.67 g, 84%) in amorphous powder.

To a 0.5N potassium bis-trimethylsilylamide solution in toluene (9.2 ml, 4.60 mmol, 2.5 eq) is added dropwise at −78° C. cyclohexyl methyl ketone (0.58 g, 4.60 mmol, 2.5 eq) in THF (9 ml) with stirring under a nitrogen atmosphere over 10 minutes. After 20 minutes stirring at the same temperature, 18-crown-6 (1.216 g, 4.60 mmol, 2.5 eq) in THF (10 ml) is dropwise added to the mixture over two minutes. Further, the dipeptidealdehyde [14a] (1.0 g, 1.83 mmol) in THF (10 ml) is dropwise added over 15 minutes at −78° C., and the mixture is stirred for one hour at the same temperature. The reaction is quenched by adding a solution of acetic acid (0.60 g, 10 mmol, 5.5 eq) in THF (10 ml) and after the addition of saturated aqueous ammonium chloride (30 ml) the mixture is extracted with ethyl acetate (50 ml×3). The organic layer is washed with saturated aqueous sodium chloride, dried over MgSO4, concentrated to dryness in vacuo, and purified with silica gel chromatography (Lobar column, CH2Cl2:MeOH=95:5) to obtain Boc-His(Ts)-1(S)-cyclohexylmethyl-2(S)-hydroxy-4-oxo-4-cyclohexyl-butylamide [10b] (0.18 g, 15%) in amorphous powder.

NMR δ: 1.30–1.90(23H,m), 1.40(9H,s), 2.32(1H,m), 2.44(3H,s), 2.59(2H,m), 2.93(1H,dd,J=5.8,9 6Hz), 3.04(1H,dd,J=5.8,9.6Hz),
3.89(1H,ddd,J=8.4,8.4,8.4Hz), 3.98(1H,m),
4.30(1H,ddd,J=6.0,6.0,6.0Hz), 6.12(1H,d,J=6.0Hz),
6.47(1H,d,J=9.8Hz), 7.10(1H,d,J=0.8Hz),
7.36(2H,d,J=8.0Hz), 7.81(2H,d,J=8.4Hz),
7.93(1H,d,J=1.2Hz).

PREPARATION 23

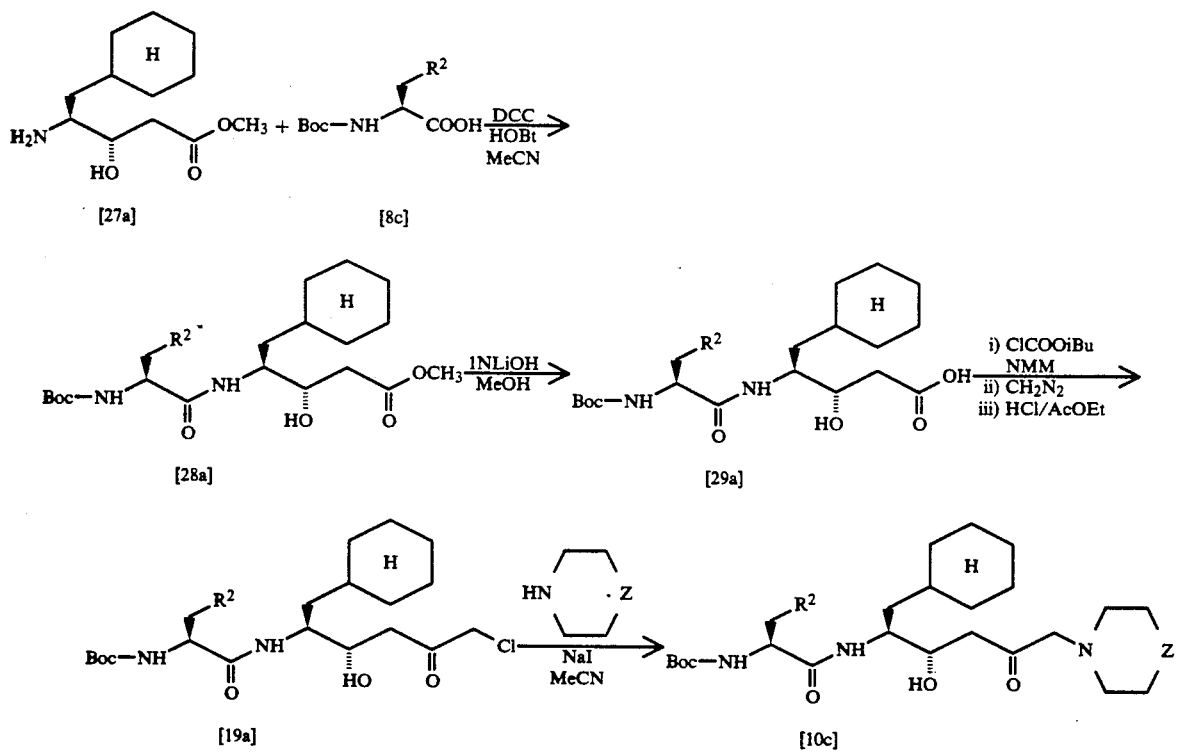

$R^2$ = 4-thiazolyl
$Z$ = O

To a solution of cyclostatine methyl ester [27a] (700 mg, 3.05 mmol), Boc-(4-thizolyl)-L-alanine [8c] (869 mg, 3.19 mmol, 1.05 eq), and HOBt (431 mg, 3.19 mmol, 1.05 eq) in CH3CN (10 ml) is added DCC (660 mg, 3.20 mmol), 1.05 eq) with stirring and ice-cooling under nitrogen atmosphere and the mixture is stirred for 1.5 hours at the same temperature and then allowed to react at room temperature for 14 hours. Ethyl acetate is added to the mixture, and precipitated crystals were filtered off. The filtrate is concentrated to dryness in vacuo and the residue is subjected to silica gel chromatography (SiO$_2$:100 g, NH$_4$OH:MeOH:CH$_2$Cl$_2$=1:10:990) to give the aimed product, Boc-(4-thiazolyl)alanyl-cyclostatine methyl ester [28a] (830 mg, 59%) as an oil.

To the solution of the above product [28a] (830 mg, 1.72 mmol) in MeOH (2 ml) is added 1N LiOH (1.9 ml, 1.9 mmol, 1.1 eq) with stirring and ice-cooling. The mixture is stirred for 10 minutes and allowed to react at room temperature for two hours. After neutral substances are removed by washing with dichloromethane, the mixture acidified with citric acid is extracted with ethyl acetate. The organic layer is dried over MgSO$_4$, and concentrated to dryness in vacuo to obtain the aimed carboxylic acid [29c] (700 mg, 87%).

To a mixture of the above carboxylic acid [29a] (700 mg, 1.67 mmol) and N-methylmorpholine (0.17 ml, 1.67 mmol) in THF (10 ml) is added isobutyl chlorocarbonate (0.2 ml, 1.67 mmol) with stirring at temperature of $-15°$ C.$--10°$ C. under nitrogen atmosphere, and the resultant mixture is stirred for 50 minutes at the same temperature. After precipitated crystals are removed by filtration, the filtrate added a solution of diazomethane (2.2 eq) in ethyl ether previously prepared at $-10°$ C. is allowed to react at room temperature for 3 hours. The reaction mixture is concentrated in vacuo to remove diazomethane and ethyl acetate (10 ml) is added to the residue. After addition of 2N HCl (3 ml) at $-40°$ C.$--30°$ C., the mixture is allowed to react for one hour. The reaction mixture is alkalified by addition of saturated aqueous sodium bicarbonate and the ethyl acetate layer is separated. The layer is dried over MgSO$_4$ concentrated to dryness in vacuo to obtain 800 mg of crude chloromethyl ketone [19a]. Since the product tends to get colored and decomposed, it is immediately used in the next step without purification.

To a solution of the above product [19a] (400 mg) in MeCN (5 ml) are added morpholine (150 mg) and catalytic amount of NaI, and the mixture is stirred at room temperature for two hours. The reaction mixture is purified by chromatography to give the aimed compound, Boc-(4-thiazolyl)alanyl-1(S)-cyclohexylmethyl-2(S)-hydroxy-4-oxo-4-(N-morpholino)methyl-butylamide [10c] (Z=O) (120 mg, 29% starting from [29a]).

NMR$\delta$: 0.6–2.00(13H,m), 1.43(9H,s), 2.55(4H,m), 3.22(2H,dd,J=4.6,14.8Hz), 3.26(2H,s), 3.43(1H,dd,J=5.4,14.8Hz), 3.76(4H,m), 3.89(1H,m), 3.94(1H,m), 4.44(1H,ddd,J=6.2Hz×3), 6.38(1H,d,J=9.8Hz), 6.48(1H,d,J=7.5Hz),7.13(1H,d,J=1.8Hz), 8.79(1H,d,J=2Hz).

PREPARATION 24

In the same manner as in Preparation 23, Boc-(4-thiazolyl)alanyl-1(S)-cyclohexylmethyl-2(S)-hydroxy-4-oxo-4-(N-piperidino)methyl-butylamide [10d] (Z=CH$_2$) is obtained with a overall yield of 29%.

NMR$\delta$: 0.06–1.83(19H,m), 1.44(9H,s), 2.46(4H,m), 3.15(2H,s), 3.20(1H,dd,J=5.6,14.8Hz) 3.44(1H,dd,J=5,14.8Hz) 3.89(2H,m), 4.47(1H,m), 6.41(1H,bs), 6.43(1H,d,J=9.8Hz), 7.12(1H,d,J=1.8Hz), 8.78(1H,d,J=1.8Hz).

PREPARATION 25-50

Starting from the compounds [4] which have been prepared in Preparation 2-20, the ketone compounds [10] are obtained in the same manner as in Preparation 21. The thus obtained products are listed in Table 2.

PREPARATION 51-57

The aldol reaction between dipeptides [14] and methyl ketones [2] gives ketone compounds [10] in the same manner as in Preparation 22. The thus obtained products are listed in Table 3.

TABLE 2

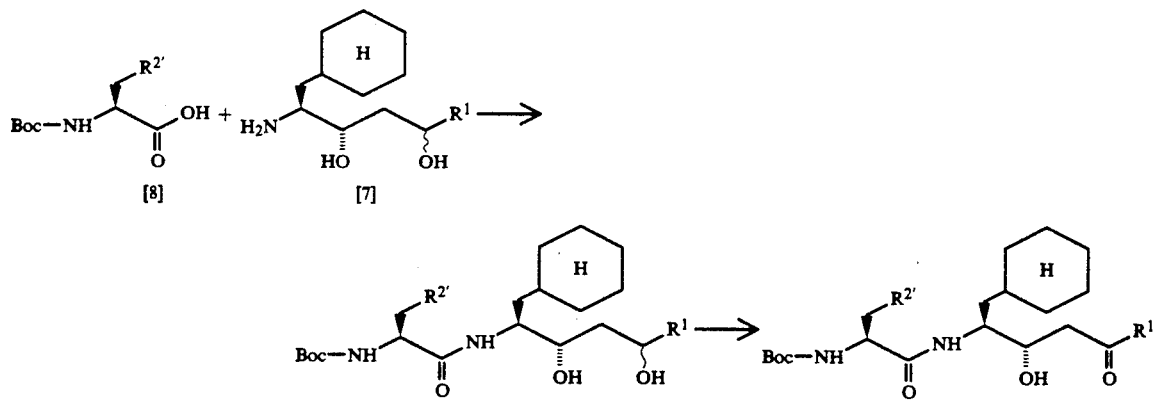

| Compd. of Prep. No. | R$^1$ | R$^{2'}$ | [a] Yield (%) (from [7]) | Yield [10] % | IR$\nu_{max}$cm$^{-1}$ or NMR($\delta$) |
|---|---|---|---|---|---|

TABLE 2-continued

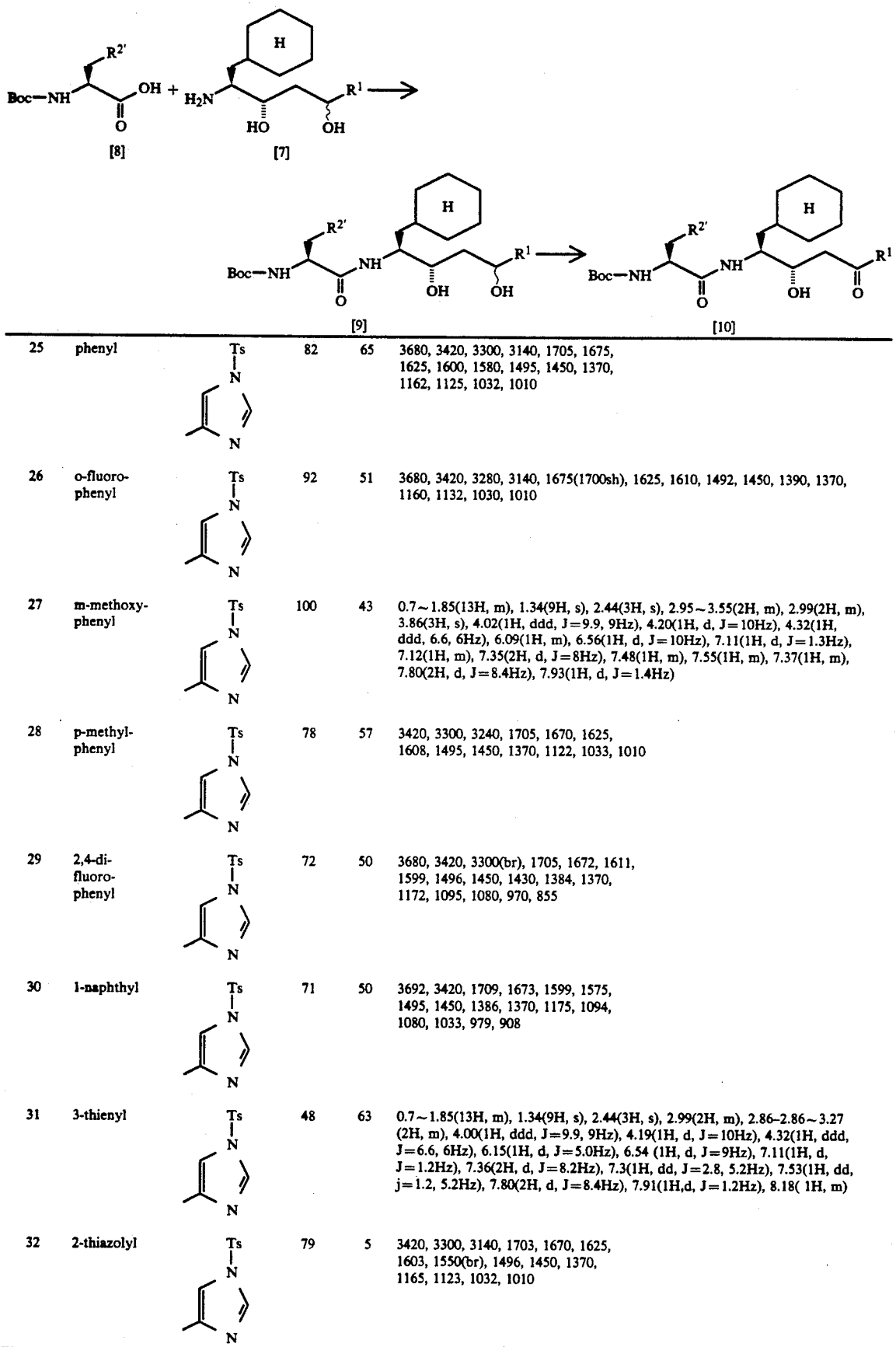

| | | | | | |
|---|---|---|---|---|---|
| 25 | phenyl | Ts-N(imidazole-methylprenyl) | 82 | 65 | 3680, 3420, 3300, 3140, 1705, 1675, 1625, 1600, 1580, 1495, 1450, 1370, 1162, 1125, 1032, 1010 |
| 26 | o-fluoro-phenyl | Ts-N(imidazole-methylprenyl) | 92 | 51 | 3680, 3420, 3280, 3140, 1675(1700sh), 1625, 1610, 1492, 1450, 1390, 1370, 1160, 1132, 1030, 1010 |
| 27 | m-methoxy-phenyl | Ts-N(imidazole-methylprenyl) | 100 | 43 | 0.7~1.85(13H, m), 1.34(9H, s), 2.44(3H, s), 2.95~3.55(2H, m), 2.99(2H, m), 3.86(3H, s), 4.02(1H, ddd, J=9.9, 9Hz), 4.20(1H, d, J=10Hz), 4.32(1H, ddd, 6.6, 6Hz), 6.09(1H, m), 6.56(1H, d, J=10Hz), 7.11(1H, d, J=1.3Hz), 7.12(1H, m), 7.35(2H, d, J=8Hz), 7.48(1H, m), 7.55(1H, m), 7.37(1H, m), 7.80(2H, d, J=8.4Hz), 7.93(1H, d, J=1.4Hz) |
| 28 | p-methyl-phenyl | Ts-N(imidazole-methylprenyl) | 78 | 57 | 3420, 3300, 3240, 1705, 1670, 1625, 1608, 1495, 1450, 1370, 1122, 1033, 1010 |
| 29 | 2,4-di-fluoro-phenyl | Ts-N(imidazole-methylprenyl) | 72 | 50 | 3680, 3420, 3300(br), 1705, 1672, 1611, 1599, 1496, 1450, 1430, 1384, 1370, 1172, 1095, 1080, 970, 855 |
| 30 | 1-naphthyl | Ts-N(imidazole-methylprenyl) | 71 | 50 | 3692, 3420, 1709, 1673, 1599, 1575, 1495, 1450, 1386, 1370, 1175, 1094, 1080, 1033, 979, 908 |
| 31 | 3-thienyl | Ts-N(imidazole-methylprenyl) | 48 | 63 | 0.7~1.85(13H, m), 1.34(9H, s), 2.44(3H, s), 2.99(2H, m), 2.86-2.86~3.27 (2H, m), 4.00(1H, ddd, J=9.9, 9Hz), 4.19(1H, d, J=10Hz), 4.32(1H, ddd, J=6.6, 6Hz), 6.15(1H, d, J=5.0Hz), 6.54 (1H, d, J=9Hz), 7.11(1H, d, J=1.2Hz), 7.36(2H, d, J=8.2Hz), 7.3(1H, dd, J=2.8, 5.2Hz), 7.53(1H, dd, j=1.2, 5.2Hz), 7.80(2H, d, J=8.4Hz), 7.91(1H,d, J=1.2Hz), 8.18( 1H, m) |
| 32 | 2-thiazolyl | Ts-N(imidazole-methylprenyl) | 79 | 5 | 3420, 3300, 3140, 1703, 1670, 1625, 1603, 1550(br), 1496, 1450, 1370, 1165, 1123, 1032, 1010 |

TABLE 2-continued

Boc—NH—CH(R²')—C(=O)—OH + H₂N—CH(CH₂-cyclohexyl)—CH(OH)—CH₂—CH(OH)—R¹ →
[8]  [7]

Boc—NH—CH(R²')—C(=O)—NH—CH(CH₂-cyclohexyl)—CH(OH)—CH₂—CH(OH)—R¹ → Boc—NH—CH(R²')—C(=O)—NH—CH(CH₂-cyclohexyl)—CH(OH)—CH₂—C(=O)—R¹
[9]  [10]

| Compd. of Prep. No. | R¹ | R²' | [a] Yield (%) (from [7]) | Yield % | [10] IR $\nu_{max}$ cm⁻¹, NMR(67), [α]$_D$°, m.p. |
|---|---|---|---|---|---|
| 33 | m-fluorophenyl | Ts-N-CH=C(CH₃)-N= (imidazole) | 76 | 45 | 3420, 3280, 3140, 1675, 1625, 1590, 1495, 1160, 1122, 1030, 1010 |
| 34 | p-fluorophenyl | Ts-N-CH=C(CH₃)-N= | 78 | 61 | 3420, 3320, 3140, 1670(sh1705), 1625, 1600, 1495, 1155, 1030, 1010 |
| 35 | 2,6-difluorophenyl | Ts-N-CH=C(CH₃)-N= | 88 | 30 | 3424, 1707, 1676, 1625, 1598, 1495, 1468, 1386, 1370, 1174, 1094, 1080, 1028 [α]$_D$ −6.0° (C = 1.0, CHCl₃, 24° C.) |
| 36 | o-methoxyphenyl | Ts-N-CH=C(CH₃)-N= | 31 | 55 | 0.75~1.83(13H, m), 1.36(9H, s), 2.44(3H, s), 3.00(2H, m), 3.13(2H, m), 3.90(3H, s), 3.96(1H, ddd, J=10, 10, 10Hz), 4.15(1H, m), 4.34(1H, ddd, J=7.7, 7Hz), 6.04(1H, d, J=7Hz), 6.58(1H, d, J=10Hz), 6.99(2H, m), 7.10(1H, d, J=1.2Hz), 7.35(2H, d, J=8.6Hz), 7.47(1H, m), 7.70(1H, dd, J=2, 7.8Hz), 7.80(2H, d, J=8.4Hz), 7.91(1H, d, J=1.4Hz) |
| 37 | o-chlorophenyl | Ts-N-CH=C(CH₃)-N= | 85 | 27 | 0.74~1.82(13H, m), 1.39(9H, s), 2.44(3H, s), 2.98(2H, m), 3.08(2H, m), 3.99(1H, m), 4.18(1H, m), 4.30(1H, ddd, J=7Hz), 6.05(1H, d, J=7Hz), 6.52(1H, d, J=10Hz), 7.10(1H, d, J=1.3Hz), 7.27~7.45(6H, m), 7.60(1H, m), 7.80(2H, d=8.4Hz), 7.90(1H, d, J=1.4Hz) |
| 38 | m-cyanophenyl | Ts-N-CH=C(CH₃)-N= | 67 | 51 | 3420, 2236, 1709, 1678, 1599, 1495, 1451, 1432, 1387, 1371, 1174, 1093, 1081, 909 |
| 39 | o-methylsulfonylaminophenyl | Ts-N-CH=C(CH₃)-N= | 76 | 58 | 3424, 1709, 1672, 1599, 1578, 1496, 1452, 1385, 1371, 1341, 1174, 1155, 1094, 1081, 1034, 968, 917 |

TABLE 2-continued

| Compd. of Prep. No. | R¹ | R²' | [a] Yield (%) (from [7]) | Yield % | [10] IR$\nu_{max}$cm$^{-1}$ | NMR($\delta$) |
|---|---|---|---|---|---|---|
| 40 | p-tri-fluoro-methyl-phenyl | Ts, thiazolyl-methylidene | 74 | 37 | 3420, 1705, 1675, 1625, 1575, 1325, 1170, 1135, 1080, 1065 m.p. = 133~135° C. | |
| 41 | m-morpholino-carbonyl-phenyl | Ts, thiazolyl-methylidene | 85 | 68 | 3420, 1709, 1674, 1632, 1600, 1495, 1386, 1370, 1279, 1174, 1116, 1093, 1080, 1026 | |
| 42 | phenyl | S, thiazolyl-methylidene | 90 | 57 | | 0.70~1.90(13H, m), 1.34(9H, s), 2.90~3.60(4H, m), 3.99(1H, m), 4.16(1H, m), 4.49(1H, ddd, J=6.2, 6.2, 6.2Hz), 6.46(1H, d, J=9.2Hz), 7.12 (1H, d, J=1.8Hz), 7.40~7.63(3H, m), 7.96(2H, d, J=8.4Hz), 8.76(1H, d, J=2Hz) |
| 43 | 4-pyridyl | S, thiazolyl-methylidene | 90 | 64 | | 0.70~2.05(13H, m), 1.34(9H, s), 2.95~3.50(4H, m), 4.01(1H, m), 4.19(1H, m), 4.46(1H, ddd, J=5.8Hz), 6.4(1H, d, J=8Hz), 6.55(1H, d, J=5Hz), 7.13(1H, d, J=1.8Hz), 7.78(2H, d, J=6.2Hz), 8.77(1H, d, J=1.8Hz), 8.80(1H, d, J=9.4Hz) |
| 44 | 3-thienyl | S, thiazolyl-methylidene | 86 | 80 | | 0.65~2.05(13H, m), 1.36(9H, s), 2.93(1H, d, J=17.1Hz), 3.15(1H, dd, J=17.6, 9.4Hz), 3.22(1H, dd, J=14.8, 5.4(Hz), 3.44(1H, dd, J=14.6, 5.3Hz), 3.97(1H, m), 4.15(1H, m), 4.48(1H, ddd, J=6.4, 6.4, 6.4Hz), 6.44 (1H, d, J=9.9Hz), 6.50(1H, d, J=7.5Hz), 7.12(1H, d, J=1.9Hz), 7.30(1H, dd, J=5.1, 2.9 Hz), 7.53 (1H, dd, J=5.1, 1.3Hz), 8.20(1H, d, J=1.9Hz), 8.77(1H, d, J=2.1Hz) |
| 45 | m-2-(N-morpho-lino)-ethoxy-phenyl | S, thiazolyl-methylidene | 96 | 51 | | 0.70~1.90(13H, m), 1.35(9H, s), 2.60(4H, m), 2.83(2H, t, J=5.4Hz), 3.17 (2H, m), 3.22(1H, dd, J=4.6, 14.4Hz), 3.44(1H, dd, J=5.2, 14.6Hz), 3.75 (4H, m), 3.98(1H, ddd, J=6.2, 6.2, 6.2Hz), 4.49(3H, m), 4.49(1H, ddd, J=6.2, 6.2, 6.2Hz), 6.45(2H, d, J=9.8Hz), 7.11(1H, d, J=2.0), 7.15(1H, dd, J=1.2, 2.8Hz), 7.37(1H, t, J=7.8Hz), 7.48(1H, m), 7.56(1H, d, J=7.8Hz), 8.77(1H, d, J=2.0Hz) |
| 46 | m-(N-formyl-methyl-amino | S, thiazolyl-methylidene | 97 | 77 | | 0.70~1.86(13H, m), 1.33(9H, s), 3.00(1H, dd, J=0.5, 14.8Hz), 3.23(1H, dd, J=5.2, 14.8Hz), 3.36(3H, s), 3.40(3H, m), 4.01(1H, m), 4.20(1H, d, J= 9.8Hz), 4.47(1H, ddd, J=5Hz), 6.44(1H, d, J=9.8Hz), 6.58(1H, d, J= 6.4Hz), 7.14(1H, d, J=1.8Hz), 7.39(1H, ddofd, J=1.2, 2.4, 8Hz), 7.52(1H, t, J=7.8Hz), 7.87(2H, m), 8.57(1H, s), 8.78(1H, d, J=2Hz) |
| 47 | 4-pyridyl | S, methyl-thiazolyl-methylidene | 87 | 61 | | 0.77~1.84(13H, m), 2.70(3H, s), 3.17(4H, m), 4.03(1H, m), 4.20(1H, m), 4.42(1H, ddd, J=5.8Hz×3), 6.42(1H, d, J=5Hz), 6.49(1H, d, J=10Hz), 6.89(1H, s), 7.80(2H, m), 8.81(2H, m) |

TABLE 2-continued

Boc—NH—CH(R²')—C(O)—OH + H₂N—CH(CH₂-Cy)—CH(OH)—CH₂—CH(OH)—R¹ ⟶
[8]            [7]

Boc—NH—CH(R²')—C(O)—NH—CH(CH₂-Cy)—CH(OH)—CH₂—CH(OH)—R¹ ⟶ Boc—NH—CH(R²')—C(O)—NH—CH(CH₂-Cy)—CH(OH)—CH₂—C(O)—R¹

[9]            [10]

| Compd. of Prep. No. | R¹ | R²' | [9] Yield (%) (from [7]) | [10] Yield % | [10] IR ν$_{max}$cm$^{-1}$ or NMR(δ) |
|---|---|---|---|---|---|
| 48 | phenyl | 2-(N-CHO-amino)-4-methylthiazol-5-yl (S,N,CHO structure) | 62 | 89 | 0.77~1.82(13H, m), 1.38(9H, s), 3.10(4H, m), 4.03(1H, m), 4.16(1H, m), 4.41(1H, t, J=5.2Hz), 6.71(1H, m), 6.89(1H, d, J=8.2Hz), 7.47(2H, t, J=7.8Hz), 7.59(1H, m), 7.94(2H, d, J=7.2Hz), 8.47(1H, s) |
| 49 | 4-pyridyl | —CONH₂ | 86 | 65 | 0.76~1.82(13H, m), 1.41(9H, s), 2.67(2H, m), 3.06(1H, dd, J=4.2, 18Hz), 3.27(1H, dd, J=8.4, 18Hz), 4.04(1H, m), 4.24(1H, m), 4.37(1H, t, J=6.4Hz), 7.07(1H, d, J=9.4Hz), 7.85(2H, m), 8.76(2H, m) |
| 50 | 4-pyridyl | —SMe | 66 | 36 | 0.82~1.88(13H, m), 1.38(9H, s), 2.15(3H, s), 2.87(1H, dd, J=6.4, 13.6Hz), 2.95(1H, t, J=7.6Hz), 3.10(1H, dd, J=2.2, 18.8Hz), 3.42(1H, dd, J=9.4, 18.6Hz), 4.12(1H, m), 4.23(1H, ddd, J=6Hz×3), 4.28(1H, m), 5.37(1H, d, J=6Hz), 6.55(1H, d, J=10Hz), 7.77(2H, m), 8.82(2H, m) |

TABLE 3

Boc—NH—CH(R²')—C(O)—NH—CH(CH₂-Cy)—CHO + CH₃—C(O)—R¹ ⟶ Boc—NH—CH(R²')—C(O)—NH—CH(CH₂-Cy)—CH(OH)—CH₂—C(O)—R¹

[19]      [2]      [10]

| Compd. of Prep. No. | R¹ | R²' | Yield % | NMR δ (CDCl₃) |
|---|---|---|---|---|
| 51 | p-methoxyphenyl | Ts-N-(4-methylimidazol-5-yl) | 10 | 0.75~1.94(13H, m), 1.33(9H, s), 2.44(3H, s), 3.00(2H, m), 3.08(2H, m), 3.88(3H, s), 4.01(1H, ddd, J=8.2Hz), 4.19(1H, m), 4.34(1H, ddd, J=6.4Hz), 6.12(1H, d, J=5.8Hz), 6.58(1H, d, J=9.8Hz), 6.93(2H, d, J=8.6Hz), 7.11(1H, s), 7.36(2H, d, J=8.2Hz), 7.81(2H, d, J=8.6Hz), 7.93(1H, s), 7.95(2H, d, J=9Hz) |
| 52 | 3',4'-methylenedioxyphenyl | Ts-N-(4-methylimidazol-5-yl) | 19 | 0.77~1.83(13H, m), 1.34(9H, s), 2.44(3H, s), 3.00(4H, m), 4.00(1H, ddd, J=8.4, 8.4, 8.4Hz), 4.18(1H, d, J=6.2Hz), 4.32(1H, ddd, J=6Hz), 6.05(2H, s), 6.13(1H, m), 6.54(1H, d, J=9.8Hz), 6.85(1H, d, J=8.2Hz), 7.11(1H, d, J=0.4Hz), 7.36(2H, d, J=8.4Hz), 7.43(1H, d, J=1.4Hz), 7.58(1H, td, J=8.2, 0.8Hz), 7.80(2H, d, J=8.4Hz), 7.92(1H, d, J=1.2Hz) |
| 53 | 3-thienyl | Ts-N-(4-methylimidazol-5-yl) | 23 | Identical with those of compound in Ex. No. 27 |

TABLE 3-continued

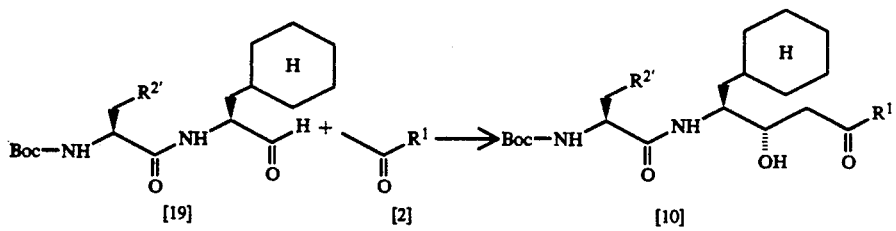

| Compd. of Prep. No. | R¹ | R²' | Yield % | NMRδ (CDCl₃) |
|---|---|---|---|---|
| 54 | morpholino-carbonyloxy-phenyl | Ts-N, (indole) | 27 | 0.72~2.00(13H, m), 1.34(9H, s), 2.44(3H, s), 3.00(2H, m), 3.10(2H, m), 3.52~3.8 (8H, m), 4.00(1H, ddd, J=8Hz), 4.18(1H, m), 4.33(1H, ddd, J=6.6Hz), 6.10(1H, m), 6.58(1H, d, J=7Hz), 7.12(1H, d, J=3.4Hz), 7.36(3H, m), 7.47(1H, t, J=8Hz), 7.68(1H, m), 7.82(3H, m), 7.94(1H, d, J=1.4Hz) |
| 55 | phenyl | Ts-N, (indole) | 28 | Identical with those of compound in Ex. No. 21 |
| 56 | N-methyl-3-pyrrolyl | S, (thiazole) | 39 | 0.70~1.85(13H, m), 1.38(9H, S), 2.81(2H, d, J=5.6Hz), 3.20(1H, dd, J=4.8, 14.2Hz) 3.45(1H, dd, J=5.2, 14.8Hz), 3.69(3H, S), 3.92(1H, m), 4.07(1H, t, J=5.8Hz), 4.49(1H, ddd, J=6.8Hz×3)6.48(1H, d, J=9.6Hz), 6.57(1H, S), 6.58(1H, S), 7.12(1H, d, J=2Hz), 7.32(1H, S), 8.77(1H, d, J=2Hz) |
| 57 | cyclohexyl | S, (thiazole) | 31 | 0.6~1.92(13H, m), 2.33(1H, m), 2.45~2.75(2H, m), 3.20(1H, dd, J=14.4, 5.2Hz) 3.44(1H, dd, J=14.8, 3.8Hz), 3.85(1H, m), 3.93(1H, m), 4.45(1H, ddd, J=6.2, 6.2, 6.2Hz)6.40(1H, d, J=9.8Hz), 6.49(1H, d, J=6.8Hz), 7.12(1H, d, J=1.6Hz), 8.78(1H, d, J=1.8Hz) |

PREPARATION 58

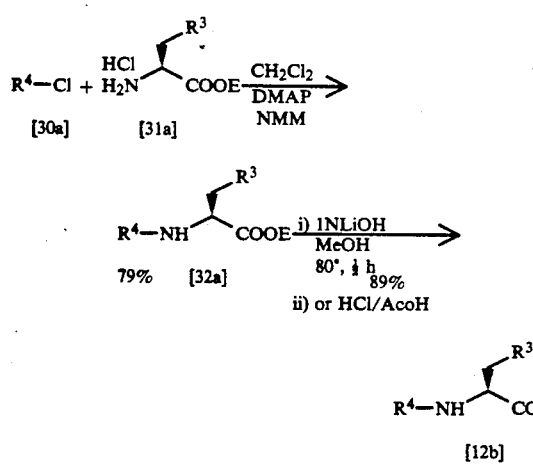

R³ = phenyl
R⁴ = (N-morpholino)sulfonyol
E = CH₃

To a suspension of methyl ester of L-phenylalanine hydrochloride [31a] (4.31 g, 20 mmol) in dichloromethane (50 ml) are added N-methylmorpholine (6.7 g, 66 mmol, 3.3 eq). N-Morpholinosulfonyl chloride [30a] (4.44 g, 24 mmol, 1.2 eq) in dichloromethane (4 ml) and subsequently DMAP (244 mg, 2.0 mmol, 0.1 eq) and the mixture is stirred overnight at room temperature. The reaction mixture is washed with 1N HCl and H₂O and the dichloromethane layer is dried over MgSO₄ and concentrated to dryness in vacuo. The residue is subjected to silica gel column chromatography (SiO₂:110 g, CH₂Cl₂:MeOH=20:1) to obtain the compound [32a] (5.16 g, 79%).

(i) To a solution of the compound [32a] (2.666 g, 8.1 mmol) in MeOH (12 ml) is added 1N LiOH (12 ml, 12 mmol, 1.5 eq) and the mixture is stirred at 80° C. for 30 minutes. After removal of MeOH in vacuo, the reaction mixture is washed with ethyl acetate. The mixture is then treated with active carbon, adjusted to pH 2-3 with 1N HCl, and extracted with ethyl acetate. The extract is washed with saturated aqueous sodium chloride, dried over MgSO₄, and concentrated to dryness in vacuo. The residue is recrystallized from ethyl acetate/n-hexane to obtain colorless needle of N-(N-morpholino)sulfonyl-phenylalanine [12b] (2.267 g, 89%).

m.p. 164°166° C. (decomposition)

(ii) To the compound [32b] (E=Et) (920 mg, 2.7 mmol) are added 6N HCl (9.2 ml) and acetic acid (2 ml) and the mixture is heated with stirring on an oil bath of 100° C. for one hour. After cooling, the reaction mixture is concentrated to dryness in vacuo. The residue is made alkaline by dissolving into saturated aqueous sodium bicarbonate. The aqueous solution is washed with dichloromethane (10 ml×3), treated with active carbon, and neutralized with 6N HCl. The solution is then made acidic up to pH 3 by addition of 10% aqueous citric acid and extracted with ethyl acetate (50 ml×3).

The organic layer is washed with saturated aqueous sodium chloride (×2), dried over MgSO₄, and concentrated to dryness in vacuo to give the compound [12c] as a crystalline residue (620 mg, 74%). Recrystallization from dichloromethane/isopropyl ether affords white crystals (543 mg, 64%). m.p. 157°–158° C.

[α]_D= −17.7±0.6° (C=1.0; MeOH; 25.0° C.) IRν-max(cm⁻¹): 3320, 3200–2600(br), 1750, 1603, 1585, 1500, 1455, 1400, 1352, 1300.

NMR(δ): 2.93(5H,m), 3.17(1H,dd,J=5.2,14.2Hz), 3.54(4H,m), 4.11(1H,dd,J=5.2,8.6Hz), 7.30(5H,m).

PREPARATION 59

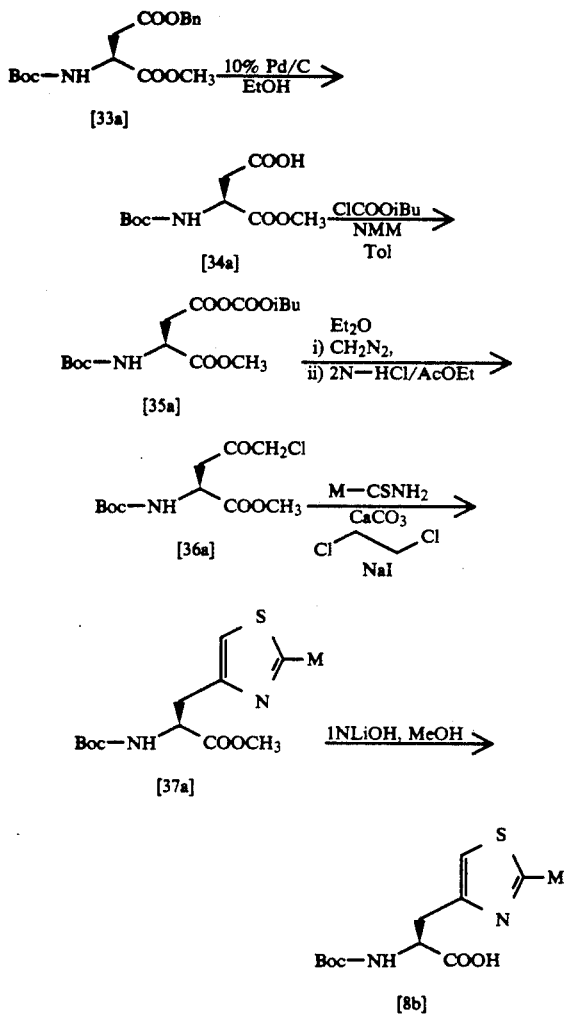

M = H a) A solution of methyl ester of N-Boc-ω-benzyl-L-aspartic acid [33a] (52.7 g, 0.156 mmol) in a mixture of water (10 ml), acetic acid (10 ml) and methanol (150 ml) is subjected to a catalytic reduction in the presence of 10% Pd-C (4.0 g) under a atmosphere of hydrogen gas at room temperature. The reduction is conducted with stirring and under atmospheric pressure. After 3-hour reaction, the catalyst is filtered off and the filtrate is evaporated to dryness in vacuo. The residue is dissolved in saturated aqueous sodium bicarbonate and the aqueous layer is washed with dichloromethane (50 ml×3), made acidic with citric acid (about pH3), and extracted with ethyl acetate (200 ml×4) while salting out with the addition of sodium chloride. The ethyl acetate layer is dried over MgSO₄ and concentrated to dryness in vacuo. Trituration of the residue with the addition of n-hexane affords the carboxylic acid [34a] (37.5 g, 98%) as a white solid.

To a solution of the above product [34a] (18.8 g, 76 mmol) and N-methylmorpholine (7.8 g, 77.1 mmol, 1.0 eq) in ethyl ether (200 ml) is added isobutyl chlorocarbonate (9.92 ml, 76.5 mmol, 1.0 eq) over 10 minutes at temperature between −15° C. and −10° C. under nitrogen atmosphere, and the mixture is stirred at the same temperature for 30 minutes. Precipitated methylmorpholine hydrochloride is filtered off, and the filtrate is added to a solution of diazomethane in ethyl ether which has previously been prepared from nitrosomethylurea (37 g, 359 mmol) with stirring at −10° C. over 5 minutes. After 2.5-hour stirring at room temperature, the mixture is concentrated in vacuo to remove excessive diazomethane. To the mixture is added ethyl acetate (150 ml) and then dropwise added 2N HCl/ethyl acetate (45 ml) at temperature between −40° C. and −30° C. After 30-minute stirring, the mixture is neutralized with saturated aqueous sodium bicarbonate. The ethyl acetate layer is separated, dried over MgSO₄, evaporated to dryness in vacuo, and subjected to silica gel chromatography (SiO₂: 150 g AcOEt:CH₂Cl₂=6:1) to obtain the chloromethyl ketone [36a] (20.3 g, 95%) as an oil.

To a solution of the above compound [36a] (40.3 g, 144.1 mmol) in MeCN (160 ml) are added CaCO₃ (28 g, 280 mmol, 1.9 eq) and thioformamide (HCSNH₂, 14 g, 229.1 mmol, 1.6 eq) and the mixture is stirred at room temperature for 18 hours under nitrogen atmosphere. Insoluble materials are filtered off and the filtrate is concentrated to dryness in vacuo. The residue is dissolved in dichloromethane, subsequently washed with 7% aqueous sodium bicarbonate, 1N NaOH, and water, two times each, to remove non-reacted thioformamide. The dichloromethane layer is dried over MgSO₄, concentrated to dryness in vacuo, and subjected to silica gel chromatography (SiO₂: 370 g, MeCN:CH₂Cl₂=1:7) to obtain (4-thiazolyl)alanine derivative [37a] (29.15 g, 71%) as an oil.

To the solution of above product [37a] (29.1 g, 101.6 mmol) in methanol(120 ml) is added 1N LiOH (112 ml, 112 mmol, 1.1 eq) with stirring and ice-cooling and the mixture is stirred for ten minutes at the same temperature and allowed to react for additional one hour at room temperature. The reaction mixture is concentrated in vacuo on a water bath below 30° C. to remove methanol and the residue is washed three times with dichloromethane. The aqueous layer is treated with active carbon, added with citric acid to adjust the pH to 3, and extracted with ethyl acetate (150 ml×3). To the organic layer washed two times with saturated aqueous sodium chloride are added MgSO₄ and active carbon, the mixture is filtered and the filtrate is concentrated to dryness in vacuo to obtain crystalline crude product [8b] (26.96 g, 97%). Recrystallization of the product from n-hexane provides pure product [8b] (26.2 g, 95%). m.p. 96°–98° C.

[α]_D= −4.2° (c=2; MeOH; 24° C.).

NMR (δ): 1.47(9H,s), 3.41(1H,dd,J=5.6,14.6Hz), 3.56(1H,dd,J=3.4,11.0Hz), 4.59(1H,m), 3.60(1H,d,J=3.6Hz), 7.14(1H,d,J=2Hz), 8.94(1H,d,J=2Hz).

b)

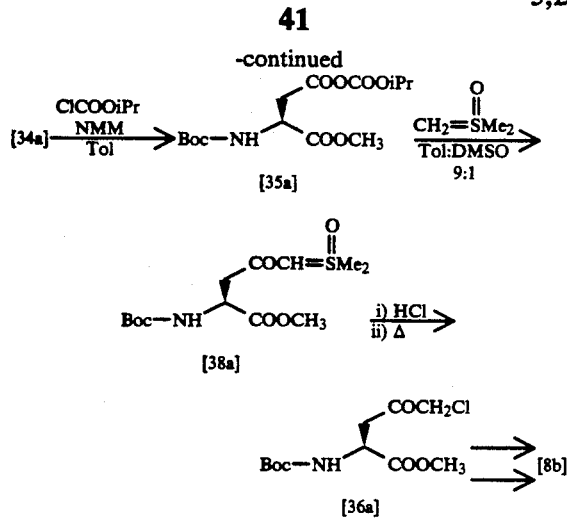

i) Preparation of carbonic anhydride

To a solution of compound [34a] (500 mg, 2.02 mmol) and N-methylmorpholine (225 mg, 2.22 mmol, 1.1 eq) in toluene (4 ml) is added isopropyl chlorocarbonate (0.254 ml, 2.22 mmol, 1.1 eq) with stirring at temperature between −15° C. and −10° C. under nitrogen atmosphere and the mixture is stirred at the same temperature for one hour to separate out N-methylmorpholine hydrochloride.

ii) Preparation of Corey reagent (dimethylsulfoxonium methylide)

To a suspension of trimethylsulfoxonium iodide (1.024 g, 4.65 mmol) in toluene (9 ml) and DMSO (1 ml) is added potassium t-butoxide (522 mg, 4.65 mmol, 1.0 eq) with stirring under nitrogen atmosphere, and the mixture is heated with stirring on an oil bath of 70°-75° C. for 30 minutes. Orange crystals turns to grayish white crystals.

The carbonic anhydride solution obtained in the above step i) is charged in a dropping funnel with a cotton stopper. The solution is dropwise added to the Corey reagent prepared in the step ii) from the funnel with stirring and ice-cooling under nitrogen atmosphere over 10 minutes and the mixture is stirred at room temperature for one hour. The mixture is filtered and the filtrate is extracted with water (10 ml×3). The aqueous layer is extracted with dichloromethane (10 ml×4). Each extract is washed with water, dried over MgSO4, and concentrated to dryness in vacuo to obtain 600 mg of crude product. Chromatography (SiO2: 40 g, 3.5% MeOH/CH2Cl2) of the crude product gives the aimed ylide compound [38a] (554 mg, 85%) as an oil.

To a solution of the ylide [38a] (3.16 g, 9.83 mmol) in dichloroethane (26 ml) is added 2N HCl/ethyl acetate (4.92 ml, 9.84 mmol) with stirring at −10° C. and the mixture is stirred for one hour. The mixture is warmed on an oil bath of 100° C. Although precipitates (HCl addition product) separate out after two minutes, they redissolve after 3.5 minutes. When the solution becomes turbid after 6 minutes, the solution is cooled immediately to terminate the reaction and the reaction mixture is subjected to silica gel chromatography (SiO2: 15 g, AcOEt:CH2Cl2=1:7) to obtain chloromethyl ketone [36a] (2.308 g, 84%) as a crystal substance.

A suspension of the above product [36a] (2.308 g, 8.25 mmol), HCSNH2 (1.26 g, 20.62 mmol, 2.5 eq) and CaCO3 (2.475 g, 24.75 mmol, 3 eq) in dichloroethane (23 ml), is stirred at room temperature for 15 hours under nitrogen atmosphere. After addition of NaI (62 mg, 0.414 mmol, 0.05 eq), the mixture is stirred for additional two hours. Insoluble materials are filtered off and washed with dichloromethane. The filtrate and washings are combined and subsequently washed with saturated aqueous sodium bicarbonate, 1N NaOH, and H2O (×2). Chromatographic treatment of the solution in the same manner as described in the foregoing process a) provides (4-thiazolyl)-L-alanine derivative [37a] (1.878 g, 80%) as an oil.

To a solution of the above compound [37a] (3.16 g, 11.04 mmol) in methanol (6 ml) is added with stirring and ice-cooling 1N LiOH (13 ml, 13 mmol, 1.18 eq) and the mixture is stirred at room temperature for one hour. Similar procedure as disclosed in the process a) provides crude product [8b] (2.9 g, 97%). Recrystallization of the product from ethyl ether/n-hexane gives pure product [8b] (2.6 g, 88%) as colorless crystals. m.p. 110°-112° C. [α]$_D$= −4.8 (c=2.0; MeOH; 25° C.)

PREPARATION 60 AND 61

N-sulfamylamino acids [12] listed in Table 4 are prepared from the compounds [30] in the same manner as disclosed in Preparation 58.

PREPARATION 62 AND 63

2-Substituted (4-thiazolyl)-L-alanines [8] listed in Table 5 are prepared from the compounds [36] in the same manner as disclosed in Preparation 59.

TABLE 4

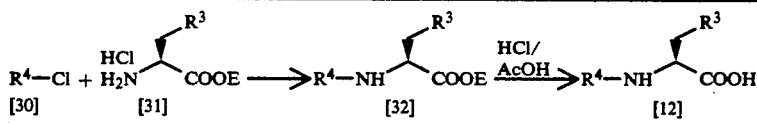

| Compd. of Prep. No. | R$^4$ | R$^3$ | E | [32] Yield % | Yield % | [α]$_D$° C = 1, MeOH (Temp. °C.) | IRν$_{max}$$^{CHCl_3}$ cm$^{-1}$ | NMR(δ) |
|---|---|---|---|---|---|---|---|---|
| 60 | O⟨NSO$_2$−⟩ | (naphthyl) | Me | 88 | 76 | −56.7(25) | 3480, 3340, 3200~2400, 1723(1750), 1598, 1508, 1450, 1395, 1342, 1155, 1111, 1070, 848 | 2.55(2H, m), 2.63(2H, m), 3.13(2H, m), 3.20(3H, m), 3.55(1H, bs), 3.80(1H, dd, J=4.6, 14Hz), 4.35(1H, dt, J=4.4, 10Hz), 5.05(1H, d, J=10.2Hz), 7.37(2H, m), 7.57(2H, m), 7.89(2H, m), 8.10(1H, d, J=8.2Hz) |

TABLE 4-continued $$R^4-Cl + \underset{[30]}{\overset{HCl}{H_2N}}\underset{[31]}{\overset{R^3}{\underset{|}{C}}COOE} \longrightarrow \underset{[32]}{R^4-NH\overset{R^3}{\underset{|}{C}}COOE} \xrightarrow{HCl/AcOH} \underset{[12]}{R^4-NH\overset{R^3}{\underset{|}{C}}COOH}$$

| Compd. of Prep. No. | $R^4$ | $R^3$ | E | [32] Yield % | [10] Yield % | $[\alpha]_D$ C = 1, MeOH (Temp. °C.) | $IR\nu_{max}^{CHCl_3}$ cm$^{-1}$ | NMR($\delta$) |
|---|---|---|---|---|---|---|---|---|
| 61 | Me₂N-SO₂— (Me)₂NSO₂- | phenyl | Et | 82 | 26 | | | 2.58(6H, s), 2.98(1H, dd, J=7.8, 13.6Hz), 3.20(1H, dd, J=5.2, 13.6Hz), 4.24(1H, dofdd, J=9.6, 7.4, 4.6Hz), 4.90(1H, d, J=10Hz), 4.90(1H, bs), 7.30(5H, m) |

TABLE 5

$$\underset{[36]}{Boc-NH\overset{}{\underset{|}{C}}COOCH_3}\overset{O}{\underset{}{\overset{||}{C}}}\underset{}{CH_2Cl} \xrightarrow{M-CSNH_2} \underset{[37]}{Boc-NH\overset{}{\underset{|}{C}}COOCH_3 \cdot \overset{S}{\underset{N_3}{\underset{|}{C}}}M} \longrightarrow \underset{[8]}{Boc-NH\overset{}{\underset{|}{C}}COOH \cdot \overset{S}{\underset{N}{\underset{|}{C}}}M}$$

| Compd. of Prep. No. | M | [37] Yield % | $[\alpha]_D$ C = 1, MeOH (temp. °C.) | [8] Yield % | mp. (°C.) | $[\alpha]_D$ C = 1, MeOH (temp. °C.) | $IR\nu_{max}^{CHCl_3}$cm$^{-1}$ | NMR($\delta$) |
|---|---|---|---|---|---|---|---|---|
| 62 | CH₃ | 42 | — | 93 | 135–136 | (C = 2) −20.4 (24) | 3430, 2440(br) 1700, 1495, 1435, 1392 1368, 1160 1060 | |
| 63 | NH₂ | 88 | −345 (24) −10.1* (22) | * 87 | * 156–157 | * −4.3 (22) | *3440, 3200, 2440(br) 1700, 1565, 1500 1455, 1435, 1392 1370, 1160 1062 | *1.50(9H, s), 3.38(2H, m), 4.64 (1H, m), 5.15(2H, d, J=6.8Hz), 6.69(1H, s), 8.48(1H, s) |

*formyl compound

PREPARATION 64

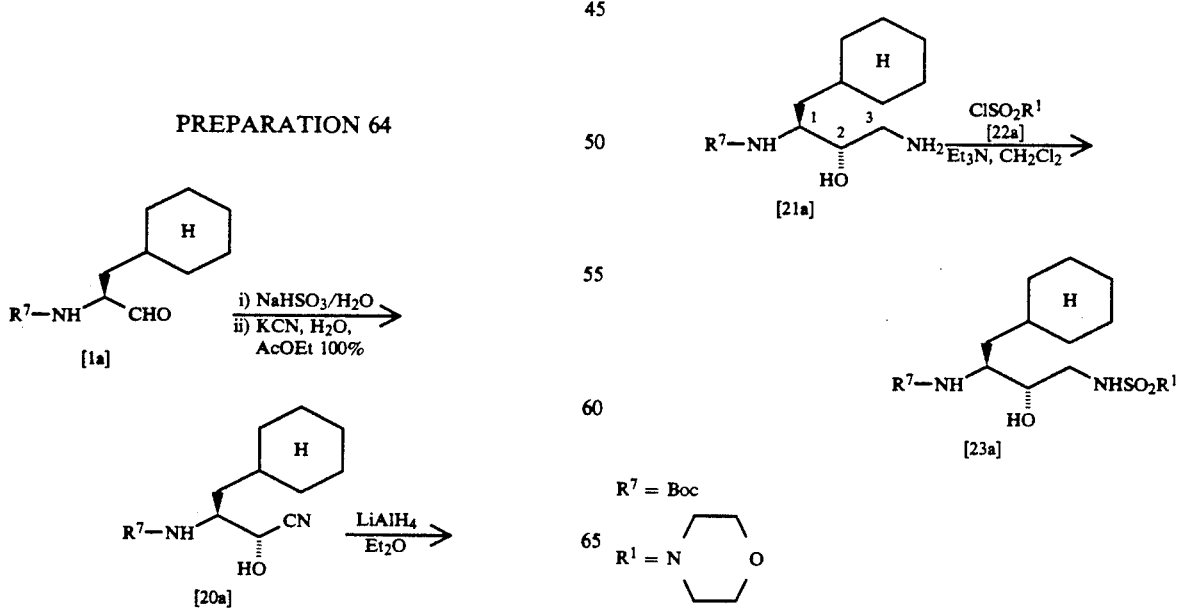

$R^7 = Boc$ $R^1 = $ N-morpholino

To the aldehyde compound [1a] (10.08 g, 39.5 mmol) is added NaHSO$_3$ (10.08 g) in water (70 ml) and the mixture is stirred with ice-cooling for 16 hours. The resultant solution is stirred at room temperature for 4 hours after addition of KCN (6.3 g) in water (16.8 ml) and ethyl acetate (137 ml). The ethyl acetate layer is separated from the reaction mixture, washed with saturated aqueous sodium chloride, dried, and concentrated. The residue is subjected to a column chromatography using Lobar column Size C (CH$_2$Cl$_2$:acetone=19:1). Resultant product is recrystallized from hexane to give the aimed product [20a] (6.51 g, 58%).

The product [20a] (3.56 g, 12.6 mmol) in anhydrous THF (50 ml) is added dropwise a suspension of LiAlH$_4$ (574 mg, 1.2 mol) in anhydrous THF (30 ml) with stirring and ice-cooling to over 30 minutes. The mixture is stirred at 0° C. for additional one hour. A small amount of ethyl acetate and ice water are added to the mixture to separate out inorganic materials. The insoluble materials are filtered, and the filtrate is concentrated in vacuo and then purified with silica gel chromatography (SiO$_2$: 120 g, CH$_2$Cl$_2$:MeOH:NH$_4$OH=80:20:2). The aimed compound [21a] (2.21 g, 61%) is thus obtained.

To a solution of the compound [21a] (12.49 g, 43.6 mmol) in anhydrous dichloromethane (200 ml) are added triethylamine (8.8 g, 2.0 eq) and morpholinosulfonyl chloride (10.1 g, 1.25 eq) and the mixture is stirred at room temperature for 3 hours and concentrated in vacuo. The residue is dissolved in ethyl acetate, washed with water, dried, and evaporate to remove the solvent. The residue is purified with silica gel chromatography (SiO$_2$: 200 g, CH$_2$Cl$_2$:MeOH:NH$_4$OH=90:10:1). The aimed compound [23a] (18.16 g, 95%) is thus obtained.

NMR($\delta$): 0.70–1.85(13H,m), 1.45(9H,s), 3.02(1H,m), 3.18(5H,m), 3.72(6H,m), 4.62(1H,d,J=9.2Hz), 5.58(1H,bt).

PREPARATION 65-74

The compounds [23] listed in Table 6 are prepared in the manner as taught in Preparation 64.

TABLE 6

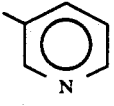

| Compd. of Prep. No. | R$^1$ | yield % | NMR($\delta$) |
|---|---|---|---|
| 65 | —NMe$_2$ | 97 | 0.80~1.90(13H, m), 1.45(9H, s), 2.80(6H, s), 3.08(2H, m), 3.72(2H, m), 4.63(1H, d, J=9.2Hz), 5.48(1H, m) |
| 66 | 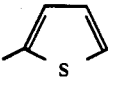 | 90 | 0.70~1.80(13H, m), 1.37(9H, s), 2.49(1H, bs), 2.82(1H, dt, J=6.2, 13.5Hz), 3.12(1H, dt, J=7, 13Hz), 3.68(2H, m), 4.60(1H, d, J=9.3Hz), 4.47(1H, dd, J=4.6Hz), 8.17(1H, m), 8.79(1H, bd), 9.08(1H, bs) |
| 67 | 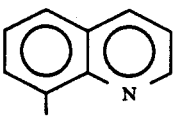 | 93 | 0.70~1.85(13H, m), 1.39(9H, s), 2.90(1H, dt, J=6.1, 13.4Hz), 3.16(1H, dt, J=7.0, 12.9Hz), 2.60(1H, m), 3.67(2H, m), 4.57(1H, d, J=9.2), 5.89(1H, t, J=7Hz), 7.07(1H, dd, J=3.7, 5.0Hz), 7.60(2H, m), 6.24(1H, bt) |
| 68 | 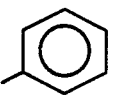 | 99 | 0.65~1.80(13H, m), 1.32(9H, s), 2.89(2H, bt), 3.55(1H, m), 3.66(1H, m), 4.58(1H, d, J=9.2Hz), 6.80(1H, bt), 7.57(1H, dd, J=4.4, 8.4Hz), 7.66(1H, t, J=7.4Hz), 8.07 (1H, dd, J=1.0, 8.2Hz), 8.29(1H, dd, J=1.6, 8.4Hz), 8.42(1H, dd, J=1.4, 7.4Hz) 9.05(1H, dd, J=1.6, 4.4Hz) |
| 69 | 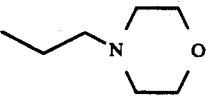 | 97 | 0.70~1.80(13H, m), 1.37(9H, s), 2.58(1H, bd, J=5Hz), 2.80(1H, dt, J=6.2, 13.6Hz), 3.08(1H, dt, J=6.5, 13.6Hz), 3.65(2H, m), 4.56(1H, d, J=9.2Hz), 5.82(1H, bt, J=6Hz), 7.53(3H, m), 7.85(2H, m) |
| 70 | 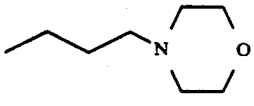 | 72 | 0.75~1.87(13H, m), 1.45(9H, s), 1.98(1H, bs), 2.52(4H, m), 2.86(2H, m), 3.17(4H, m), 3.73(6H, m), 4.62(1H, d, J=9.4Hz), 5.63(1H, bt) |
| 71 | 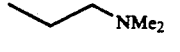 | 36 | 0.75~1.88(13H, m), 1.45(9H, s), 2.03(2H, m), 2.49(6H, m), 3.13(4H, m), 3.72(6H, m), 4.65(1H, d, J=9.1Hz), 5.82(1H, bt) |
| 72 | ~~NMe$_2$ | 75 | 0.75~1.90(13H, m), 1.44(9H, s), 2.29(6H, s), 2.80(2H, m), 3.16(5H, m), 3.64(2H, m), 4.66(1H, d, J=9.6Hz) |

TABLE 6-continued

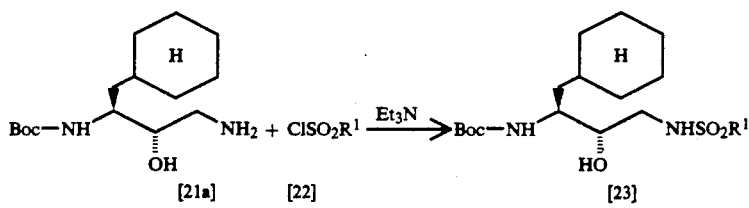

| Compd. of Prep. No. | R¹ | yield % | [23] NMR(δ) |
|---|---|---|---|
| 73 | Me | 97 | 0.75~1.85(13H, m), 1.45(9H, s), 2.85(1H, bs), 2.96(3H, s), 3.14(2H, m), 3.72(2H, m), 4.65(1H, d, J=9.4Hz), 5.53(1H, bt) |
| 74 | ~~~ | 98 | 0.94(3H, t, J=7.2Hz), 0.80~1.95(17H, m), 1.45(9H, s), 2.76(1H, bs), 3.00(2H, m), 3.16(2H, m), 3.70(2H, m), 4.63(1H, d, J=9Hz), 5.44(1H, t, J=7Hz) |

PREPARATION 75

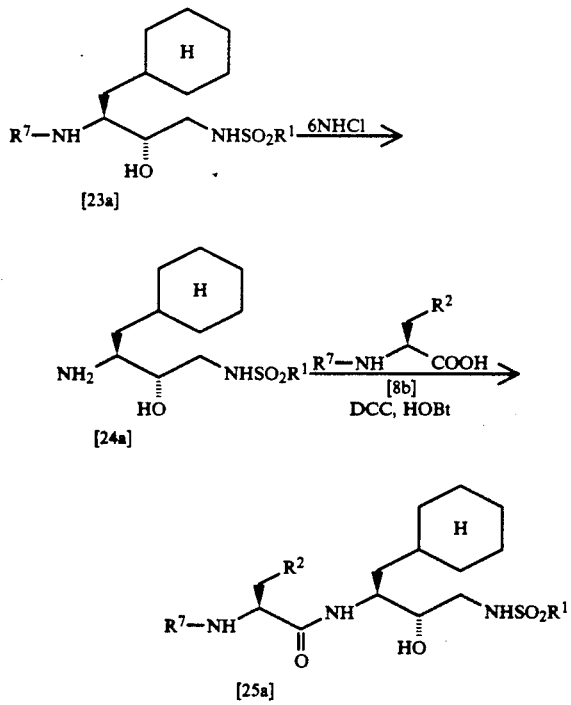

R⁷ = Boc

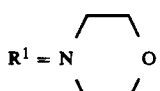

R¹ = N O (morpholine ring)

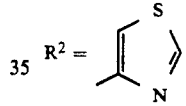

-continued

A mixture of the compound [23a] (18.16 g, 41.6 mmol), THF (150 ml), and 6N HCl (150 ml) is stirred at room temperature for 4 hours. The reaction mixture is made alkaline with Na₂CO₃ and saturated aqueous NaHCO₃ and extracted with a mixture of dichloromethane and methanol (9:1). The organic layer is dried and evaporated to dryness in vacuo. The residue is subjected to silica gel column chromatography (SiO₂: 100 g, CH₂Cl₂:MeOH:NH₄OH=80:20:2). The compound [24a] (14.0 g, quantitative amount) is thus obtained.

To a solution of the above compound [24a] (14.0 g, 41.6 mmol) in acetonitrile (200 ml) are added 4-thiazolyl-L-alanine [8b] (12.09 g, 1.1 eq) and HOBt (7.04 g, 1.25 eq) with ice-cooling. To the mixture is added DCC (11.18 g, 1.3 eq) and the resulting mixture is stirred for one hour at 0° C. and one hour at room temperature. The reaction mixture is filtered after addition of ethyl acetate and the filtrate is concentrated in vacuo. The residue is subjected to silica gel column chromatography (SiO₂: 600 g, CH₂Cl₂:MeOH:NH₄OH=90:10:1) to give the product [25a] (24.5 g, quantitative amount).

NMR(δ): 0.70–1.80(13H,m), 1.45(9H,s), 2.45(1H,bs), 2.98(2H,m), 3.18(4H,m), 3.30(2H,m), 3.75(5H,m), 4.02(1H,m), 4.46(1H,ddd,J=6.4H×3), 5.72(1H,bt,J=6.6Hz), 6.16(1H,d,J=6.4Hz), 6.36(1H,d,J=9.2Hz), 7.15(1H,d,J=1.8Hz), 8.82(1H,d,J=2Hz).

PREPARATION 76–86

Compounds [25] listed in Table 7 are prepared according to the procedure disclosed in Preparation 75.

TABLE 7

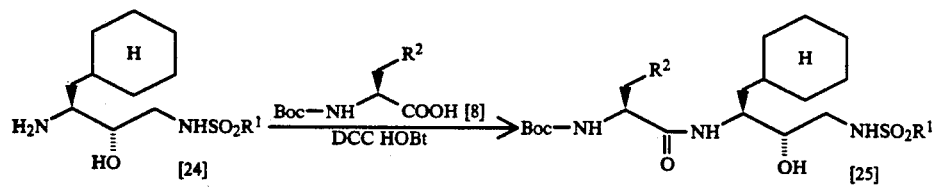

| Compd. of Prep. No. | R[1] | R[2] | [25] Yield % | NMR (δ) |
|---|---|---|---|---|
| 76 | —NMe$_2$ | (3-methyl-but-2-enyl thiazole) | 90 | 0.70~1.80(13H, m), 1.45(9H, s), 2.79(6H, s), 2.95(2H, m), 3.29(2H, m), 3.73(1H, m), 4.01(1H, m), 4.48(1H, ddd, J=6.6Hz), 5.58(1H, bt), 6.15(1H, d, J=7Hz), 6.39(1H, d, J=10Hz), 7.15(1H, d, J=1.8Hz), 8.82(1H, d, J=2Hz) |
| 77 | (3-pyridyl) | (3-methyl-but-2-enyl thiazole) | 94 | 0.65~1.75(13H, m), 1.39(9H, s), 2.80(1H, dt, J=6.4, 13.6Hz), 3.00(1H, dt, J=6.6, 13.7Hz), 3.19(2H, d, J=5.6Hz), 3.70(1H, dt, J=2.3, 6.7Hz), 3.99(1H, m), 4.46(1H, ddd, J=6Hz), 6.05(1H, d, J=6.3Hz), 6.55(2H, m), 7.11(1H, d, J=1.8Hz), 7.45(1H, m), 7.80(1H, dd, J=4, 24Hz), 8.20(1H, d, J=7Hz), 8.77(1H, d, J=2Hz), 9.08(1H, bs) |
| 78 | (2-thienyl) | (3-methyl-but-2-enyl thiazole) | 99 | 0.65~2.00(13H, m), 1.43(9H, s), 2.81(1H, dt, J=6.3, 13.5Hz), 2.99(1H, dt, J=6.9, 13.5Hz), 3.24(2H, m), 3.66(1H, dd, J=2.4, 6.8Hz), 3.97(1H, m), 4.45(1H, ddd, J=6.5Hz×3), 6.02(1H, d, J=6.9Hz), 6.22(1H, bt), 6.39(1H, d, J=9.3Hz), 7.10(2H, m), 7.58(2H, m), 8.75(1H, d, J=1.8Hz) |
| 79 | (8-quinolyl) | (3-methyl-but-2-enyl thiazole) | 96 | 0.55(13H, m), 1.43(9H, s), 2.79(2H, m), 3.11(1H, dd, J=5.7, 14.7Hz), 3.22(1H, dd, J=5.4, 14.7Hz), 3.65(1H, m), 3.84(1H, m), 4.32(1H, ddd, J=6.6Hz×3), 6.09(1H, d, J=6Hz), 6.27(1H, d, J=9.4Hz), 6.78(1H, t, J=6.2Hz), 7.02(1H, d, J=1.8Hz), 7.56(1H, dd, J=4.3, 8.4Hz), 7.65(1H, t, J=7.4Hz), 8.06(1H, dd, J=1.4, 8.3Hz), 8.27(1H, dd, J=1.8, 8.4Hz), 8.41(1H, dd, J=1.4, 7.3Hz), 8.69(1H, d, J=1.9Hz), 9.04(1H, dd, J=1.7, 4.2Hz) |
| 80 | (phenyl) | (3-methyl-but-2-enyl thiazole) | 99 | 0.67~2.00(13H, m), 1.43(9H, s), 2.74(1H, dt, J=6.9, 13.5Hz), 2.94(1H, dt, J=6.8, 13.5Hz), 3.18(1H, dd, J=6.3, 14Hz), 3.27(1H, dd, J=5.7, 14Hz), 3.62(1H, dt, J=2.6, 6.8Hz), 3.95(1H, m), 4.41(1H, ddd, J=6.6Hz×3), 5.95(1H, bt), 6.05(1H, d, J=6.8), 6.29(1H, d, J=9.3Hz), 7.07(1H, d, J=1.9Hz), 7.52(3H, m), 7.86(2H, m), 8.73(1H, d, J=2.0Hz) |
| 81 | (2-morpholinoethyl) | (3-methyl-but-2-enyl thiazole) | 99 | 0.63~1.78(13H, m), 1.45(9H, s), 2.14(1H, bs), 2.52(4H, bt, J=4.6Hz), 2.86(2H, t, J=7Hz), 3.05(2H, bt, J=6Hz), 3.14~3.40(4H, m), 3.66(1H, m), 3.73(4H, m), 4.00(1H, m), 4.42(1H, ddd, J=6.2Hz), 5.80(1H, bt), 6.24(1H, d, J=6.6Hz), 6.31(1H, d, J=9.4Hz), 7.14(1H, d, J=2Hz), 8.81(1H, d, J=2Hz) |
| 82 | (3-morpholinopropyl) | (3-methyl-but-2-enyl thiazole) | 99 | 0.70~1.80(13H, m), 1.45(9H, s), 2.01(2H, m), 2.49(6H, m), 3.08(4H, m), 3.30(2H, m), 3.72(5H, m), 4.00(1H, m), 4.43(1H, ddd, J=6.6Hz×3), 5.88(1H, bt), 6.24(1H, d, J=6.6Hz), 6.52(1H, d, J=9.6Hz), 7.15(1H, d, J=1.8Hz), 8.82(1H, d, J=1.8Hz) |
| 83 | (2-dimethylaminoethyl) | (3-methyl-but-2-enyl thiazole) | 77 | 0.60~1.80(13H, m), 1.45(9H, s), 2.29(6H, s), 2.81(2H, t, J=6.2Hz), 3.04(2H, d, J=6.6Hz), 3.18(2H, m), 3.25(1H, dd, J=5.6, 14.6Hz), 3.34(1H, dd, J=5.4, 14.6Hz), 3.65(1H, dt, J=2.4, 6.2Hz), 3.98(1H, m), 4.45(1H, ddd, J=6.6Hz), 6.22(1H, d, J=6.6Hz), 6.40(1H, d, J=9.6Hz), 7.14(1H, d, J=2Hz), 8.81(1H, d, J=2Hz) |
| 84 | Me | (3-methyl-but-2-enyl thiazole) | 75 | 0.70~1.80(13H, m), 1.45(9H, s), 2.96(6H, s), 3.03(2H, m), 3.30(2H, m), 3.70(1H, m), 4.02(1H, m), 4.46(1H, ddd, J=6.6Hz×3), 5.72(1H, bt), 6.21(1H, d, J=6.6Hz), 6.39(1H, d, J=9.6Hz), 7.15(1H, d, J=1.6Hz), 8.82(1H, d, J=1.8Hz) |
| 85 | (n-propyl) | (3-methyl-but-2-enyl thiazole) | 83 | 0.95(3H, t, J=7.2Hz), 0.65~1.88(17H, m), 1.45(9H, s), 3.00(5H, m), 3.30(2H, m), 3.68(1H, dt, J=2.3, 6.6Hz), 4.01(1H, m), 4.45(1H, ddd, J=6.2Hz×3), 5.56(1H, bt), 6.18(1H, d, J=6.6Hz) 6.35(1H, d, J=9.6Hz), 7.14(1H, d, J=1.8Hz), 8.81(1H, d, J=2.0Hz) |

TABLE 7-continued

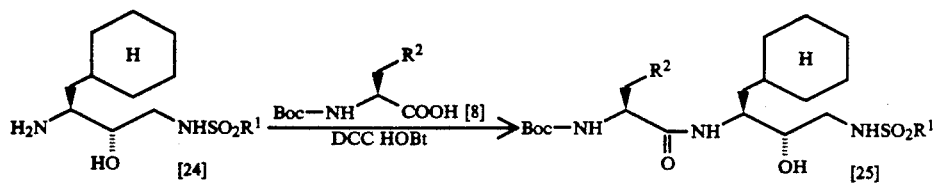

| Compd. of Prep. No. | R[1] | R[2] | [25] Yield % | NMR (δ) |
|---|---|---|---|---|
| 86 | (phenyl with Me) | (thiazolyl-methylidene with Me) | 99 | 0.65~1.75(13H, m), 1.43(9H, s), 2.64(3H, s), 2.74(1H, dt, J=6.3, 13.6Hz), 2.96(1H, dt, J=6.8, 13.4Hz), 3.10(2H, m), 3.61(1H, dt, J=3, 6.6Hz), 3.96(1H, m), 4.34(1H, ddd, J=5.8Hz), 5.90(1H, m), 6.00(1H, d, J=6.2Hz), 6.32(1H, d, J=9.2Hz), 6.82(1H, s), 7.52(3H, m), 7.86(2H, dd, J=1.6, 7.8Hz) |

EXAMPLE 1

3-t-Butylsulfonyl-2(S)-phenylmethylpropionyl-His-1(S)-cyclohexylmethyl-2(S)-hydroxy-4-oxo-4-(4-pyridyl)butylamide [1a]

1) His(Ts)-1(S)-cyclohexylmethyl-2(S)-hydroxy-4-oxo-4-(4-pyridyl)butylamide [11a]

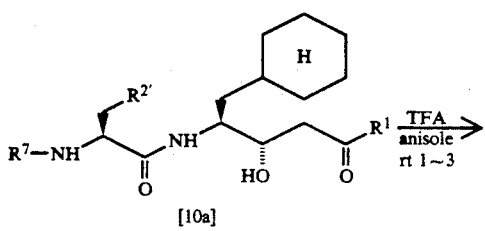

R[1] = 4-pyridyl
R[1] = 4-pyridyl
R[2'] = 4-tosylimidazolyl
R[7]: Boc

Boc-His(Ts) 1(S)-cyclohexylmethyl-2(S), hydroxy-4-oxo-4-(4-pyridyl)butylamide [10a] (1.31 g, 1.96 mmol) prepared in Preparation 21 is dissolved in anisole (13 ml). To the solution is added trifluoroacetic acid (13 ml) with stirring and ice-cooling and the mixture is stirred at room temperature for one hour. After evaporation of the reaction mixture to dryness in vacuo, ice is added to the residue and the mixture is washed with ethyl ether. The aqueous layer neutralized with 3N NaOH and adjusted to pH8 by addition of powdered $Na_2CO_3$ is extracted with dichloromethane three times and finally extracted with a mixture of dichloromethane and methanol (10:1). The organic layer is washed with saturated aqueous sodium chloride, dried over $MgSO_4$ and evaporated to dryness in vacuo. The residue is purified with silica gel chromatography ($CH_2Cl_2$:MeOH=95:5) to obtain the aimed crude product (850 mg, 73%). Recrystallization of the crude product from ethyl acetate provides the title compound [11a] (750 mg, 65%) as a needle crystal. m.p. 161°–162° C.

NMR(δ): 0.75–1.80(13H,m), 1.98(1H,br.s), 2.44(3H,s), 2.73(1H,dd,J=14.8,8.2Hz), 2.95–3.24(3H,m), 3.65(1H,dd,J=8.4,4.2Hz), 4.02(1H,m), 4.27(1H,m), 7.12(1H,d,J=1.2Hz), 7.36(2H,d,J=7.8Hz), 7.53(1H,d,J=10Hz), 7.70(2H,m), 7.81(2H,d,J=8.4Hz), 7.92(1H,d,J=1.4Hz), 8.79(2H,m).

IR νmax($CHCl_3$)cm$^{-1}$: 3680, 3340, 1690, 1654, 1602, 1593, 1515, 1475, 1450.

Elemental analysis(as $C_{29}H_{39}N_5O_6S$); Calcd.: C:59.01; H:6.75; N:11.87; S:5.43; Found : C:59.12; H:6.69; N:11.68; S:5.21.

2) 3-t-Butylsulfonyl-2(S)-phenylmethylpropionyl-His(Ts) 1(S)-cyclohexylmethyl-2(S)-hydroxy-4-oxo-4-(4-pyridyl)butylamide [13a]

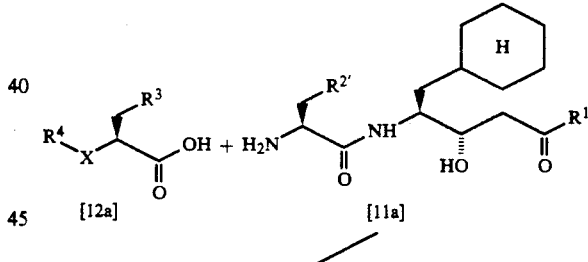

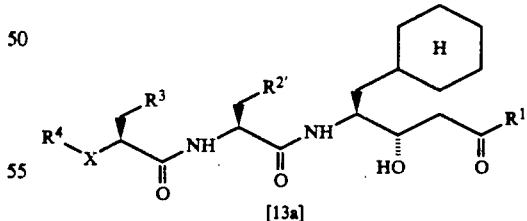

R[4] = t-butylsulfonyl
R[3] = phenyl
X = $CH_2$
R[1] = 4-pyridyl
R[2'] = 1-tosyl-4-imidazolyl To a solution of the ketone compound [11a] (334 mg, 0.57 mmol) in dichloromethane (1 ml) are added 3-t-butylsulfonyl-2(S)-phenylmethylpropionic acid (220 mg, 0.76 mmol, 1.3 eq), N-methylmorpholine (77 mg, 0.76 mmol, 1.3 eq), and then DEPC (124 mg, 0.76 mmol, 1.3 eq) and the mixture is stirred at room temperature for four hours. The reaction mixture is evaporated to dryness in vacuo and subjected to silica gel chromatography (CH$_2$Cl$_2$:MeOH=95:5) to obtain the title compound [13a] (418 mg, 89%) as colorless powders.

NMRδ: 0.70-2.10(14H,m), 1.33(9H,s), 2.43(3H,s), 2.70-3.28(8H,m), 3.45(1H,dd,J=12.9,9.4Hz), 4.00(1H,m), 4.18(1H,m), 4.53(1H,ddd,J=5.8,5.8,5.8Hz), 6.34(1H,d,J=10Hz), 7.17(1H,d,J=1.2Hz), 7.22(5H,m), 7.34(2H,d,J=8.4Hz), 7.81(2H,d,J=8.5Hz), 7.85(1H,d,J=1.2Hz), 7.75(2H,d,J=6.0Hz), 8.81(2H,d,J=5.9Hz).

IR νmax(CHCl$_3$) cm$^{-1}$:3680, 3470, 3370, 1665, 1600, 1520, 1450, 1172, 1112, 1075.

3) 3-t-Butylsulfonyl-2(S)-phenylmethylpropionyl-His 1(S)-cyclohexylmethyl-2(S)-hydroxy-4-oxo-4-(4-pyridyl)butylamide [Ia]

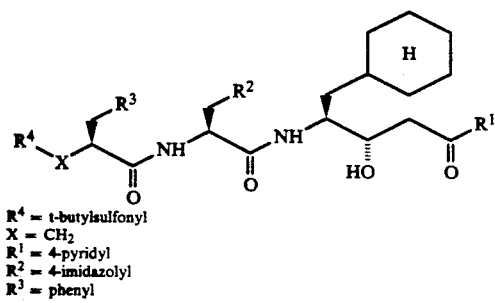

[Ia]

R$^4$ = t-butylsulfonyl
X = CH$_2$
R$^1$ = 4-pyridyl
R$^2$ = 4-imidazolyl
R$^3$ = phenyl To a solution of the protected compound [13a] (740 mg, 0.89 mmol) obtained in the above step 2) in DMF (4 ml) is added pyridinium hydrochloride (1030 mg, 8.87 mmol, 10.0 eq) and the mixture is stirred at room temperature for two hours. The reaction mixture is adjusted to pH 7-8 by addition of ice and 4% aqueous NaHCO$_3$ and extracted three times with dichloromethane. The organic layer is washed with saturated aqueous sodium chloride, dried over MgMgSO$_4$, and concentrated to dryness in vacuo. The residue is purified with silica gel chromatography (CH$_2$Cl$_2$:MeOH:concNH$_4$OH=950:50:1) to obtain the title compound [Ia] (543 mg, 90%). Trituration of the residue with diisopropyl ether gives colorless powders.

NMRδ: 0.67-1.83(13H,m), 1.33(9H,s), 2.86(1H,d,J=13.5,8.4Hz), 2.97(1H,dd,J=13.0,9.8Hz), 3.10(5H,m), 3.26(1H,m), 3.56(1H,dd,J=13.0,9.8Hz), 4.02(1H,m), 4.20(1H,m), 4.56(1H,ddd,J=6.3,6.3,6.3Hz), 6.44(1H,d,J=10Hz), 6.90(1H,s), 7.24(4H,m), 7.48(1H,s), 7.46(1H,bs), 7.70(2H,m), 8.78(2H,m)

[α]$_D$=−22.5° (C=1.0; MeOH; 23° C.) IR νmax(CHCl$_3$)cm$^{-1}$:3460, 3360(br), 1662(1690sh), 1603, 1496, 1450, 1410, 1115.

Elemental analysis (as C$_{36}$H$_{49}$N$_5$O$_6$S.$\frac{3}{4}$H$_2$O); Calcd.: C:62.36; H:7.34; N:10.10; S:4.62; Found : C:62.42; H:7.33; N:10.21; S:4.49.

EXAMPLE 2-52

The same procedure as disclosed in the steps 1) and 2) in Example 1 is repeated using, as the starting material, the compounds [10] prepared in foregoing Preparations 21-58, and the compounds [11] and [13] listed in Tables 8 (compound [11]) and 9 (compound [13]) are obtained. The compounds [13] (for example, compound [13] of No. 23) wherein R$^1$ or R$^2$ is not protected correspond to the compounds (I) of the invention. Where the substituent R$^2$ is protected, the compounds [13] are deprotected according to the procedure as disclosed in Step 3) in Example 1 to obtain the final products (I), which are listed in the following Table 10.

TABLE 8

[10] → [11]

| Comp. of Ex. No. | R$^1$ | R$^2'$ | Yield % m.p. (°C.) | [α]$_D$°(C = 1.0, CHCl$_3$) (°C.) | I R νmax cm$^{-1}$ or NMR (δ) | Elemental analysis Calcd. | Found |
|---|---|---|---|---|---|---|---|
| 2 | phenyl | Ts-N(pyrrole) | 81<br>126-127 | −49.1<br>(23.5) | 3560, 3360, 1666, 1598, 1580, 1511, 1450, 1382, 1172, 1075 | C: 63.58<br>H: 6.76<br>N: 9.89<br>S: 5.66 | C: 63.34<br>H: 6.67<br>N: 9.84<br>S: 5.57 |
| 3 | o-fluoro-phenyl | Ts-N(pyrrole) | 67 | | 3600, 3460(br), 1670, 1610, 1598, 1510, 1480, 1450, 1383, 1170, 1075 | oil | |
| 4 | m-methoxy-phenyl | Ts-N(pyrrole) | 55 | | 0.70~1.83(13H, m), 2.05(3H, bs), 2.44(3H, s), 2.72(1H, dd, J=8, 16Hz), 2.98(1H, dd, J=10, 18Hz), 3.07(1H, dd, J=6, 16Hz), 3.18(1H, dd, J=3, 18Hz), 4.66(1H, dd, J=4, 8Hz), 3.85(3H, s), 4.02(1H, m), 4.24(1H, m), 7.17(1H, s), 7.17(1H, m), 7.30~7.60(3H, m), 7.35(2H, d, J=8.0Hz), 7.80(2H, d, J=8.4Hz), 7.91(1H, d, J=1.4Hz) | oil | |

TABLE 8-continued

| Ex. No. | R[1] | R[2'] | Yield % | [α]$_D$ (C = 1.0, CHCl$_3$) (°C.) | mp (°C.) | I R νmax cm$^{-1}$ or NMR (δ) | |
|---|---|---|---|---|---|---|---|
| 5 | p-methyl-phenyl | Ts-N (4-methylimidazolyl) | 43 | | | 3360, 1668, 1608, 1570, 1510, 1450, 1385, 1172, 1092, 1075 | oil |
| 6 | 2,4-difluoro-phenyl | Ts-N (4-methylimidazolyl) | 71 | −43.9 (23.5) | | 3580, 3360, 1665, 1612, 1595, 1510, 1498, 1475, 1383, 1172, 1075, 970 | C: 59.78  C: 59.53<br>H: 6.02  H: 6.04<br>N: 9.30  N: 9.42<br>S: 5.32  S: 5.56<br>F: 6.31  F: 6.38 |
| 7 | 1-naphthyl | Ts-N (4-methylimidazolyl) | 49 | | | 3400(br), 1665, 1559, 1575, 1510, 1450, 1386, 1190, 1174, 1094, 1080, 909 | oil |

| Compd. of Ex. No. | R[1] | R[2'] | Yield % | [α]$_D$ (C = 1.0, CHCl$_3$) (°C.) | mp (°C.) | I R νmax cm$^{-1}$ or NMR (δ) |
|---|---|---|---|---|---|---|
| 8 | 3-thienyl | Ts-N (4-methylimidazolyl) | 70 | | | 3680, 3360(br), 3120, 1665, 1598, 1510, 1475, 1450, 1382, 1172, 1076 |
| 9 | 2-thiazolyl | Ts-N (4-methylimidazolyl) | 52 | | | 0.73~1.83(13H, m), 2.33(2H, bs), 2.44(3H, s), 2.76(1H, dd, J=7, 15Hz), 3.07(1H, dd, J=3.6, 14.6Hz), 3.18~3.38(2H, m), 3.68(1H, m), 4.02(1H, m), 4.25(1H, m), 7.14(1H, s), 7.35(2H, d, J=8.0Hz), 7.51(1H, d, J=9.0Hz), 7.69(1H, d, J=3.0Hz), 7.80(2H, d, J=8.4Hz), 7.95(1H, d, J=1.2Hz), 8.01(1H, d, J=3.0Hz) |
| 10 | m-fluorophenyl | Ts-N (4-methylimidazolyl) | 66 | | | 3360, 1670, 1590, 1510, 1445, 1382, 1170, 1090, 1075 |
| 11 | p-fluorophenyl | Ts-N (4-methylimidazolyl) | 57 | −45.8 (24.0) | 128~130 | 3360, 3500(br), 1665, 1600, 1508, 1475, 1450, 1095, 1075 |
| 12 | 2,6-difluorophenyl | Ts-N (4-methylimidazolyl) | 53 | −23.9 (24.0) | | 3368, 1698, 1665, 1624, 1598, 1512, 1420, 1385, 1279, 1190, 1174, 1094, 1077, 1018 |

TABLE 8-continued

| | | | | [11] | |
|---|---|---|---|---|---|
| Compd. of Ex. No. | $R^1$ | $R^{2'}$ | Yield % | mp (°C.) | IR νmax cm$^{-1}$ or NMR (δ) |
| 13 | o-methoxyphenyl | Ts–N (pyrimidinylmethyl) | 25 | | 0.70~1.85(13H, m), 2.20(3H, bs), 2.44(3H, s), 2.74(1H, dd, J=8, 15Hz), 2.95(1H, dd, J=10, 17Hz), 3.10(1H, dd, J=15Hz), 3.26(1H, dd, J=17, 3Hz), 3.69(1H, dd, J=5, 10Hz), 3.88(3H, s), 3.99(1H, m), 4.18(1H, m), 6.98(2H, m), 7.12(1H, s), 7.35(2H, d, J=8Hz), 7.50(1H, m), 7.72(1H, dd, J=7.5, 2Hz), 7.81(2H, d, J=8Hz), 7.92 (1H, s) |
| 14 | o-chlorophenyl | Ts–N (pyrimidinylmethyl) | 75 | | 0.70~1.82(13H, m), 2.40(3H, s), 2.44(3H, s), 2.72(1H, dd, J=8, 15.8Hz), 3.00(1H, dd, J=17.5, 10Hz), 3.07(1H, dd, J=15.5Hz), 3.17(1H, dd, J=17.5, 4Hz), 3.65(1H, dd, J=10.5Hz), 3.98(1H, m), 4.23(1H, m), 7.11(1H, s), 7.25~7.58(6H, m), 7.81(2H, d, J=8.4Hz), 7.91(1H, d, J=1.4Hz) |
| 15 | m-cyanophenyl | Ts–N (pyrimidinylmethyl) | 79 | | 3360, 2236, 1666, 1514, 1498, 1450, 1386, 1189, 1174, 1094, 1078, 909 |
| 16 | o-methyl-sulfonyl-aminophenyl | Ts–N (pyrimidinylmethyl) | 38 | | 3368, 1657, 1607, 1578, 1496, 1452, 1386, 1340, 1189, 1173, 1094, 1078, 968, 909 |
| 17 | p-trifluoro-methylphenyl | Ts–N (pyrimidinylmethyl) | 53 | 113~115 | 3360, 1670, 1600, 1510, 1450, 1410, 1385, 1325, 1180, 1135, 1065 |

| | | | | [11] |
|---|---|---|---|---|
| Compd. of Ex. No. | $R^1$ | $R^{2'}$ | Yield % | NMR (δ) |
| 18 | m-morpholino-carbonyloxy-phenyl | Ts–N (pyrimidinylmethyl) | 81 | 0.73~2.20(13H, m), 2.44(3H, s), 2.75(1H, dd, J=14.8, 8.6Hz), 2.93~3.24(3H, m), 3.5~3.82(8H, m), 4.02(1H, m), 4.23(1H, m), 7.13(1H, d, J=1.0Hz), 7.35(2H, d, J=8.0Hz), 7.35(1H, m), 7.47(1H, t, J=7.5Hz), 7.60(1H, d, J=10Hz), 7.67(1H, m), 7.81(2H, d, J=8.4Hz), 7.81(1H, m), 7.91(1H, d, J=1.4Hz) |
| 19 | m-morpholino-carbonylphenyl | Ts–N (pyrimidinylmethyl) | 41 | 0.70~1.85(13H, m), 2.28(3H, bs), 2.44(3H, s), 2.75(1H, dd, J=8.6, 14.8Hz), 2.95~3.27(3H, m), 3.30~3.94(8H, m), 3.68(1H, dd, J=8.4, 4.2Hz), 4.02(1H, m), 4.26(1H, m), 7.14(1H, d, J=1.4Hz), 7.36(2H, d, J=8Hz), 7.47~7.69(2H, m), 7.81(2H, d, J=8.4Hz), 7.93(1H, d, J=1.2Hz), 7.98(1H, d, J=1.6Hz), 8.00(1H, m) |
| 20 | 3,4-methylene-dioxyphenyl | Ts–N (pyrimidinylmethyl) | 74 | 0.70~2.15(13H, m), 2.44(3H, s), 2.73(1H, dd, J=14.4, 8.4Hz), 2.91(1H, dd, J=17.8, 9.6Hz), 3.09(1H, dd, J=14.6, 4.2Hz), 3.13(1H, dd, J=8.4, 4.2Hz), 3.67(1H, dd, J=8.6, 3.8Hz), 4.00(1H, m), 4.20(1H, m), 6.05(2H, s), 6.84(1H, d, J=8.2Hz), 7.12(1H, d, J=1.0Hz), 7.36(2H, d, J=8.0Hz), 7.40(1H, d, J=1.6Hz), 7.53(1H, dd, J=8.2, 1.6Hz), 7.81(2H, d, J=8.2Hz), 7.92(1H, d, J=1.4Hz) |

TABLE 8-continued

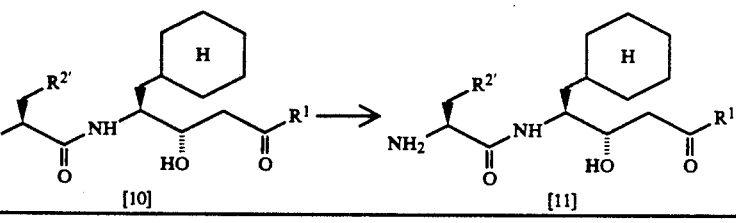

| Ex. No. | R¹ | R² | Yield % | NMR (δ) |
|---|---|---|---|---|
| 21 | cyclohexyl | Ts-N (imidazole-like) | 68 | 0.70~1.89(23H, m), 2.13(3H, bs), 2.33(1H, m), 2.45(1H, m), 2.47(1H, dd, J=17.6, 9.4Hz), 2.66(1H, dd, J=15, 2.6Hz), 2.71(1H, dd, J=14, 9.4Hz), 3.07(1H, dd, J=14.8, 3.6Hz), 7.12(1H, d, J=1.2Hz), 7.37(2H, d, J=8.4Hz), 7.48(1H, d, J=10Hz), 7.82(2H, d, J=8.4Hz), 7.94(1H, d, J=1.4Hz) |
| 22 | p-methoxyphenyl | Ts-N (imidazole-like) | 51 | 0.76~2.20(13H, m), 2.44(3H, s), 2.72(1H, dd, J=8.6, 15Hz), 2.93(1H, dd, J=9.6, 17.6Hz), 3.94(1H, dd, J=3.6, 15Hz), 3.17(1H, dd, J=2.4, 17.6Hz), 3.67(1H, dd, J=4, 8.6Hz), 3.88(3H, s), 4.02(1H, m), 4.23(1H, m), 6.93(2H, d, J=9Hz), 7.27(1H, s), 7.36(2H, d, J=8.2Hz), 7.52(1H, d, J=9.6Hz), 7.81(1H, d, J=8.4Hz), 7.91(2H, d, J=9Hz), 7.92(1H, d, J=1.8Hz) |
| 23 | phenyl | thiazolyl | 70 | 0.7~2.05(13H, m), 2.96(1H, dd, J=18, 9.4Hz), 3.15(1H, dd, J=14.2, 7.8Hz), 3.21(1H, dd, J=18, 2.6Hz), 3.36(1H, dd, J=14.2, 4.2Hz), 3.80(1H, dd, J=7.8, 4.4Hz), 4.04(1H, m), 4.24(1H, m), 7.11(1H, d, J=1.6Hz), 7.41~7.63(3H, m), 7.94(2H, m), 8.75(1H, d, J=1.8Hz) (mp. 106~107° C.) |
| 24 | 4-pyridyl | thiazolyl | 70 | 0.70~1.85(13H, m), 2.04(3H, m), 3.02(1H, dd, J=18.8, 6Hz), 3.10~3.26(2H, m), 3.36(1H, dd, J=14.4, 4.2Hz), 3.82(1H, dd, J=7.6, 4.4Hz), 4.02(1H, m), 4.26(1H, m), 7.13(1H, d, J=1.6Hz), 7.59(1H, d, J=10Hz), 7.71(2H, dd, J=4.6, 1.6Hz), 8.76(1H, d, J=2Hz), 8.82(2H, dd, J=4.6, 1.6Hz) (mp. 118~120° C.) |
| 25 | 3-thienyl | thiazolyl | 72 | 0.70~1.87(13H, m), 2.28(3H, bs), 2.89(1H, dd, J=17.6, 9.4Hz), 3.10(1H, dd, J=17.6, 2.7Hz), 3.14(1H, dd, J=14.3, 7.8Hz), 3.35(1H, dd, J=14.3, 4.1Hz), 3.78(1H, dd, J=7.8, 4.3Hz), 4.00(1H, m), 4.20(1H, m), 7.12(1H, d, J=2.0Hz), 7.31(1H, dd, J=5.1, 2.9Hz), 7.52(1H, dd, J=4.1, 1.2Hz), 7.57(1H, s), 8.08(1H, dd, J=2.9, 1.2Hz), 8.75(1H, dd, J=2Hz) |
| 26 | cyclohexyl | thiazolyl | 69 Mp. 90-93 | 0.70~1.90(24H, m), 1.98(3H, bs), 2.32(1H, m), 2.45(1H, dd, J=9.8, 1.8Hz), 2.66(1H, dd, J=18, 2.8Hz), 3.15(1H, dd, J=14, 7.4Hz), 3.35(1H, dd, J=14.4, 3.8Hz), 3.80(1H, dd, J=7.4, 4.2Hz), 3.91(1H, m), 4.02(1H, m), 7.13(1H, d, J=1.6Hz), 7.50(1H, d, J=9.8Hz), 8.78(1H, d, J=1.8Hz) |

| Compd. of Ex. No. | R¹ | R² | Yield % | [α]_D° (C = 1, CHCl₃) (Temp. °C.) | NMR (δ) |
|---|---|---|---|---|---|
| 27 | m-2-(N-morpholino)-ethoxyphenyl | thiazolyl | 76 | −46.8 (23.5) | 0.70~2.10(13H, m), 2.59(4H, 4, J=4.7Hz), 2.82(2H, t, J=5.7Hz), 2.94(1H, dd, J=9.5, 17.9Hz), 3.15(1H, dd, J=7.6, 14.6Hz), 3.18(1H, dd, J=2.5, 17.9Hz), 3.34(1H, dd, J=4.1, 14.6Hz), 3.74(4H, t, J=9.3Hz), 3.74(1H, m), 4.02(1H, m), 4.15(2H, t, J=8.7Hz), 4.22(1H, m), 7.11(1H, br, s), 7.15(1H, d, J=2.7), 7.36(1H, t, J=8.2), 7.45~7.62(2H, m), 8.75(1H, d, J=1.1Hz) |
| 28 | m-(N-formyl)-methylamino-phenyl | thiazolyl | 73 |  | 0.77~1.85(13H, m), 2.40(2H, m), 3.02(1H, dd, J=9.0, 17.9Hz), 3.17(3H, m), 3.34(3H, s), 3.35(1H, m), 3.60(1H, dd, J=4.3, 7.8Hz), 4.03(1H, m), 4.25(1H, dt, J=2.1, 8.2Hz), 7.13(1H, d, J=2.0Hz), 7.38(1H, ddofd, J=8.0, 1.2, 2.3Hz), 7.52(1H, t, J=7.52Hz), 7.59(1H, d, J=9.7Hz), 7.79(2H, m), 8.52(1H, s), 8.75(1H, d, J=2.0) |
| 29 | N-methyl-3-pyrrolyl | thiazolyl | 69 | −57.6 (24) | 0.70~2.00(13H, m), 2.65(1H, dd, J=9.8, 16.8Hz), 2.94(1H, dd, J=2.4, 17Hz), 3.13(1H, dd, J=7.6, 14.4Hz), 3.35(1H, dd, J=4.2, 14.6Hz), 3.69(3H, s), 3.77(1H, dd, J=4.2, 8Hz), 3.99(1H, m), 4.13(1H, dt, J=9.6, 2Hz), 6.56(1H, s), 6.57(1H, s), 7.11(1H, d, J=1.8Hz), 7.27(1H, s), 7.53(1H, d, J=9.6Hz), 8.76(1H, d, J=2Hz) |

TABLE 8-continued
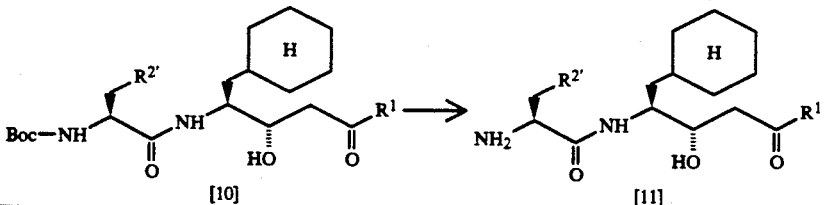
| | | | [10] | [11] |
|---|---|---|---|---|
| 30 | N-morpholino-methyl | (thiazole) | 52 | |
| 31 | N-pyperidino-methyl | (thiazole) | 36 | |
| 32 | 4-pyridyl | (2-Me-thiazole) | 76 | 0.76~1.90(13H, m), 2.35(3H, bs), 2.67(3H, s), 3.14(4H, m), 3.80(1H, dd, J=4.2, 7.8Hz), 4.03(1H, m), 4.25(1H, m), 6.88(1H, s), 7.58(1H, d, J=9.6Hz), 7.71(2H, m), 8.81(2H, m) |
| 33 | phenyl | (2-NHCHO-thiazole) | 70 | 0.78~1.75(13H, m), 3.11(4H, m), 4.07(2H, m), 4.23(1H, m), 6.70(1H, s), 7.41(2H, dd, J=7.8, 15.3Hz), 7.57(1H, t, J=7Hz), 7.88(2H, d, J=7.2Hz), 8.49(1H, s) |
| 34 | 4-pyridyl | —$CONH_2$ | 17 | |
| 35 | 4-pyridyl | —SMe | 88 | 0.70~1.80(13H, m), 2.13(3H, s), 2.73(1H, dd, J=8.2, 13.8Hz), 3.02(1H, dd, J=4, 13.6Hz), 3.09(1H, dd, J=8.6, 15.2Hz), 3.20(1H, dd, J=3.6, 18.4Hz), 3.58(1H, dd, J=4, 8.4Hz), 4.06(1H, m), 4.28(1H, m), 7.58(1H, d, J=10Hz), 7.72(2H, m), 8.81(2H, m) |

TABLE 9

Reaction scheme: [11] + R⁴'—SO₂... → [12] + [13]

| Compd. of Ex. No. | R¹ | R⁴' | R²' | Yield % | IR νmax (cm⁻¹) or NMR(δ) |
|---|---|---|---|---|---|
| 2 | phenyl | tert-butyl | (Ts-N pyrazine with methyl) | 86 | 0.70~1.82(13H, m), 1.32(9H, s), 1.93(1H, bs), 2.44(3H, s), 2.75~3.14(7H, m), 3.21(1H, m), 3.48(1H, dd, J=13.9Hz), 3.98(1H, m), 4.20(1H, m), 4.56(1H, ddd, J=6, 6, 6Hz), 6.44(1H, d, J=9.4Hz), 7.13~7.30(6H, m), 7.40~7.63(3H, m), 7.34(2H, d, J=8.4Hz), 7.80(2H, d, J=8.4Hz), 7.89(1H, d, J=1.2Hz), 7.96(2H, d, J=7.8Hz) |
| 3 | o-fluorophenyl | tert-butyl | (Ts-N pyrazine with methyl) | 73 | 0.70~1.80(13H, m), 1.34(9H, s), 2.15(2H, bs), 2.70~3.15(7H, m), 3.19(1H, m), 3.51(1H, dd, J=9.6, 13.4Hz), 3.97(1H, m), 4.15(1H, m), 4.58(1H, ddd, J=6.2, 6.2, 6.2Hz), 6.43(1H, d, J=9.0Hz), 7.18(1H, s), 7.05~7.41(7H, m), 7.34(2H, d, J=8.2Hz), 7.54(1H, m), 7.82(2H, d, J=8.6Hz), 7.87(1H, ddd, J=7.7, 1.9Hz), 7.96(1H, d, J=1.7Hz) |
| 4 | m-methoxyphenyl | tert-butyl | (Ts-N pyrazine with methyl) | 93 | 0.70~1.82(13H, m), 1.33(9H, s), 2.43(3H, s), 2.77~3.13(7H, m), 3.20(1H, m), 3.49(1H, dd, J=9, 16Hz), 3.86(3H, s), 3.48(1H, m), 4.18(1H, m), 4.56(1H, ddd, J=7, 7.7Hz), 6.40(1H, d, J=9.0Hz), 7.21(1H, s), 7.09~7.40(7H, m), 7.52(2H, m), 7.80(2H, d, J=8.4Hz), 7.87(1H, d, J=1.4Hz) |
| 5 | p-methylphenyl | tert-butyl | (Ts-N pyrazine with methyl) | 79 | 3400, 3260, 3140, 1665, 1625, 1605, 1498, 1450, 1370, 1172, 1115, 1030, 1010 |

TABLE 9-continued $R^4-SO_2CH_2$-[phenyl]-CH(NH)-C(=O)-NH-CH(CH_2-cyclohexyl)-CH(OH)-CH_2-CO-R^1 with R^2' on the CH

| Compd. of Ex. No. | R[1] | R[4'] | R[2'] | Yield % | [13] IR or NMR |
|---|---|---|---|---|---|
| 6 | tert-butyl | 2,4-difluorophenyl | Ts-N-pyrazole(methyl) | 76 | 3400(br), 1665, 1600, 1599(sh), 1500, 1475, 1175, 970, 855 |
| 7 | tert-butyl | 1-naphthyl | Ts-N-pyrazole(methyl) | 41 | 3696, 3416, 1667, 1598, 1509, 1477, 1450, 1385, 1292, 1175, 1117, 1094, 1080 |
| 8 | tert-butyl | 3-thienyl | Ts-N-pyrazole(methyl) | 74 | 3410, 3360(sh), 1665, 1598, 1510, 1385, 1173, 1116, 1093, 1078 |
| 9 | tert-butyl | 2-thiazolyl | Ts-N-pyrazole(methyl) | 81 | 0.7~1.82(13H, m), 1.35(9H, s), 2.37(1H, bs), 2.43(3H, s), 2.78~3.28(8H, m), 3.53(1H, dd, J=9.0, 13.0Hz), 3.97(1H, m), 4.18(1H, m), 4.58(1H, ddd, 6.4, 6.4, 6, 4Hz), 6.35(1H, d, J=9.0Hz), 7.05(1H, d, J=6.4Hz), 7.20(1H, s), 7.13~7.40(5H, m), 7.33(2H, d, J=8.4Hz), 7.68(1H, d, J=3.2Hz), 7.80(2H, d, J=8.4Hz), 8.00(1H, d, J=1.2Hz), 8.01(2H, d, J=3Hz) |
| 10 | tert-butyl | m-fluorophenyl | Ts-N-pyrazole(methyl) | 83 | 3460, 3360, 3280, 3160, 1665, 1625, 1590, 1500, 1450, 1115, 1032, 1010 |

TABLE 9-continued

| # | Aryl | Alkyl | Structure | Yield | IR |
|---|---|---|---|---|---|
| 11 | p-fluorophenyl | tert-butyl | Ts—N / N—CH₃ | 71 | 3410, 3280, 3160, 1665, 1625, 1600, 1509, 1450, 1155, 1115, 1030, 1010 |
| 12 | 2,6-difluorophenyl | tert-butyl | Ts—N / N—CH₃ | 97 | 3420, 1660, 1624, 1599, 1499, 1467, 1459, 1385, 1292, 1189, 1175, 1118, 1093, 1085, 1018 |
| 13 | o-methoxyphenyl | tert-butyl | Ts—N / N—CH₃ | 79 | 0.70~1.80(13H, m), 1.33(9H, s), 2.42(3H, s), 2.78~3.25(7H, m), 3.50(1H, dd, J=18, 13Hz), 3.88(3H, s), 3.95(1H, m), 4.10(1H, m), 4.48(1H, ddd, J=6.5, 6.5, 6.5Hz), 6.48(1H, d, J=9Hz), 6.97(2H, m), 7.06~7.40(9H, m), 7.49(1H, m), 7.73(1H, dd, J=9.2Hz), 7.79(2H, d, J=8Hz), 7.84(1H, s) |
| 14 | o-chlorophenyl | tert-butyl | Ts—N / N—CH₃ | 81 | 0.70~1.80(13H, m), 1.31(9H, s), 2.40(3H, s), 2.80~3.22(7H, m), 3.50(1H, dd, J=15, 7.5Hz), 3.93(1H, m), 4.09(1H, m), 4.51(1H, ddd, J=6.4, 6.4, 6.4Hz), 6.29(1H, d, J=10Hz), 7.03~7.41(8H, m), 7.53(1H, m), 7.78(2H, d, J=8.4Hz), 7.78(1H, d, J=1.4Hz) |
| 15 | m-cyanophenyl | tert-butyl | Ts—N / N—CH₃ | 84 | 3408, 2236, 1668, 1599, 1508, 1478, 1450, 1368, 1291, 1190, 1175, 1117, 1079, 908 |
| 16 | o-methylsulfonylaminophenyl | tert-butyl | Ts—N / N—CH₃ | 85 | 3420, 1666, 1607, 1578, 1499, 1452, 1387, 1340, 1290, 1174, 1155, 1117, 1079, 968, 909 |
| 17 | p-trifluoromethylphenyl | tert-butyl | Ts—N / N—CH₃ | 85 | 3400~3200, 3140, 1665, 1625, 1600, 1510, 1450, 1410, 1325, 1175, 1135, 1115, 1065 |

TABLE 9-continued

[Structure: R4'-SO2CH2 - phenyl with R2' substituent - CH - NH - C(=O) - CH(NH-) - CH(OH) - CH2 - CO - R1, with cyclohexyl-H group]

| Compd. of Ex. No. | R[1] | R[4'] | R[2'] | Yield % | [13] NMR(δ) |
|---|---|---|---|---|---|
| 18 | m-morpholino-carbonyloxy-phenyl | tert-butyl | Ts-N⟨⟩N (methyl-imidazole) | 79 | 0.70~1.82(13H, m), 1.90(1H, bs), 1.32(9H, s), 2.43(3H, s), 2.74~3.30(7H, m), 3.49(1H, dd, J=14, 10Hz), 3.52~3.82(8H, m), 3.96(1H, m), 4.16(1H, m), 4.54(1H, ddd, J=6.2, 6.2, 6.2Hz), 6.40(1H, d, J=9.4Hz), 7.10~7.40(7H, m), 7.33(2H, d, J=8.2Hz), 7.48(1H, t, J=7.5Hz), 7.70(1H, m), 7.80(2H, d, J=8.4Hz), 7.80(1H, m), 7.89(1H, d, J=1.2Hz) |
| 19 | m-morpholino-carbonylphenyl | tert-butyl | Ts-N⟨⟩N | 85 | 0.7~1.82(13H, m), 1.32(9H, s), 2.43(3H, s), 2.70~3.30(8H, m), 3.48(1H, dd, J=9.4, 12.8Hz), 3.30~3.90(8H, m), 3.99(1H, m), 4.20(1H, m), 4.53(1H, ddd, J=6.2, 6.2, 6.2Hz), 6.42(1H, d, J=9.4Hz), 7.08~7.31(6H, m), 7.34(2H, d, J=8.2Hz), 7.45~7.68(2H, m), 7.81(2H, d, J=8.4Hz), 7.91(1H, d, J=1.4Hz), 8.05(2H, m) |
| 20 | 3',4'-methylene-dioxyphenyl | tert-butyl | Ts-N⟨⟩N | 89 | 0.7~1.8(13H, m), 1.9(1H, bs), 1.33(9H, s), 2.44(3H, s), 2.74~3.30(7H, m), 3.50(1H, dd, J=9.2, 13Hz), 3.96(1H, m), 4.16(1H, m), 4.56(1H, ddd, J=6.4, 6.4, 6.4Hz), 6.06(2H, s), 6.40(1H, d, J=9.2Hz), 6.85(1H, d, J=8.2Hz), 7.25(6H, m), 7.34(1H, d, J=8.2Hz), 7.45(1H, d, J=1.6Hz), 7.56(1H, dd, J=8.2, 1.6Hz), 7.80(2H, d, J=8.4Hz), 7.85(1H, d, J=1.4Hz) |

| Compd. of Ex. No. | R[1] | R[4'] | R[2'] | Yield % | [13] NMR(δ) |
|---|---|---|---|---|---|
| 21 | cyclohexyl | tert-butyl | Ts-N⟨⟩N | 86 | 0.70~1.90(23H, m), 1.34(9H, s), 2.33(1H, m), 2.44(3H, s), 2.78~3.27(8H, m), 3.50(1H, dd, J=12.0, 8.4Hz), 3.86(1H, m), 3.96(1H, m), 4.54(1H, ddd, J=6.2, 6.2, 6.2Hz), 6.35(1H, d, J=10Hz), 7.13~7.34(6H, m), 7.37(2H, d, J=8.4Hz), 7.82(2H, d, J=8.4Hz), 7.90(1H, d, J=1.4Hz), |

TABLE 9-continued

| 22 | p-methoxy-phenyl | tert-butyl | Ts-N⟨N⟩ (methyl) | 87 | 0.72~1.80(13H, m), 0.90(1H, m), 1.33(9H, bs), 1.33(9H, m), 2.43(3H, s), 2.78~3.12(7H, m), 3.20(1H, m), 3.49(1H, dd, J=9.4, 13.2Hz), 3.88(3H, s), 3.97(1H, dd, J=9.4, 13.2Hz), 3.88(3H, s), 3.97(1H, s), 4.17(1H, ddd, J=7.4, 7.4, 7.4Hz), 4.57(1H, ddd, J=6, 6, 6Hz), 6.42(1H, d, J=9.4Hz), 6.94(2H, d, J=9Hz), 7.16~7.26(6H, m), 7.22(1H, s), 7.34(2H, d, J=8Hz), 7.79(2H, d, J=8.4Hz), 7.84(1H, d, J=1.2Hz), 7.94(2H, d, J=9Hz) |

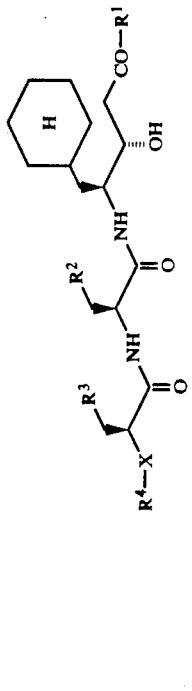

[13] (IIA)

| Compd. of Ex. No. | R¹ | R² | R³ | X | R⁴ | Yield % | NMR(δ) |
|---|---|---|---|---|---|---|---|
| 23 | phenyl | (thiazolyl) | phenyl | CH₂ | ⟨tolyl⟩-SO₂ | 86 | 0.7~1.88(13H, m), 1.32(9H, s), 2.83~3.55(9H, m), 3.96(1H, m), 4.15(1H, m), 4.74(1H, ddd, J=5.6Hz×3), 6.32(1H, d, J=9.8Hz), 7.13(1H, d, J=2Hz), 7.25(5H, m), 7.47(2H, t, J=7.8Hz), 7.57(1H, d, J=7.8Hz), 7.96(2H, d, J=7.2Hz), 8.65(1H, d, J=2Hz) |
| 24 | 4-pyridyl | (thiazolyl) | phenyl | CH₂ | ⟨tolyl⟩-SO₂ | 86 | 0.60~1.80(13H, m), 1.33(9H, s), 1.88(2H, bs), 2.86~3.50(9H, m), 3.99(1H, m), 4.15(1H, m), 4.66(1H, ddd, J=6Hz×3), 6.33(1H, d, J=9.2Hz), 7.16(1H, d, J=0.6Hz), 7.28(5H, m), 7.65(1H, d, J=6Hz), 7.82(2H, bs), 8.69(1H, d, J=0.6Hz), 8.82(2H, bs) |
| 25 | 3-thienyl | (thiazolyl) | phenyl | CH₂ | ⟨tolyl⟩-SO₂ | 79 | 0.65~1.82(13H, m), 1.33(9H, s), 2.82~3.55(9H, m), 3.95(1H, m), 4.15(1H, m), 4.72(1H, ddd, J=6Hz×3), 6.33(1H, d, J=9.4Hz), 7.14(1H, d, J=2Hz), 7.17~7.38(6H, m), 7.55(1H, dd, J=5.2, 1.4Hz), 7.55(1H, s), 8.20(1H, dd, J=1.2, 2.8Hz), 8.67(1H, d, J=2Hz) |
| 26 | cyclohexyl | (thiazolyl) | phenyl | CH₂ | ⟨tolyl⟩-SO₂ | 87 | 0.7~2.00(24H, m), 1.35(9H, s), 2.32(1H, m), 2.88~3.58(9H, m), 3.83(1H, m), 3.92(1H, m), 4.70(1H, ddd, J=5.2Hz×3), 6.30(1H, d, J=9.8Hz), 7.16(1H, d, J=2Hz), 7.27(5H, m), 7.50(1H, d, J=5.8Hz), 8.71(1H, d, J=2.2Hz) |

TABLE 9-continued

| # | (Ar) | (Het) | X | (R) | Yield | NMR |
|---|---|---|---|---|---|---|
| 27 | m-2-(N-morpholino)ethoxyphenyl | thiazolyl-Me | CH₂ | -SO₂-C(CH₃)₃ | — | 0.6~1.8(13H, m), 2.60(4H, m), 2.84(2H, t, J=11.2Hz), 2.89~3.62(9H, m), 3.75(4H, m), 3.95(1H, ddd, J=7.8Hz×3), 4.18(2H, t, J=5.4Hz), 4.18(1H, m), 4.73(1H, ddd, J=5.2Hz×3), 6.32(1H, d, J=9.4Hz), 7.14(1H, d, J=2Hz), 7.14(1H, m), 7.22~7.56(3H, m), 8.67(1H, d, J=2Hz) |
| 28 | m-(N-formyl)methylaminophenyl | thiazolyl-Me | NH | morpholino-NSO₂ | 91 | 0.60~1.78(13H, m), 2.51(2H, m), 2.84(4H, m), 3.17(2H, m), 3.37(3H, s), 3.40(5H, m), 3.54(1H, dd, J=4.1, 10Hz), 3.96(2H, m), 4.14(1H, m), 4.74(1H, m), 5.20(1H, d, J=5.7Hz), 6.60(1H, d, J=6.6Hz), 7.15(1H, d, J=1.9Hz), 7.34(5H, m), 7.53(1H, t, J=8.9Hz), 7.89(2H, m), 8.61(1H, s), 8.84(1H, d, J=2.1Hz), 9.26(1H, d, J=7.2Hz) |
| 29 | N-methylpyrrolyl | thiazolyl-Me | CH₂ | -SO₂-C(CH₃)₃ | 91 | 0.70~1.80(13H, m), 2.63(1H, dd, J=9.6, 16.8Hz), 2.80(1H, dd, J=2.5, 16.8Hz), 2.95(2H, m), 3.07~3.33(3H, m), 3.48(2H, m), 3.69(3H, s), 3.90(1H, ddd, J=7.4Hz×3), 4.06(1H, m), 4.75(1H, ddd, J=5.6Hz), 6.36(1H, d, J=9.6Hz), 6.57(1H, s), 6.58(1H, m), 7.11(1H, d, J=1.8Hz), 7.28(6H, m), 7.49(1H, d, J=6.8Hz), 8.69(1H, d, J=2Hz) |
| 30 | (N-morpholino)methyl | thiazolyl-Me | NH | morpholino-NSO₂ | 85 | 0.58~2.00(13H, m), 2.58(8H, m), 2.98(3H, m), 3.27(4H, m), 3.60(1H, dd, J=4.8, 14.8Hz), 3.80(6H, m), 4.15(2H, m), 4.78(1H, m), 5.03(1H, d, J=4.5Hz), 6.60(1H, d, J=9.4Hz), 7.18(1H, d, J=1.8Hz), 7.44(1H, s), 7.45(1H, ddd, J=7Hz×3), 7.61(1H, t, J=7.2Hz), 7.72(1H, t, J=7.0Hz), 7.86(1H, d, J=8.2Hz), 7.94(1H, d, J=7.0Hz), 8.42(1H, d, J=8.2Hz), 8.86(1H, d, J=1.8Hz), 9.45(1H, d, J=7.8Hz) |
| 31 | (N-pyperidino)methyl | thiazolyl-Me | NH | morpholino-NSO₂ | 48 | 0.60~2.08(19H, m), 2.54(7H, m), 2.71(2H, m), 2.99(3H, m), 3.22(1H, m), 3.28(2H, s), 3.60(1H, dd, J=5, 15Hz), 3.80(2H, m), 4.14(2H, m), 4.80(1H, m), 5.07(1H, bs), 6.64(1H, d, J=8.6Hz), 7.18(1H, d, J=1.8Hz), 7.45(2H, ddd, J=7.0Hz×3), 7.60(1H, t, J=6.6Hz), 7.70(1H, t, J=6.6Hz), 7.86(1H, d, J=8.6Hz), 7.94(1H, d, J=7.8Hz), 8.24(1H, d, J=8.6Hz), 8.84(1H, d, J=1.8Hz), 9.34(1H, d, J=7.4Hz) |
| 32 | 4-pyridyl | thiazolyl-Me (with Me) | NH | morpholino-NSO₂ | 58 | 0.78~1.68(13H, m), 2.45(2H, m), 2.75(3H, s), 2.83(3H, m), 3.10(3H, m), 3.43(4H, m), 3.45(2H, m), 3.97(2H, m), 4.12(1H, m), 4.75(1H, m), 5.16(1H, d, J=5Hz), 6.70(1H, d, J=9.4Hz), 6.92(1H, s), 7.33(5H, m), 7.82(2H, bs), 8.85(2H, bs), 9.22(1H, d, J=7.6Hz) |
| 33 | phenyl | thiazolyl-Me (with NH-CHO) | CH₂ | -SO₂-C(CH₃)₃ | 95 | 0.70~1.85(13H, m), 1.30(9H, s), 2.84(1H, m), 3.14(7H, m), 3.46(1H, m), 4.06(1H, m), 4.13(1H, ddd, J=7Hz), 4.63(1H, m), 6.40(1H, d, J=10Hz), 6.79(1H, s), 7.25(5H, m), 7.48(2H, t, J=7.5Hz), 7.57(1H, m), 7.97(2H, m), 8.51(1H, m) |
| | | | | | 71 | |

TABLE 9-continued

| # | Ar | X | R | Yield (%) | NMR |
|---|----|---|---|---|-----|
| 34 | 4-pyridyl | —CONH₂ | NH | naphthyl | 70 | 0.79~1.78(13H, m), 2.10(2H, m), 2.50(2H, m), 2.68(3H, m), 2.96(4H, m), 3.13(2H, m), 3.93(1H, dd, J=3.6, 14.2Hz), 4.05(1H, m), 4.21(2H, m), 4.78(1H, m), 7.28(1H, d, J=9.0Hz), 7.44(2H, d, J=4.4Hz), 7.58(2H, m), 7.88(4H, m), 8.20(1H, d, J=7.8Hz), 8.50(1H, d, J=8.0Hz), 8.80(2H, bs) |
| 35 | 4-pyridyl | —SMe | NH | naphthyl(NSO₂-morpholine) | 84 | 0.80~1.80(13H, m), 2.14(3H, s), 2.63(2H, m), 2.96(1H, m), 3.26(3H, m), 3.49(4H, m), 3.98(1H, dddd, J=5.0Hz×4), 4.12(1H, m), 4.25(1H, m), 4.65(1H, ddd, J=5.8Hz), 4.99(1H, d, J=5.4Hz), 6.90(1H, d, J=10Hz), 7.30(5H, m), 7.78(2H, bs), 8.83(2H, bs) |
| 36 | 4-pyridyl | thiazolyl | CH₂ | naphthyl(SO₂-tBu) | 89 | 0.78~1.80(13H, m), 2.95~3.55(10H, m), 3.99(1H, ddd, J=7.8Hz), 4.18(1H, m), 4.63(1H, ddd, J=5.6Hz), 6.39(1H, d, J=9.4Hz), 7.11(1H, d, J=1.8Hz), 7.38(2H, d, J=5.2Hz), 7.58(3H, m), 7.76(3H, m), 7.89(1H, m), 8.03(1H, d, J=7.8Hz), 8.54(1H, d, J=1.8Hz), 8.80(2H, bs) |
| 37 | phenyl | N-Ts imidazolyl | CH₂ | naphthyl(SO₂-iPr) | 89 | 0.70~1.82(13H, m), 1.22(3H, d, J=7Hz), 1.30(3H, d, J=7Hz), 1.90(1H, bs), 2.43(3H, s), 2.72~3.23(8H, m), 3.49(1H, dd, J=13.2, 9.6Hz), 3.99(1H, m), 4.19(1H, m), 4.57(1H, ddd, J=6Hz×3), 6.40(1H, d, J=9.4Hz), 7.96(2H, d, J=6.8Hz), 7.15~7.32(6H, m), 7.34(2H, d, J=8.4Hz), 7.42~7.63(3H, m), 7.85(2H, d, J=8.4Hz), 7.85(1H, d, J=8.4Hz) |
| 38 | phenyl | N-Ts imidazolyl | CH₂ | naphthyl(SO₂Et) | 98 | 0.70~1.83(13H, m), 1.23(3H, t, J=7.4Hz), 2.43(3H, s), 2.20(2H, bs), 2.65~3.24(8H, m), 3.50(1H, dd, J=9.6, 14.2Hz), 4.00(1H, m), 4.19(1H, m), 4.57(1H, ddd, J=6.2Hz×3), 6.43(1H, d, J=8.4Hz), 7.06~7.40(8H, m), 7.40~7.63(3H, m), 7.80(2H, d, J=8.4Hz), 7.88(1H, s), 7.97(2H, d, J=1.8Hz) |
| 39 | phenyl | thiazolyl | CH₂ | naphthyl(N-acetyl morpholine) | 76 | 0.70~1.80(13H, m), 2.28(1H, dd, J=6.2, 16.4Hz), 2.66(1H, dd, J=4, 16.8Hz), 2.92(3H, m), 3.05~3.75(12H, m), 4.06(1H, m), 4.19(1H, m), 4.79(1H, ddd, J=6.2Hz), 6.78(1H, d, J=10Hz), 7.18(1H, d, J=1.8Hz), 7.30~7.57(7H, m), 7.77(1H, d, J=7.8Hz), 7.88(1H, m), 8.04(3H, m), 8.29(1H, d, J=6.4Hz), 8.69(1H, d, J=1.8Hz) |
| 40 | phenyl | N-Ts imidazolyl | CH₂ | naphthyl(N-acetyl morpholine) | 81 | 0.80~1.80(13H, m), 2.40(3H, s), 2.90~3.75(17H, m), 4.06(1H, m), 4.22(1H, d, J=9.2Hz), 4.63(1H, ddd, J=5Hz), 6.87(1H, d, J=9.6Hz), 7.18~7.59(9H, m), 7.74~8.14(10H, m) |

TABLE 9-continued

| | | | | | |
|---|---|---|---|---|---|
| 41 | 4-pyridyl | thiazole | CH₂ | naphthyl | N-acetyl morpholine | 0.70~1.79(13H, m), 2.25(1H, m), 2.74(1H, dd, J=3.8, 16.8Hz), 2.88(1H, dd, J=6.6, 17Hz), 2.96(3H, m), 3.08–3.64(10H, m)3.75(1H, dd, J=4.8, 13Hz), 4.12(2H, m), 4.75(1H, ddd, J=5.8Hz×3), 6.82(1H, d, J=9.4Hz), 7.19(1H, d, J=2Hz), 8.77(2H, bs), 7.28(1H, d, J=7.6Hz), 7.41(1H, t, J=7Hz), 7.54(2H, m), 7.78(1H, d, J=8Hz), 7.87(3H, m), 8.03(1H, m), 8.46(1H, d, J=6.2Hz), 8.71(1H, d, J=2Hz) |
| 42 | 4-pyridyl | TS-thiazole | CH₂ | naphthyl | N-acetyl morpholine | |
| 43 | 4-pyridyl | thiazole | NH | phenyl | NSO₂ morpholine | 0.70~1.90(13H, m), 2.49(2H, m), 2.87(3H, m), 3.15(3H, m), 3.41(4H, m), 3.57(2H, m), 3.97(2H, m), 4.11(1H, m), 4.74(1H, m), 5.11(1H, d, J=5Hz), 6.59(1H, d, J=9.2Hz), 7.15(1H, d, J=2Hz), 7.32(5H, m), 7.85(2H, m), 8.85(1H, d, J=2Hz), 8.85(2H, m), 9.34(1H, d, J=7Hz) |
| 44 | 4-pyridyl | thiazole | NH | naphthyl | NSO₂ morpholine | 0.76~1.86(13H, m), 1.95(2H, m), 2.50(2H, m), 2.66(2H, m), 2.88~3.29(6H, m), 3.58(1H, dd, J=5, 15Hz), 3.98(1H, m), 4.13(3H, m), 4.79(1H, m), 5.05(1H, d, J=4.5Hz), 6.63(1H, d, J=10Hz), 7.17(1H, d, J=1.7Hz), 7.43(2H, m), 7.59(2H, m), 7.88(4H, m), 8.69(1H, m), 8.85(1H, d, J=2Hz), 8.55(2H, bs), 9.51(1H, d, J=7Hz) |
| 45 | cyclohexyl | thiazole | NH | phenyl | NSO₂ morpholine | 0.77~1.85(23H, m), 2.36(1H, m), 2.56(4H, m), 2.85(3H, m), 3.18(1H, dd, J=5.2, 14.4Hz), 3.49(6H, m), 3.90(3H, m), 4.75(1H, m), 5.01(1H, d, J=5.8Hz), 6.55(1H, d, J=9.2Hz), 7.16(1H, d, J=1.8Hz), 7.32(5H, m), 8.84(1H, d, J=1.8Hz), 9.10(1H, d, J=7.2Hz) |
| 46 | 4-pyridyl | thiazole | NH | phenyl | Me₂CHNSO₂ | 0.77~1.80(13H, m), 2.35(6H, s), 2.75(1H, dd, J=10.6, 13.8Hz), 3.15(3H, m), 3.43(1H, dd, J=3.8, 13.8Hz), 3.55(1H, dd, J=4.2, 15Hz), 3.75(1H, m), 3.95(2H, m), 4.12(1H, m), 4.73(1H, m), 4.98(1H, d, J=5Hz), 6.63(1H, d, J=9.4Hz), 7.13(1H, d, J=2Hz), 7.31(5H, m), 7.85(2H, m), 8.84(1H, d, J=2), 8.84(2H, bs), 9.39(1H, d, J=7.2Hz) |
| 47 | 4-pyridyl | thiazole | NH | phenyl | CH₂C(O)-morpholine | 0.79~1.80(13H, m), 2.30(4H, m), 2.42(2H, m), 2.85~3.62(11H, m), 3.94(1H, m), 4.00(1H, m), 4.20(1H, m), 4.42(1H, m), 4.75(1H, m), 6.63(1H, d, J=9.4Hz), 7.16(1H, d, J=2Hz), 7.29(5H, m), 7.71(1H, d, J=4.4Hz), 7.85(2H, m), 8.33(1H, d, J=7Hz), 8.62(1H, d, J=2Hz), 8.83(2H, bs) |

TABLE 9-continued

| | | | | | |
|---|---|---|---|---|---|
| 48 | 4-pyridyl | NH | [naphthyl] | 94 | 0.79~1.76(13H, m), 2.20(2H, m), 2.49(2H, m), 2.80~3.08(4H, m), 3.19~3.56(7H, m), 3.92(1H, dd, J=4.4, 14.2Hz), 4.00(1H, m), 4.20(1H, m), 4.55(1H, m), 4.74(1H, m), 6.65(1H, d, J=9.6Hz), 7.15(1H, d, J=1.6Hz), 7.45(2H, d, J=5.4Hz), 7.57(2H, m), 7.85(4H, m), 8.19(1H, m), 8.33(1H, d, J=7), 8.52(1H, d, J=2Hz), 8.83(2H, bs) |
| 49 | m-2-(N-morpholino ethoxy-phenyl) | NH | [naphthyl] | 77 | 0.82~1.80(13H, m), 2.19(2H, m), 2.33(2H, m), 2.60(4H, m), 2.77~3.25(6H, m), 3.43(7H, m), 3.74(4H, m)3.83(1H, dd, J=5, 15Hz), 3.98(1H, m), 4.21(3H, m), 4.63(1H, m), 4.76(1H, dddd, J=5.2Hz×4), 4.76(1H, m), 6.64(1H, d, J=9.8Hz), 7.12(1H, d, J=1.4Hz), 7.15(1H, m), 7.41(3H, m), 7.55(3H, m), 7.67(2H, m), 7.84(2H, m), 8.17(1H, m), 8.54(1H, d, J=2Hz) |
| 50 | 4-pyridyl | NH | [phenyl] | 86 | 0.60~1.80(13H, m), 3.08(5H, m), 3.33(4H, m), 3.57(2H, m), 3.64(4H, m), 4.05(1H, m), 4.18(1H, m), 4.65(1H, m), 4.95(1H, bs), 6.87(1H, d, J=9.8Hz), 7.17(1H, J=1.2Hz), 7.30(5H, m), 8.17(2H, m), 8.58(1H, d, J=9.Hz), 8.70(1H, d, J=1.2Hz), 8.84(2H, m) |
| 51 | m-2-(N-morpholino ethoxy-phenyl) | CH$_2$ | [phenyl] | 70 | 0.70~1.80(13H, m), 2.28(1H, dd, J=6.6, 17.5Hz), 2.56(4H, m),2.68(1H, dd, J=4, 16.6Hz), 2.80(3H, m), 2.95(1H, m), 3.18(2H, m), 3.35(4H, m), 3.50(2H, m), 3.63(1H, dd, J=5.4, 12Hz), 3.71(4H, t, J=4.4Hz), 3.87(1H, d, J=7.4Hz), 4.05(1H, m), 4.16(3H, t, J=5.6Hz), 4.77(1H, ddd, J=6.4Hz×3), 6.79(1H, d, J=9.6Hz), 7.09(1H, dd, J=2.4, 8Hz), 7.18(1H, d, J=7.8Hz), 7.35(3H, m), 7.54(3H, m), 7.63(1H, d, J=7.8Hz), 7.77(1H, d, J=7.6Hz), 7.88(1H, m), 8.02(1H, m), 8.28(1H, d, J=6.4Hz), 8.70(1H, d, J=1.8Hz) |
| 52 | cyclohexyl | NH | [naphthyl] | 94 | 0.78(23H, m), 2.22(2H, m), 2.38(2H, m), 2.58(2H, m), 3.00(3H, m), 3.48(6H, m), 3.82(1H, dd, J=5, 14.6Hz), 3.82(1H, m), 3.98(1H, m), 4.63(1H, m), 4.74(1H, ddd, J=8.8Hz), 6.56(1H, d, J=8.8Hz), 7.12(1H, d, J=1.8Hz), 7.44(2H, m), 7.58(2H, dt, J=1.8, 6.4Hz), 7.80(1H, m), 7.89(1H, m), 8.11(1H, d, J=7.8Hz), 8.22(1H, d, J=7.2Hz), 8.54(1H, d, J=1.8Hz) |

| Compd. of Ex. No. | [α]$_D$° C = 1.0, CHCl$_3$ (Temp. °C.) | Molecular formula (Molecular weight) | Calcd. | Found | IR ν$_{max}$$^{CHCl_3}$ cm$^{-1}$ |
|---|---|---|---|---|---|
| 23 | −20.1 (24) | C$_{37}$H$_{49}$N$_3$O$_6$S$_2$·½H$_2$O (704.94) | C: 63.04 H: 7.15 N: 5.96 S: 9.10 | C: 63.28 H: 7.21 N: 5.91 S: 8.97 | 3520, 3420, 3360(br) 1670, 1600, 1580, 1450, 1118 |
| 24 | −22.6 (24) | C$_{36}$H$_{48}$N$_4$O$_6$S$_2$·¼H$_2$O (708.93) | C: 61.65 H: 6.77 N: 7.99 S: 9.14 | C: 61.47 H: 7.02 N: 8.01 S: 8.91 | 3410, 3360, 1665, 1605, 1595, 1505, 1450, 1410, 1115 |
| 25 | −23.1 (25) | C$_{35}$H$_{47}$N$_3$O$_6$S$_3$ (701.948) | C: 59.89 H: 6.75 N: 5.99 S: 13.70 | C: 59.68 H: 6.71 N: 5.89 s: 13.41 | 3315, 1665, 1510, 1412, 1290, 1115 |
| 26 | −19.6 (24) | C$_{37}$H$_{55}$N$_3$O$_6$S$_2$·¼H$_2$O (710.99) | C: 62.51 H: 7.94 N: 5.91 S: 9.02 | C: 62.60 H: 8.05 N:5.76 S: 8.87 | 3520, 3420, 3360, (br-sh), 1665, 1605, 1510, 1450, 1118 |
| 27 | −14.4 (23.5) | C$_{43}$H$_{60}$N$_4$O$_8$S$_2$·¼H$_2$O (834.101) | C: 61.92 H: 7.37 N: 6.72 S: 7.69 | C: 61.77 H: 7.51 N: 6.52 S: 7.41 | 3500, 3420, 3360, 1665, 1596, 1581, 1505, 1460, 1448 |
| 28 | (24.0) −23.2 (MeOH) | C$_{38}$H$_{50}$N$_6$O$_8$S$_2$·½H$_2$O·¼CH$_2$Cl$_2$ (836.462) | C: 55.23 H: 6.30 N: 10.04 S: 7.66 | C: 55.02 H: 6.07 N: 10.01 S: 7.44 | 3370, 1672, 1603, 1586, 1511, 1450, 1406, 1341, 1262, 1158, 1116 |
| 29 | −24.1 (24.0) | C$_{36}$H$_{50}$N$_4$O$_6$S$_2$·½H$_2$O·¼iPr$_2$O (733.490) | C: 61.41 H: 7.49 N: 7.64 S: 8.74 | C: 61.28 H: 7.43 N: 7.50 S: 8.50 | 3500, 3420, 3360, 1660, 1605, 1530, 1508, 1462, 1450 |
| 30 | | C$_{39}$H$_{54}$N$_6$O$_8$S$_2$·3/2H$_2$O·¼iPr$_2$O | C: 57.88 H: 7.54 | C: 57.65 H: 7.31 | 3380(3300), 1712, 1665, 1600(1535), 1510, 1455, 1430 |

TABLE 9-continued

| # | mp | Formula (MW) | Analysis | | | | IR |
|---|---|---|---|---|---|---|---|
| 31 | | (902.655) | N: 9.31 | S: 7.10 | N: 9.59 | S: 6.88 | 3380(3280), 1705, 1662, 1600, 1535, 1510, 1450, 1400 |
| | | C₄₀H₅₆N₆O₇S₂.H₂O.½iPr₂O | C: 59.30 | H: 7.37 | C: 59.44 | H: 7.45 | |
| 32 | −37.0 (24) 162-64 | (840.587) | N: 10.00 | S: 7.63 | N: 9.88 | S: 7.55 | 3560, 3380(3300), 1675, 1602, 1595, 1510(1535), 1455 |
| | | C₃₆H₄₈N₆O₇S₂.¼H₂O | C: 58.01 | H: 6.56 | C: 57.94 | H: 6.53 | |
| | | (745.044) | N: 11.27 | S: 8.60 | N: 11.36 | S: 8.36 | |
| 34 | | C₃₇H₄₈N₆O₈S.½H₂O | C: 59.58 | H: 6.62 | C: 59.37 | H: 6.66 | 3600, 3360, 1732, 1685, 1664, 1640, 1600, 1545 |
| | | (745.876) | N: 11.27 | S: 4.30 | N: 11.39 | S: 4.25 | |
| 35 | −62.6 (24) 175-8 | C₂₃H₄₇N₅O₇S₂.½H₂O | C: 56.71 | H: 6.92 | C: 56.60 | H: 6.77 | 3600, 3380, 1670(1690), 1600, (1515, 1525) 1500 |
| | | (698.886) | N: 10.02 | S: 9.17 | N: 9.87 | S: 9.01 | |
| 36 | −14.5 (24) | C₄₃H₆₀N₄O₈S₂.3/2H₂O.½iPr₂O | C: 62.60 | H: 7.33 | C: 62.65 | H: 7.13 | 3500, 3400, 3370, 1665, 1598, 1510, (sh, 1550, 1525) |
| | | (825.074) | N: 6.79 | S: 7.77 | N: 6.79 | S: 7.59 | |
| 39 | 98-100 | C₄₂H₅₀N₄O₆S.½H₂O | C: 67.45 | H: 6.87 | C: 67.47 | H: 6.93 | |
| | | (749.952) | N: 7.49 | S: 4.29 | N: 7.54 | S: 4.23 | |
| 41 | −19.7 (25.5) | C₄₁H₄₉N₅O₆S.H₂O | C: 64.97 | H: 6.78 | C: 65.08 | H: 6.82 | 3400, 3340, 1665, (sh, 1695), 1625, 1530, 1510, 1450, 1410 |
| | | (757.947) | N: 9.24 | S: 4.23 | N: 9.21 | S: 3.95 | |
| 43 | −33.2 (25.5) | C₃₅H₄₆N₆O₆S₂ | C: 57.83 | H: 6.38 | C: 57.89 | H: 6.36 | 3560, 3540, 3380, (sh, 3300), 1665, 1500, 1530, 1510 |
| | | (726.921) | N: 11.56 | S: 8.82 | N: 11.47 | S: 8.72 | |
| 44 | −40.7 (24) 108-110 | C₄₁H₅₃N₂O₈S₂ | C: 59.33 | H: 6.44 | C: 59.40 | H: 6.50 | 3560, 3520, 3390, (sh 3300), 1670, 1600, 1535, 1510 |
| | | (830.014) | N: 10.13 | S: 7.73 | N: 10.04 | S: 7.50 | |
| 45 | −34.6 (24) | C₃₆H₅₃N₅O₇S.½iPr₂O | C: 58.80 | H: 7.78 | C: 58.55 | H: 7.55 | 3540, 3380, 3300, 1670, 1605, 1530, 1510, 1450, 1408 |
| | | (796.554) | N: 8.79 | S: 8.05 | N: 9.05 | S: 7.77 | |
| 46 | −32.0 (25) | C₃₃H₄₄N₆O₆S₃.½H₂O.½iPr₂O.½CHCl₂ | C: 56.83 | H: 6.91 | C: 66.85 | H: 6.82 | 3550, 3380(3300), 1665, 1605, 1596, 1530, 1510, 1455, 1450 |
| | | (766.200) | N: 10.97 | S: 8.37 | N: 11.14 | S: 8.01 | |
| 47 | | C₃₇H₄₈N₆O₆S.3/2H₂O.1/10iPr₂O | C: 60.71 | H: 7.03 | C: 60.79 | H: 7.05 | |
| | | (733.120) | N: 11.46 | S: 4.37 | N: 11.56 | S: 4.31 | |
| 48 | −23.0 (25) | C₄₁H₅₀N₆O₆S.5/4H₂O | C: 68.34 | H: 6.81 | C: 63.34 | H: 6.92 | 3520, 3340, 1670, 1600, 1510(1530) |
| | | (777.444) | N: 10.81 | S: 4.12 | N: 10.64 | S: 3.81 | |
| 49 | −19.3 (25) | C₄₈H₆₂N₆O₈S.3/2H₂O | C: 63.34 | H: 7.20 | C: 63.49 | H: 7.27 | 3520, 3340, 1670, 1598, 1580, 1510, (sh 1530) |
| | | (910.114) | N: 9.23 | S: 3.52 | N: 9.35 | S: 3.36 | |
| 50 | −24.8 (24) | C₃₆H₄₆N₆O₆S₂.H₂O.1/5.D₂O | C: 61.35 | H: 7.03 | 3430(3480)3320, 1670, 1640, 1603, 1510 |
| | | (729.31) | N: 11.36 | S: 4.16 | |
| 51 | −15.6 (25) | C₄₈H₆₁N₅O₈S.½H₂O | C: 65.39 | H: 7.15 | C: 65.63 | H: 7.44 | 3400, 3340, 1668, (1635), 1600, 1585, 1511, 1460, 1440 |
| | | (881.586) | N: 7.94 | S: 3.64 | N: 7.85 | S: 3.39 | |
| 52 | −26.0 (24) | C₄₂H₅₇N₅O₆S.½H₂O | C: 65.66 | H: 7.60 | C: 65.66 | H: 7.68 | 3480, 3340, 1670, 1598, 1508, (1525), 1448, 1425, 1410 |
| | | (768.990) | N: 9.11 | S: 4.17 | N: 9.08 | S: 3.89 | |

TABLE 10

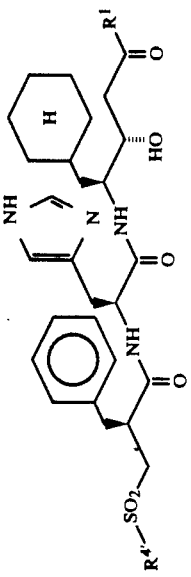

(IA)

| Compd. of Ex. No. | $R^1$ | $R^4$ | Yield % | $[\alpha]_D$ (C = 1.0, MeOH) (°C.) | Molecular formula | Elemental analysis Calcd. | Elemental analysis Found | IR $\nu$max cm$^{-1}$ | NMR ($\delta$): |
|---|---|---|---|---|---|---|---|---|---|
| 2 | phenyl | tert-butyl | 75 | −22.2° (24° C.) | $C_{37}H_{50}N_4O_6S\cdot\frac{1}{4}H_2O\cdot\frac{1}{2}iPr_2O$ | C: 64.82 H: 7.70 N: 7.85 S: 4.49 | C: 64.87 H: 7.65 N: 7.99 S: 4.33 | 3460, 3360(br), 1663, 1600, 1580, 1498, 1450, 1116 | 0.70~1.83(13H, m), 1.33(9H, s), 2.68~3.18(7H, m), 3.27(1H, m), 3.60(1H, dd, J=9.8, 13.2Hz), 3.80(1H, br), 3.99(1H, m), 4.21(1H, m), 4.60(1H, m), 6.48(1H, d, J=9.4Hz), 6.89(1H, s), 7.08~7.63(8H, m), 7.50(1H, d, J=1.8Hz), 7.93(2H, d, J=8.4Hz) |
| 3 | o-fluorophenyl | tert-butyl | 90 | −20.9 (24.0) | $C_{37}H_{49}FN_4O_6S\cdot\frac{1}{2}H_2O$ | C: 62.56 F: 2.67 H: 7.17 N: 7.89 S: 4.51 | C: 62.65 F: 2.71 H: 7.12 N: 8.05 S: 4.56 | 3460, 3360(br), 1666, 1611, 1575, 1480, 1453, 1116 | 0.68~1.83(13H, m), 1.33(9H, s), 2.70~3.17(7H, m), 3.60(1H, dd, J=13.1, 9.9Hz), 3.59(2H, brs), 3.25(1H, m), 3.98(1H, m), 4.18(1H, m), 4.59(1H, ddd, J=6.8, 6.8, 6.8Hz), 6.51(1H, d, J=9.0Hz), 6.90(1H, s), 7.05~7.37(7H, m), 7.52(1H, m), 7.55(1H, s), 7.84(1H, ddd, J=7.7, 1.9Hz) |
| 4 | m-methoxyphenyl | tert-butyl | 73 | −18.1 (24.5) | $C_{38}H_{52}N_4O_7S\cdot1.5H_2O$ | C: 62.02 H: 7.53 N: 7.61 S: 4.36 | C: 62.05 H: 7.16 N: 7.52 S: 4.12 | 3468, 3348(br), 1668, 1600, 1585, 1499, 1464, 1451, 1430, 1289, 1258, 1169, 1117, 1077, 1116 | 0.70~1.83(13H, m), 1.32(9H, s), 2.74~3.17(7H, m), 3.27(1H, m), 3.59(1H, dd, J=10.13Hz), 3.83(3H, s), 4.00(1H, m), 4.20(1H, m), 4.60(1H, ddd, J=7, 7, 7Hz), 4.72(1H, bs), 6.60(1H, d, J=9Hz), 6.86(1H, s), 7.04~7.55(9H, m), 7.48(1H, s) |
| 5 | p-methylphenyl | tert-butyl | 94 | −21.3 (24.0) | $C_{38}H_{52}N_4O_6S\cdot\frac{1}{2}H_2O$ | C: 64.61 H: 7.63 N: 7.93 S: 4.54 | C: 64.65 H: 7.64 N: 7.99 S: 4.61 | 3460, 3350(br), 1666, 1608, 1564, 1498, 1450, 1116 | 0.70~1.85(13H, m), 1.32(9H, s), 2.40(3H, s), 2.70~3.18(7H, m), 3.27(1H, m), 3.61(1H, dd, J=13.2, 9.8Hz), 3.75(2H, bs), 3.99(1H, m), 4.19(1H, m), 4.61(1H, ddd, J=6.5, 6.5, 6.5Hz), 6.53(1H, d, J=9.1Hz), 6.88(1H, s), 7.10~7.45(7H, m), 7.52(1H, s), 7.82(2H, d, J=8.2Hz) |
| 6 | 2,4-difluorophenyl | tert-butyl | 93 | −21.0 (23.5) | $C_{37}H_{48}F_2N_4O_6S\cdot\frac{1}{4}H_2O$ | C: 61.39 F: 5.25 H: 6.82 N: 7.74 S: 4.43 | C: 61.18 F: 5.35 H: 6.82 N: 7.76 S: 4.40 | 3470, 3350(br), 1665, 1612(1595sh), 1498, 1450, 1430, 1116, 1100, 970, 855 | 0.70~1.80(13H, m), 1.34(9H, s), 2.77~3.16(7H, m), 3.20(2H, bs), 3.25(1H, m), 3.59(1H, dd, J=13.95Hz), 3.48(1H, m), 4.18(1H, m), 4.59(1H, ddd, J=7, 7, 7Hz), 6.46(1H, d, J=9.3Hz), 6.78~7.00(2H, m), 6.91(1H, s), 7.23(5H, m), 7.54(1H, s), 7.91(1H, ddd, J=8.6, 8.6, 6.6Hz) |

TABLE 10-continued (IA)

| Compd. of Ex. No. | R¹ | R⁴ | Yield % | [α]$_D$ C = 1.0, MeOH (°C.) | Molecular formula | Elemental analysis Calcd. | Found | IR νmax cm⁻¹ | NMR (δ): |
|---|---|---|---|---|---|---|---|---|---|
| 7 | 1-naphthyl | tert-butyl | 60 | −15.3 (24.0) | $C_{41}H_{52}N_4O_6S \cdot 5/4H_2O$ | C: 65.53 H: 7.31 N: 7.46 S: 4.27 | C: 65.43 H: 7.09 N: 7.37 S: 4.24 | 3672, 3352(br), 1665, 1605, 1509, 1464, 1450, 1441, 1369, 1291, 1117, 1077 | 0.70~1.85(13H, m), 1.30(9H, s), 2.82(1H, dd, J=13.2, 8.4Hz), 2.90~3.18(6H, m), 3.28(1H, m), 3.59(1H, dd, J=13.0, 10.0Hz), 4.03(1H, m), 4.24(1H, m), 4.60(1H, ddd, J=5, Hz), 5.30(1H, m), 6.63(1H, d, J=9.2Hz), 6.83(1H, s), 7.20(5H, m), 7.50(4H, m), 7.90(2H, m), 7.86(1H, s), 8.60(1H, d, J=7.6Hz) |
| 8 | 3-thienyl | tert-butyl | 94 | −24.4 (28.0) | $C_{35}H_{48}N_4O_6S_2 \cdot H_2O$ | C: 59.81 H: 7.17 N: 7.97 S: 9.12 | C: 59.68 H: 7.02 N: 8.23 S: 9.10 | 3460, 3350(br), 1662, 1600, 1505, 1446, 1113 | 0.70~1.85(13H, m), 1.33(9H, s), 2.77~3.18(7H, m), 3.26(1H, m), 3.59(1H, dd, J=13.2, 10.2Hz), 3.97(1H, m), 4.18(1H, m), 4.58(1H, m), 6.44(1H, d, J=9.4Hz), 6.88(1H, s), 7.12~7.47(6H, m), 7.50(1H, s), 7.51(1H, dd, J=5.0, 1.2Hz), 8.13(1H, dd, J=1.2, 3Hz) |
| 9 | 2-thiazolyl | tert-butyl | 71 | | | $C_{34}H_{47}N_5O_6S_2 \cdot 2H_2O \cdot \frac{1}{4}C_4H_8O_2$ | C: 56.45 H: 7.24 N: 9.16 S: 8.37 | C: 56.41 H: 6.95 N: 9.14 S: 8.09 | 3360, 3356(br), 1661, 1599, 1511, 1446, 1113 | 0.70~1.83(13H, m), 1.34(9H, s), 2.74~3.32(8H, m), 3.61(1H, dd, J=12.8, 9.4Hz), 3.73(2H, bs), 3.95(1H, m), 4.23(1H, m), 4.60(1H, ddd, J=6.6, 6.6, 6.6Hz), 6.51(1H, d, J=9.2Hz), 6.96(1H, s), 7.12~7.35(5H, m), 7.57(1H, s), 7.68(1H, d, J=3Hz), 8.00(1H, dd, d, J=3Hz) |

(IA)

| Compd. of Ex. No. | R¹ | Yield % | [α]$_D$ C = 1.0, MeOH (°C.) | Molecular formula | Calcd. | Found | IR νmax cm⁻¹ | [IA] NMR (δ) |
|---|---|---|---|---|---|---|---|---|
| 10 | m-fluorophenyl | 88 | −21.4 (24.0) | $C_{37}H_{49}N_4FO_6S \cdot \frac{1}{2}H_2O$ | C: 62.56 F: 2.67 H: 7.17 N: 7.89 S: 4.51 | C: 62.72 F: 2.60 H: 7.14 N: 7.67 S: 4.60 | 3470, 3340, 1663, 1605, 1590, 1496, 1445, 1400, 1370, 1115, 1075, 1015 | 0.70~1.82(13H, m), 1.33(9H, s), 2.75~3.19(7H, m), 3.28(1H, m), 3.62(1H, dd, J=13.10Hz), 4.02(1H, m), 4.20(1H, m), 4.59(1H, ddd, J=6.4, 6.4, 6.4Hz), 6.55(1H, d, J=9.4Hz), 6.92(1H, m), 7.25(6H, m), 7.45(2H, m), |

TABLE 10-continued

| Compd. of | | | Yield | [α]_D* | | | |
|---|---|---|---|---|---|---|---|
| 11 | p-fluorophenyl | 87 | −21.3 (24.0) | C₃₇H₄₉N₄FO₆S.½H₂O | C: 62.56 H: 7.17 N: 7.89 S: 4.51 | C: 62.60 F: 2.66 H: 7.17 N: 7.84 S: 4.62 | 3470, 3340, 1665, 1600, 1505, 1450, 1410, 1370, 1156, 1115, 1076 | 7.56(1H, s), 7.62(1H, m), 7.70(1H, d, J=7.6Hz), 0.70~1.82(13H, m), 1.33(9H, s), 2.75~3.20(7H, m), 3.28(1H, m), 3.57(2H, bs), 3.60(1H, dd, J=13,10Hz), 4.00(1H, m), 4.19(1H, m), 4.59(1H, ddd, J=6.6, 6.6, 6.6Hz), 6.54(1H, d, J=9.2Hz), 6.90(1H, s), 7.14(2H, dd, J=17.2, 8.8Hz), 7.26(6H, m), 7.48(1H, d, J=8Hz), 7.54(1H, s), 7.96(2H, dd, J=9.5, 4Hz) |
| 12 | 2,6-difluorophenyl | 75 | −23.4 (23.5) | C₃₇H₄₈N₄F₂O₆S.½H₂O | C: 61.15 H: 6.84 N: 7.71 S: 4.41 | C: 61.05 F: 5.26 H: 6.60 N: 7.77 S: 4.75 | 3468, 3360, 1664, 1624, 1502, 1467, 1450, 1402, 1370, 1290, 1117, 1078, 1016, 991 | 0.70~1.85(13H, m), 1.33(9H, s), 2.78~3.18(7H, m), 3.25(1H, m), 3.61(1H, dd, J=13.2, 9.8Hz), 3.95(1H, m), 4.12(1H, m), 4.58(1H, ddd, J=6.4, 6.4, 6.4Hz), 5.68(2H, bs), 6.55(1H, d, J=9.4Hz), 6.85(1H, s), 6.93(2H, t, J=8.2Hz), 7.15~7.48(7H, m), 7.49(1H, s) |
| 13 | o-methoxyphenyl | 75 | −3.3 (24.0) | C₃₈H₅₂N₄O₇S.½H₂O | C: 63.18 H: 7.46 N: 7.76 S: 4.44 | C: 63.18 H: 7.52 N: 7.38 S: 4.03 | 3468, 3360, 1665, 1600, 1502, 1487, 1465, 1438, 1289, 1163, 1117, 1077, 1026 | 0.70~1.82(13H, m), 1.33(9H, s), 2.75~3.35(8H, m), 3.62(1H, dd, J=14, 10Hz), 3.87(3H, s), 3.95(1H, m), 4.15(1H, m), 4.62(1H, ddd, J=6.5, 6.5, 6.5Hz), 6.66(1H, d, J=9.4Hz), 6.82(1H, s), 6.85(2H, m), 7.24(5H, m), 7.46(1H, s), 7.46(1H, td, J=7.8, 1.8Hz), 7.70(1H, dd, J=7.8, 1.8Hz) |
| 14 | o-chlorophenyl | 75 | −8.4 (23.5) | C₃₇H₄₉ClN₄O₆S. 0.1 CH₂Cl₂.½H₂O | C: 61.23 H: 6.91 N: 7.70 S: 4.41 | C: 61.03 Cl: 5.63 H: 6.85 N: 7.68 S: 4.31 | 3468, 3360, 1665, 1593, 1500, 1450, 1434, 1402, 1370, 1291, 1117, 1077 | 0.70~1.80(13H, m), 1.33(9H, s), 2.78~3.17(7H, m), 3.26(1H, m), 3.52(1H, dd, J=13, 9.8Hz), 3.97(1H, m), 4.13(1H, m), 4.57(1H, ddd, J=6.7, 6.7, 6.7Hz), 6.52(1H, d, J=9.0Hz), 6.85(1H, s), 7.14~7.42(8H, m), 7.46(1H, s), 7.53(1H, m) |
| 15 | m-cyanophenyl | 92 | −20.6 (24.5) | C₃₈H₄₉N₅O₆S. H₂O.½CH₂Cl₂ | C: 61.82 H: 6.99 N: 9.42 S: 4.31 | C: 61.87 H: 6.75 N: 9.40 S: 4.25 | 3468, 3360, 2236, 1666, 1602, 1499, 1450, 1431, 1401, 1370, 1288, 1150, 1117, 1077, 909 | 0.70~1.80(13H, m), 1.33(9H, s), 2.77~318(7H, m), 3.29(1H, m), 3.61(1H, dd, J=12.8, 9.8Hz), 4.04(1H, m), 4.22(1H, m), 4.57(1H, ddd, J=5.8, 5.8, 5.8Hz), 6.59(1H, d, J=9Hz), 6.91(1H, s), 7.23(5H, m), 7.56(1H, s), 7.58(1H, t, J=7.8Hz), 7.81(1H, d, J=7.8Hz), 8.14(1H, d, J=8Hz), 8.23(1H, s) |
| 16 | o-methylsulfonyl-aminophenyl | 86 | −11.4 (24.0) | C₃₈H₅₃N₅O₈S₂. ½(iPr)₂O.½H₂O | C: 58.82 H: 7.19 N: 8.68 S: 7.95 | C: 58.54 H: 7.06 N: 8.46 S: 7.71 | 3464, 3352, 1664, 1607, 1578, 1492, 1452, 1400, 1340, 1289, 1155, 1117, 1077, 968, 917 | 0.70~1.82(13H, m), 1.33(9H, s), 2.75~3.17(7H, m), 3.26(1H, m), 3.59(1H, dd, J=13, 10.4Hz), 4.01(1H, m), 4.16(1H, m), 4.57(1H, ddd, J=6.4, 6.4, 6.4Hz), 6.59(1H, d, J=9.2Hz), 6.88(1H, s), 7.20(6H, m), 7.49(1H, d, J=1.2Hz), 7.50(2H, m), 7.69(1H, dd, J=8.4, 1.2Hz), 7.86(1H, dd, J=8.2, 1.2Hz) |
| 17 | p-trifluoromethyl-phenyl | 95 | −18.8 (24.0) | C₃₈H₄₉F₃N₄O₆S.½H₂O | C: 60.38 F: 7.54 H: 6.67 N: 7.41 S: 4.24 | C: 60.27 F: 7.53 H: 6.77 N: 7.27 S: 4.41 | 3450, 3350, 1665, 1605, 1510, 1450, 1410, 1325, 1170, 1135, 1115, 1065 | 0.70~1.80(13H, m), 1.32(9H, s), 2.75~3.18(7H, m), 3.27(1H, m), 3.58(1H, dd, J=13.4, 10Hz), 4.04(1H, m), 4.21(1H, td, J=7, 2.5Hz), 4.57(1H, ddd, J=6.3, 6.3, 6.3Hz), 6.54(1H, d, J=9.4Hz), 7.25(5H, m), 7.52(1H, d, J=9Hz), 7.71(2H, d, J=8.2Hz), 8.04(2H, d, J=8Hz) |

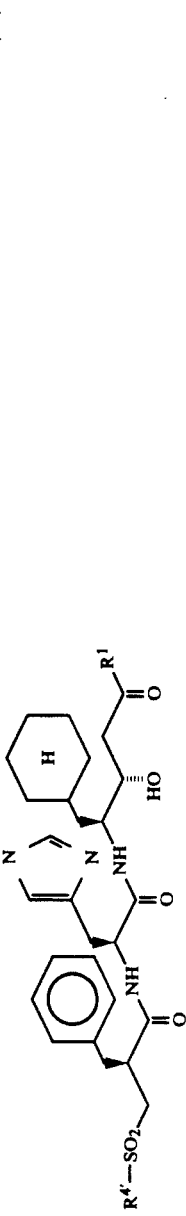

[IA]

TABLE 10-continued

| Ex. No. | R¹ | R⁴ | Yield % | $[\alpha]_D$ (C = 1.0, MeOH) | Molecular formula | Calcd. | Found | IR νmax cm⁻¹ | NMR (δ) |
|---|---|---|---|---|---|---|---|---|---|
| 18 | m-morpholino-carbonyloxyphenyl | tert-butyl | 92 | −15.8 ± 0.6 (25° C.) | $C_{42}H_{57}N_5O_9S \cdot 1\frac{1}{2}H_2O$ | C: 60.09 H: 7.26 N: 8.34 S: 3.82 | C: 59.93 H: 6.94 N: 8.38 S: 3.79 | 3470, 3320, 1711, 1680, 1665, 1605, 1587, 1500, 1420, 1370, 1116, 1068 | 0.70~1.83(13H, m), 1.34(9H, s), 2.70~3.15(7H, m), 3.28(1H, m), 3.48~3.82(8H, m), 3.88(1H, m), 4.14(1H, m), 4.63(1H, ddd, J=6.6, 6.6, 6.6Hz), 6.39(1H, d, J=8.6Hz), 6.80(1H, s), 7.17~7.40(6H, m), 7.40~7.60(3H, m), 7.77(1H, d, J=7.6Hz) |
| 19 | m-morpholino-carbonylphenyl | tert-butyl | 79 | −15.8 ± 0.6 (25° C.) | $C_{42}H_{57}N_5O_8S \cdot 5/4H_2O$ | C: 61.93 H: 7.36 N: 8.60 S: 3.94 | C: 61.70 H: 7.10 N: 8.42 S: 3.92 | 3356, 1665, 1627, 1581, 1498, 1463, 1451, 1369, 1289, 1117, 1075, 1028 | 0.70~1.80(13H, m), 1.33(9H, s), 2.63~3.17(7H, m), 3.30(1H, m), 3.38~3.95(10H, m), 4.18(1H, m), 4.63(1H, ddd, J=6, 6, 6Hz), 6.49(1H, m), 6.86(1H, s), 7.23(6H, m), 7.56(1H, s), 7.66(1H, m), 7.71(1H, d, J=6Hz), 7.84(1H, s), 8.00(1H, m) |
| 20 | 3,4-methylene-dioxyphenyl | tert-butyl | 88 | −16.8 ± 0.6 (25° C.) | $C_{38}H_{50}N_4O_8S \cdot 2H_2O \cdot 2/5$ dioxane | C: 59.89 H: 7.26 N: 7.05 S: 4.04 | C: 59.86 H: 6.92 N: 6.77 S: 3.87 | 3470, 3340, 1665, 1605, 1505, 1490, 1445, 1117, 1080, 1042 | 0.70~1.82(13H, m), 1.34(9H, s), 2.78~3.18(7H, m), 3.26(1H, m), 3.60(1H, dd, J=13, 9.8Hz), 3.97(1H, m), 4.17(1H, m), 4.60(1H, ddd, J=6.4, 6.4, 6.4Hz), 6.04(2H, s), 6.45(1H, d, J=9.4Hz), 6.84(2H, d, J=8.2Hz), 6.86(1H, s), 7.25(5H, m), 7.39(1H, d, J=1.2Hz), 7.49(1H, s), 7.51(2H, d, J=8.2Hz) |
| 21 | cyclohexyl | tert-butyl | 94 | −21.2 ± 0.6 (24° C.) | $C_{37}H_{56}N_4O_6S \cdot \frac{1}{2}H_2O$ | C: 62.42 H: 8.35 N: 7.87 S: 4.50 | C: 62.42 H: 8.06 N: 8.10 S: 4.33 | 3460, 3340, 1662(sh1685), 1065, 1500, 1450, 1115 | 0.70~1.92(23H, m), 1.35(9H, s), 2.36(1H, s), 2.55(2H, m), 2.75~3.18(5H, m), 3.26(1H, m), 3.60(1H, dd, J=13.3, 9.8Hz), 3.88(1H, m), 3.99(1H, m), 4.56(1H, ddd, J=6, 6, 6Hz), 6.41(1H, d, J=9.2Hz), 6.88(1H, s), 7.27(5H, m), 7.54(1H, s) |
| 22 | p-methoxyphenyl | tert-butyl | 91 | −16.9 ± 0.6 (24° C.) | $C_{38}H_{52}N_4O_7S \cdot 2.5H_2O \cdot \frac{1}{2}$ dioxan | C: 60.21 H: 7.71 N: 7.02 S: 4.02 | C: 60.24 H: 7.38 N: 6.78 S: 3.77 | 3470, 3340, 1665, 1603, 1575, 1510, 1170, 1116, 1076, 1030 | 0.70~0.83(13H, m), 1.34(9H, s), 2.75~3.17(7H, m), 3.15(1H, m), 3.60(1H, dd, J=13, 9.6Hz), 3.87(3H, s), 3.98(1H, m), 4.18(1H, m), 4.61(1H, ddd, J=6.8, 6.8, 6.8Hz), 6.44(1H, d, J=9.2Hz), 6.86(1H, s), 6.93(2H, d, J=9Hz), 7.25(5H, m), 7.49(1H, s), 7.91(2H, d, J=8.6Hz) |
| 37 | phenyl | isopropyl | 93 | −21.2 ± 0.6 (24° C.) | $C_{36}H_{48}N_4O_6S \cdot H_2O$ | C: 63.32 H: 7.38 N: 8.20 S: 4.69 | C: 63.59 H: 7.46 N: 8.01 S: 4.48 | 3460, 3340, 1665, 1600, 1580, 1500, 1450, 1120 | 0.70~1.85(13H, m), 1.23(3H, d, J=6.8Hz), 1.30(3H, d, J=6.8Hz), 2.70~3.18(8H, m), 3.22(1H, m), 3.56(1H, dd, J=13.4, 9.6Hz), 4.01(1H, m), 4.20(1H, m), 4.60(1H, ddd, J=6.6Hz), 6.49(1H, d, J=9.2Hz), 6.87(1H, s), 7.22(5H, m), 7.50(4H, m), 7.93(2H, d, J=6.8Hz) |
| 38 | phenyl | ethyl | 89 | −22.1 ± 0.6 (24° C.) | $C_{35}H_{46}N_4O_6S \cdot \frac{1}{2}H_2O$ | C: 63.28 H: 7.21 N: 8.43 S: 4.83 | C: 63.17 H: 7.18 N: 8.49 S: 4.60 | 3400, 3350, 1665, 1600, 1582, 1510, 1450, 1310, 1123 | 0.70~1.85(13H, m), 1.23(3H, t, J=7.4Hz), 2.65(8H, m), 3.23(1H, m), 3.57(1H, dd, J=14, 9.8Hz), 4.03(1H, m), 4.19(1H, m), 4.62(1H, ddd, J=6.2, 6.2, 6.2Hz), 6.56(1H, d, J=9.2Hz), 6.88(1H, s), 7.20(5H, m), 7.45(1H, d, J=1.6Hz), 7.52(3H, m), 7.93(2H, d, J=6.8Hz) |

Compd. of

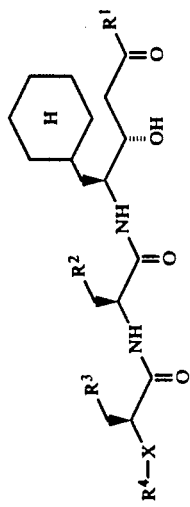

[IA]

$[\alpha]_D^*$
(C = 1.0, MeOH)

Yield    Molecular

TABLE 10-continued

| Ex. No. | R¹ | R² | R⁴ | X | % | [α]ᴅ (Temp. °C.) | formula | Calcd. | Found | IR νmax cm⁻¹ | R³ | NMR (δ) |
|---|---|---|---|---|---|---|---|---|---|---|---|---|
| 28 | m-(N-methyl)-aminophenyl | (thiazolyl-methyl) | N-morpholino-sulfonyl | NH | 52 | −25.5 (25) | $C_{37}H_{50}N_6O_7S_2 \cdot \frac{1}{2}H_2O \cdot 2/5 CH_2Cl_2$ | C: 56.09 H: 6.56 N: 10.49 S: 8.01 | C: 56.16 H: 6.33 N: 10.24 S: 7.64 | 13380, 1667, 1604, 1584, 1508, 1454, 1448, 1410, 1339, 1294, 1261, 1156, 1113, 1071 | phenyl | 0.65~1.77(13H, m), 2.50(2H, m), 2.80(3H, m), 2.89(3H, s), 3.00(2H, m), 3.20(1H, dd, J=5, 15Hz), 3.40(4H, m), 3.53(1H, dd, J=5, 15Hz), 3.95(2H, m), 4.12(1H, m), 4.80(1H, dt, J=4.4, 7.0Hz), 5.18(1H, dt, J=6Hz), 6.62(1H, d, J=9.4Hz), 6.82(1H, dt, J=2.2, 7Hz), 7.14(1H, d, J=2Hz), 7.30(8H, m), 8.81(1H, d, J=2Hz), 9.09(1H, d, J=6.8Hz) |
| 33 | phenyl | (thiazolyl-methyl with NH₂) | ter-butyl-sulfonyl | CH₂ | 44 | −24.9 (23.5) | $C_{38}H_{50}N_4O_6S_2 \cdot \frac{1}{2}H_2O$ (157-159°) | C: 62.11 H: 7.12 N: 7.83 S: 8.96 | C: 62.10 H: 7.24 N: 7.95 S: 8.70 | 3490, 3400, 1665, 1605, 1580, 1510, 1450, 1115 | phenyl | 0.70~1.82(13H, m), 1.31(9H, s), 2.83~3.30(9H, m), 3.47(1H, dd, J=4.6, 13.2Hz), 4.01(1H, m), 4.16(1H, dt, J=3, 6.2Hz), 4.60(1H, ddd, J=4.8Hz×3), 5.30(1H, bs), 6.24(1H, s), 6.49(1H, d, J=9.8Hz), 7.25(5H, m), 7.47(2H, t, J=7.4Hz), 7.56(1H, d, J=7Hz), 7.62(1H, d, J=6.8Hz), 7.96(2H, dd, J=1.4, 6.6Hz) |
| 40 | phenyl | (imidazolyl-methyl) | N-morpholino-carbonyl | CH₂ | 79 | −15.8 (25) | $C_{42}H_{51}N_5O_6 \cdot 2H_2O \cdot 2/5 CH_2Cl_2$ | C: 64.31 H: 7.10 N: 8.84 | C: 64.38 H: 6.82 N: 8.97 | 3460, 3400, 3310, 1662, 1630, 1600, 1580, 1510, 1490, 1450, 1115, 1070 | naphthyl | 0.78~1.80(13H, m), 2.56(2H, m), 2.90~3.70(15H, m), 4.04(1H, m), 4.21(1H, m), 4.64(1H, ddd, J=6.2Hz), 6.68(1H, d, J=10Hz), 6.87(1H, s), 7.26~7.59(9H, m), 7.76(1H, d, J=8.2Hz), 7.87(1H, m), 8.02(3H, m) |
| 42 | 4-pyridyl | (imidazolyl-methyl) | N-morpholino carbonyl | CH₂ | 79 | −19.3 (25) | $C_{41}H_{50}N_6O_6 \cdot H_2O \cdot \frac{1}{2} Pr_2O$ | C: 66.73 H: 7.51 N: 10.61 | C: 66.54 H: 7.54 N: 10.66 | 3460, 3400, 3320, 1660(sh1690), 1625, 1520, 1490, 1460, 1445, 1410, 1115 | naphthyl | 0.67~1.77(13H, m), 2.47(1H, dd, J=7.5, 17Hz), 2.62(1H, dd, J=5, 18Hz), 2.88~3.76(15H, m), 4.08(1H, m), 4.17(1H, m), 4.63(1H, ddd, J=5Hz), 6.77(1H, d, J=10Hz), 6.88(1H, s), 7.29(1H, d, J=7.5Hz), 7.40(1H, t, J=7.5Hz), 7.54(3H, m), 7.80(2H, d, J=6.2Hz), 7.80(2H, m), 8.04(1H, m), 8.33(1H, m), 8.76(2H, d, J=6Hz) |

EXAMPLES 53

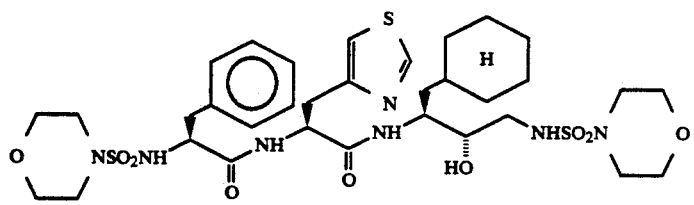

To the compound [25a] (24.5 g, 41.6 mmol) are added anisole (89.7 g, 20 eq) and anhydrous dichloromethane (250 ml). To the mixture is dropwise added trifluoroacetic acid (250 ml) with stirring and ice-cooling over 30 minutes, and the mixture is stirred at room temperature for one hour. The reaction mixture is concentrated in vacuo, made alkaline with $Na_2CO_3$ and saturated aqueous sodium bicarbonate, and extracted with a mixture of dichloromethan (9:1). The organic layer is washed with water, dried over $MgSO_4$, and evaporated to dryness in vacuo. The residue is subjected to silica gel chromatography ($SiO_2$: 600 g, $CH_2Cl_2$:MeOH:$NH_4OH$=90:10:1) to obtain the compound [26a] (14.63 g, 72%).

To the above compound [26a] (11.04 g, 22.5 mmol) are added N-(morpholinosulfonyl)phenylalanine [12a] (8.5 g, 1.2 eq), HOBt (3.96 g, 1.25 eq), and anhydrous $CH_3CN$ (200 ml). To the mixture is added DCC (6.05 g, 1.3 eq) with stirring and ice-cooling, and the mixture is stirred at 0° C. for one hour and then at room temperature for additional one hour. The reaction mixture is added with ethyl acetate and filtered. The filtrate is concentrated in vacuo and subjected to silica gel chromatography ($SiO_2$: 600 g, $CH_2Cl_2$:MeOH=97:3). Relevant fractions are combined and treated with isopropyl ether to give the compound [Ib] (16.33 g, 92%).

Elemental analysis (as $C_{33}H_{51}N_{51}N_7O_9S_3 \cdot 0.75$-$H_2O \cdot 1.0CH_2Cl_2$); Calcd.: C: 49.20; H: 6.57; N: 12.13; S 11.90; Found: C: 49.05; H: 6.20; N: 11.92; S 11.78.

$[\alpha]_D = -22.5$ (c=1; MeOH; 24° C.) IR: 3370, 2720, 1665, 1530, 1510, 1454, 1340, 1330, 1260, 1155, 1113, 1073, 943.

NMR(δ): 0.72(3H,m), 1.12(6H,m), 4.16(1H,bd,J=8Hz), 1.62(3H,bd,J=8Hz), 2.21(1H,bs), 2.47(2H,m), 2.74(1H,dd,J=10.14Hz), 2.80-3.33(4H,m), 3.21(4H,m),3.33-3.62(8H,m), 3.75(4H,m), 3.97(2H,m), 4.68(1H,m), 5.16(1H,d,J=5.4Hz), 5.64(1H,t,J=6.8Hz), 6.55(1H,d,J=9.2Hz), 7.19(1H,d,J=1.2Hz), 7.35(5H,m), 8.90(1H,d,J=1.2Hz), 9.40(1H,d,J=6.8Hz).

EXAMPLES 54-71

In accordance with substantially the same procedure as disclosed in Example 53, the compounds of the invention listed in Table 11 are obtained.

TABLE 11

$$[12] + [26] \xrightarrow{\text{DCC, HOBt}} [1B]$$

| Compd. of Ex. No. | R¹ | R² | R³ | X | R⁴ | Yield % | $[\alpha]_D^0$ C = 1, MeOH (°C.) | Molecular formula | Elemental analysis [1B] | | IR νmax cm⁻¹ |
|---|---|---|---|---|---|---|---|---|---|---|---|
| | | | | | | | | | Calcd. | Found | |
| 54 | morpholino-N- | thiazole-CH₃ | | NH | morpholino-NSO₂- | 82 | −38.4 (24.0) | C₃₇H₅₃N₇O₉ S₃ ·0.75H₂O ·0.33(ipr)₂O | C: 53.01 H: 6.75 N: 11.10 S: 10.89 | C: 52.83 H: 6.48 N: 10.96 S: 10.75 | 3370, 2920, 1730, 1665, 1600, 1530, 1510, 1400, 1340, 1260, 1155, 1115, 1072, 940 |
| 55 | morpholino-N- | thiazole-CH₃ | methylnaphthyl | NH | CH₃-C(O)-CH₂-N-morpholine | 83 | 15.3 (24) | C₃₉H₅₅N₇O₈ S₃ ·0.66H₂O ·0.25CH₂Cl₂ | C: 55.65 H: 6.76 N: 11.57 S: 7.57 | C: 55.62 H: 6.54 N: 11.41 S: 7.18 | 3340, 2920, 1670, 1600, 1530, 1510, 1505, 1335, 1261, 1155, 1116, 1075 |
| 56 | −NMe₂ | thiazole-CH₃ | phenyl-CH₃ | NH | morpholino-NSO₂- | 98 | −22.9 (25.0) | C₃₁H₄₉N₇O₈ S₃ ·0.5H₂O ·0.25CH₂Cl₂ | C: 48.48 H: 6.58 N: 12.66 S: 12.42 | C: 48.59 H: 6.48 N: 12.28 S: 11.37 | 3370, 2920, 1665, 1604, 1530, 1510, 1400, 1328, 1260, 1153, 1113, 950 |
| 57 | −NMe₂ | thiazole-CH₃ | phenyl-CH₃ | NH | tBu-SO₂- | 89 | −7.4 (24.0) | C₃₂H₅₁N₅O₇ S₃ ·0.2H₂O ·0.1(ipr)₂O | C: 53.80 H: 7.31 N: 9.62 S: 13.22 | C: 53.61 H: 7.25 N: 9.40 S: 12.73 | 3360, 2920, 1660, 1530, 1510, 1448, 1325, 1290, 1145, 1115, 955 |
| 58 | pyridyl-CH₃ | thiazole-CH₃ | phenyl-CH₃ | NH | morpholino-NSO₂- | 92 | −23.7 (25.0) | C₃₄H₄₇N₇O₈ S₃ ·0.5H₂O ·0.25CH₂Cl₂ | C: 50.90 H: 6.05 N: 12.13 S: 11.90 | C: 50.96 H: 5.98 N: 12.10 S: 11.68 | 3380, 2930, 1665, 1605, 1577, 1530, 1512, 1415, 1340, 1260, 1160, 1115, 1075, 945 |

TABLE 11-continued

| | R³ (4-X) | R² | R⁴—X | [26] | — | Formula | Analysis | IR |
|---|---|---|---|---|---|---|---|---|
| 59 | pyridyl | thiazolyl-methyl | naphthyl, NH | 86 | −17.6 (25.0) | C₄₀H₅₁N₇O₇S₂ · 0.5H₂O · 0.25CH₂Cl₂ | C: 57.81 H: 6.33 N: 11.72 S: 7.67 / C: 57.84 H: 6.32 N: 11.69 S: 7.55 | 3330, 2920, 1670, 1599, 1575, 1580, 1505, 1336, 1165, 1115 |
| 60 | quinolinyl | thiazolyl-methyl | phenyl, CH₂-SO₂ | 70 | −15.0 (23.5) | C₃₉H₅₁N₅O₇S₃ · 0.2H₂O | C: 58.43 H: 6.46 N: 8.74 S: 12.00 / C: 58.20 H: 6.27 N: 8.59 S: 11.75 | 3360, 2920, 1615, 1600, 1567, 1530, 1500, 1450, 1330, 1290 |
| 61 | thienyl | thiazolyl-methyl | phenyl, CH₂-SO₂ | 83 | −3.4 (23.5) | C₃₄H₄₈N₄O₇S₄ · 0.75H₂O | C: 53.28 H: 6.51 N: 7.31 S: 16.73 / C: 53.04 H: 6.22 N: 7.56 S: 16.63 | 3360, 2920, 1660, 1530, 1510, 1450, 1405, 1338, 1290, 1155, 1115, 1015 |
| 62 | phenyl | thiazolyl-methyl | phenyl, CH₂-SO₂ | 72 | −3.8 (25.5) | C₃₆H₅₀N₄O₇S₃ · 0.5H₂O | C: 57.19 H: 6.80 N: 7.41 S: 12.72 / C: 57.01 H: 6.69 N: 7.41 S: 12.81 | 3360, 2920, 1660, 1605, 1530, 1510, 1446, 1330, 1290, 1160, 1165, 1145, 1116, 1115 |
| 63 | phenyl | Me-thiazolyl-methyl | phenyl, CH₂-SO₂ | 88 | −5.4 (25.5) | C₃₇H₅₂N₄O₇S₃ | C: 58.39 H: 6.89 N: 7.36 S: 12.64 / C: 58.20 H: 7.08 N: 7.32 S: 12.35 | 3440, 3360, 1662, 1605, 1585, 1510, 1450, 1330, 1290, 1160, 1115, 1095 |
| 64 | morpholinyl-propyl | thiazolyl-methyl | phenyl, NH-NSO₂-morpholine | 74 | −23.5 (25.5) | C₃₅H₅₅N₇O₉S₃ · 0.75H₂O | C: 50.80 H: 6.88 N: 11.85 S: 11.02 / C: 50.98 H: 6.86 N: 11.90 S: 11.46 | 3380, 2920, 1665, 1605, 1530, 1510, 1405, 1327, 1260, 1153, 1115, 1070 |

TABLE 11-continued

| | R³−X−⟨4−⟩−OH + H₂N−⟨12⟩−−NHSO₂R¹ --DCC, HOBt--> R⁴−X−⟨[1B]⟩−NHSO₂R¹ | | | | | | |
|---|---|---|---|---|---|---|---|
| | [12] | | [26] | | | | |
| 65 | morpholine-N-propyl | thiazole | naphthyl | NH | morpholine-acetone | 74 | −16.8 (25.5) | C₄₄H₅₉N₇O₈S₂·H₂O | C: 57.26 H: 7.15 N: 11.40 S: 7.45 | C: 57.12 H: 6.93 N: 11.21 S: 7.36 | 3330, 3000, 1670, 1597, 1525(should), 1507, 1330, 1143, 1124 |
| 66 | morpholine-N-propyl | thiazole | phenyl | NH | NSO₂− | 83 | −19.9 (25.0) | C₃₆H₅₇N₇O₉S₃·H₂O·0.33CH₂Cl₂ | C: 49.92 H: 6.88 N: 11.22 S: 11.00 | C: 49.76 H: 6.63 N: 11.10 S: 10.66 | 3380, 2930, 1665, 1605, 1530, 1510, 1325, 1263, 1155, 1116, 1075, 945 |
| 67 | morpholine-N-propyl | thiazole | naphthyl | NH | morpholine-acetone | 86 | −14.9 (25.0) | C₄₂H₆₁N₇O₈S₂·0.5CH₂Cl₂ | C: 55.69 H: 7.04 N: 10.70 S: 7.00 | C: 55.48 H: 6.86 N: 10.82 S: 6.66 | 3330, 2920, 1670, 1600, 1530, 1505, 1446, 1330, 1142, 1115 |
| 68 | NMe₂ | thiazole | phenyl | NH | NSO₂− | 80 | −23.8 (25.5) | C₃₃H₅₃N₇O₈S₃·H₂O | C: 50.17 H: 7.02 N: 12.41 S: 12.17 | C: 50.08 H: 6.80 N: 12.41 S: 11.99 | 3380, 2920, 1665, 1510, 1328, 1262, 1155, 1115 |
| 69 | CH₃ | thiazole | phenyl | CH₂ | SO₂− | 89 | −11.1 (24.0) | C₃₁H₄₈N₄O₇S₃·0.5H₂O·0.33CH₂Cl₂ | C: 52.51 H: 6.97 N: 7.58 S: 13.01 | C: 52.25 H: 6.80 N: 7.80 S: 12.51 | 3350, 2920, 1660, 1604, 1525, 1510, 1325, 1286, 1146, 1114 |
| 70 | pentyl | thiazole | phenyl | CH₂ | SO₂− | 90 | −7.0 (23.5) | C₃₄H₅₄N₄O₇S₃·0.33H₂O | C: 55.72 H: 7.52 N: 7.64 S: 13.12 | C: 55.58 H: 7.39 N: 7.57 S: 12.83 | 3360, 2920, 1660, 1605, 1530, 1510, 1450, 1325, 1290, 1140, 1115 |

TABLE 11-continued

| Compd. of Ex. No. | [IB] NMRδ |
|---|---|
| 54 | 0.74(3H, m), 1.12(6H, m), 1.42(1H, bd), 1.60(3H, bd, 7.5Hz), 1.95(2H, m), 2.05(1H, bs), 2.52(2H, m), 3.00(5H, m), 3.21(5H, m), 3.55(2H, m), 3.78(4H, m), 3.88(1H, m), 4.06~4.25(2H, m), 4.74(1H, m), 5.01(1H, d, J=4Hz), 5.62(1H, t, J=7.5Hz), 6.56(1H, d, J=9.2Hz), 7.18(1H, m), 7.45(1H, m), 7.56~7.76(2H, m), 7.87(1H, dd, J=1.4, 8.2Hz), 7.93(1H, dd, J=1, 7.8Hz), 8.23(1H, d, J=8.4Hz), 8.89(1H, d, J=6.8Hz) |
| 55 | 0.76(3H, m), 0.95~1.53(6H, m), 1.60(4H, bd), 1.80(1H, bs), 2.25(2H, m), 2.42(2H, m), 2.80(1H, m), 3.04(4H, m), 3.19(4H, m), 3.46(7H, m), 3.63(4H, m), 3.75(4H, m), 3.92(1H, dd, J=4.3, 14.3Hz), 3.93(1H, m), 4.51(1H, m), 4.70(1H, m), 5.58(1H, bt), 6.81(1H, d, J=9.5Hz), 7.16(1H, m), 7.46(2H, m), 7.59(2H, m), 7.83(2H, m), 7.89(1H, m), 8.16(1H, d, J=8.2Hz), 8.35(1H, d, J=7.0Hz), 8.61(1H, d, J=1.9Hz) |
| 56 | 0.60~2.00(13H, m), 2.48(2H, m), 2.58(1H, bs), 2.81(6H, s), 2.68~3.12(4H, m), 3.16~3.63(9H, m), 3.97(2H, m), 4.71(1H, m), 5.27(1H, bt), 5.52(1H, d, J=5.4Hz), 6.57(1H, d, J=9.2Hz), 7.20(1H, d, J=1.8Hz), 7.37(5H, m), 8.90(1H, d, J=1.8Hz), 9.37(1H, d, J=6.8Hz) |
| 57 | 0.70~1.80(13H, m), 1.34(9H, s), 2.79(6H, s), 2.82~3.53(9H, m), 3.67(1H, m), 3.94(1H, m), 4.67(1H, ddd, J=6Hz×3), 5.73(1H, bt), 6.59(1H, d, J=9.4Hz), 7.27(6H, m), 7.53(1H, d, J=6.6Hz), 8.86(1H, d, J=2) |
| 58 | 0.75(3H, m), 1.13(5H, m), 1.43(1H, m), 1.60(4H, m), 2.52(4H, m), 2.83(5H, m), 3.22(1H, dd, J=5, 15Hz), 3.44(6H, m), 3.87(1H, m), 4.03(1H, m), 4.65(1H, m), 5.33(1H, d, J=5.6Hz), 6.29(1H, t, J=6.3Hz), 6.58(1H, d, J=9.0Hz), 7.16(1H, d, J=1.8Hz), 7.33(6H, m), 7.49(1H, m), 8.20(1H, d, J=8Hz), 8.79(1H, bd), 8.85(1H, d, J=2.0Hz), 9.11(1H, bs), 9.30(1H, d, J=7.0Hz) |
| 59 | 0.73(3H, bs), 0.92~1.48(6H, m), 1.60(4H, bd), 2.26(2H, m), 2.40(2H, m), 2.73(1H, m), 3.00(4H, m), 3.44(8H, m), 3.85(1H, m), 3.86(1H, m), 4.49(1H, m), 4.63(1H, m), 6.23(1H, bt), 6.80(1H, d, J=9.2Hz), 7.15(1H, d, J=1.6Hz), 7.45(2H, m), 7.58(2H, m), 7.70~7.96(3H, m), 8.16(2H, t, J=9Hz), 8.29(1H, m), 8.58(1H, d, J=1.8Hz), 8.77(1H, m), 9.11(1H, be) |
| 60 | 0.55~1.70(13H, m), 1.35(9H, s), 2.75(2H, m), 2.85~3.60(8H, m), 4.55(1H, ddd, J=6.4Hz×3), 5.17(1H, t, J=6.7Hz), 7.11(1H, d, J=2.0Hz), 7.26(5H, m), 7.55(1H, dd, J=4.3Hz), 7.65(1H, t, J=7.8Hz), 8.05(1H, dd, J=1.4, 8.2Hz), 8.26(1H, dd, J=1.8, 8.3Hz), 8.41(1H, m), 6.79(1H, t, J=9.0Hz), 8.58(1H, d, J=2.0Hz), 9.04(1H, dd, J=1.8, 4.3Hz) |
| 61 | 0.62~1.75(13H, m), 1.34(9H, s), 2.70~3.54(10H, m), 3.62(1H, m), 3.89(1H, m), 4.61(1H, ddd, J=6.4Hz×3), 6.40(1H, t, J=6.8Hz), 6.48(1H, d, J=9.2Hz), 7.07(1H, dd, J=3.6, 5Hz), 7.25(6H, m), 7.40(1H, d, J=6.8Hz), 8.70(1H, d, J=2Hz) |
| 62 | 1.34(9H, s), 0.63~1.78(13H, m), 2.74(1H, dt, J=6.5, 13.5Hz), 2.85~3.52(8H, m), 3.58(1H, dt, J=3.5, 6.6Hz), 4.59(1H, ddd, J=6.5Hz×3), 6.21(1H, t, J=6.4Hz), 6.42(1H, d, J=9.2Hz), 7.19(1H, J=1.7Hz), 7.25(5H, m), 7.41(1H, d, J=6.8Hz), 7.52(3H, m), 7.87(2H, m), 8.66(1H, m), 8.70(1H, d, J=2.0Hz) |
| 63 | 0.60~1.75(13H, m), 1.34(9H, s), 2.63(3H, s), 2.70(1H, d, J=6.6, 13.6Hz), 2.80~3.46(9H, m), 3.53(1H, m), 3.87(1H, m), 4.47(1H, m), 5.89(1H, t, J=5.8Hz), 6.41(1H, d, J=9Hz), 6.92(1H, s), 7.28(5H, m), 7.52(3H, m), 7.63(1H, d, J=5.8Hz), 7.86(2H, dd, J=1.6, 7.7Hz) |
| 64 | 0.76(3H, m), 1.13(1.43~1.78(13H, m), 1.60(4H, bd, J=4.7Hz), 3.92(1H, m), 3.98(1H, m), 4.68(1H, m), 2.02(1H, bs), 2.52(6H, m), 7.16(1H, d, J=5.5Hz), 5.70(1H, bt, J=5Hz), 6.50(1H, bt, J=9.6Hz), 7.16(1H, d, J=2.0Hz), 2.72(1H, dd, J=10, 16Hz), 2.88(5H, bt, J=7Hz), 3.03(2H, m), 3.26(2H, m), 3.45(8H, m), 3.75(4H, t, J=6.9Hz) 7.34(5H, m), 8.87(1H, d, J=2.0Hz), 9.39(1H, d, J=6.9Hz) |
| 65 | 0.74(3H, m), 0.9~1.35(5H, m), 1.45(1H, d, J=8Hz), 1.60(4H, m), 1.98(1H, bs), 2.24(2H, m), 2.39(2H, m), 2.55(4H, m), 2.80~3.15(8H, m), 3.25(2H, t, J=7Hz), 3.30~3.68(8H, m), 3.75(4H, m), 3.90(1H, dd, J=4.4, 14.5Hz), 3.91(1H, m), 4.50(1H, m), 4.67(1H, m), 5.67(1H, bt), 6.73(1H, d, J=9.2Hz), 7.15(1H, d, J=1.4Hz), 7.46(2H, m), 7.60(2H, m), 7.76(1H, d, J=3.6Hz), 7.84(1H, m), J=2.6, 6.8Hz), 7.92(1H, m), 8.16(1H, d, J=8.4Hz), 8.34(1H, d, J=7.2Hz), 8.60(1H, d, J=2Hz) |
| 66 | 0.55~1.74(13H, m), 2.02(2H, m), 2.18(1H, m), 2.50(6H, m), 2.66~2.94(3H, m), 2.94~3.30(5H, m), 3.45(8H, m), 3.73(5H, m), 3.90(1H, m), 4.00(1H, m), 4.67(1H, m), 5.20(1H, bd), 5.78(1H, bt), 6.53(1H, d, J=9.4Hz), 7.16(1H, d, J=1.9Hz), 7.35(5H, m), 8.87(1H, d, J=2.0Hz), 9.41(1H, d, J=6.6Hz) |
| 67 | 0.62~1.75(13H, m), 2.04(2H, m), 2.20(1H, m), 2.39(2H, m), 2.51(6H, m), 2.90(3H, m), 3.10(4H, m), 3.43(6H, m), 3.57(4H, m), 3.73(4H, m), 3.90(2H, m), 4.50(1H, m), 4.69(1H, m), 5.76(1H, m), 6.77(1H, d, J=9Hz), 7.16(1H, m), 7.44(2H, m), 7.60(2H, m), 7.76(1H, d, J=1.4Hz), 7.85(1H, d, J=3.2Hz), 7.90(1H, m), 8.16(1H, d, J=8Hz), 8.37(1H, d, J=6.8Hz), 8.60(1H, d, J=2Hz) |

TABLE 11-continued

[Reaction scheme: Structure [12] (R³-CH(NH-C(O)-CH(R²)-NH-CH(CH₂-cyclohexyl)-CH(OH)-CH₂-NHSO₂R¹)-X-4-COOH + H₂N-structure [26]) → via DCC, HOBt → Structure [IB] (R⁴-X-CH(R³)-C(O)-NH-CH(R²)-C(O)-NH-CH(CH₂-cyclohexyl)-CH(OH)-CH₂-NHSO₂R¹)]

| | |
|---|---|
| 68 | 0.73(3H, m), 1.15(5H, m), 1.43(1H, bd, J=8Hz), 1.61(4H, bd, J=6Hz), 2.31(6H, s), 2.50(2H, m), 2.74(1H, dd, J=10, 14Hz), 2.83(5H, m), 3.04(2H, m), 3.26(2H, m), 3.45(7H, m), 3.90(1H, m), 4.02(1H, dd, J=2.8, 10.4Hz), 4.69(1H, m), 5.23(1H, bs), 6.51(1H, d, J=9Hz), 7.17(1H, d, J=1.6Hz), 7.35(5H, m), 8.87(1H, d, J=2Hz), 9.32(1H, d, J=7Hz) |
| 69 | 0.70~1.80(13H, m), 1.35(9H, s), 2.96(3H, s), 2.75(1H, bs), 2.87(~3.50(9H, m), 3.65(1H, m), 3.45(1H, m), 4.63(1H, ddd, J=5.8Hz), 5.78(1H, t, J=6.6Hz), 6.50(1H, d, J=9.2Hz), 7.28(6H, m), 7.60(1H, d, 6.2Hz), 8.77(1H, d, J=2Hz) |
| 70 | 0.70~1.88(17H, m), 0.95(3H, t, J=7.2Hz), 2.87~3.52(12H, m), 3.63(1H, m), 3.94(1H, m), 4.63(1H, ddd, J=6.2Hz×3), 5.68(1H, t, J=6.4Hz), 6.45(1H, d, J=9Hz), 7.25(6H, m), 7.54(1H, d, J=6.4Hz), 8.76(1H, d, J=2Hz) |
| 71 | 0.64~1.88(17H, m), 0.94(3H, t, J=7.2Hz), 2.28(1H, dd, J=6.4, 16.6Hz), 2.60~3.80(19H, m), 4.04(1H, m), 4.70(1H, ddd, J=4.7Hz×3), 5.57(1H, t, J=6.8Hz) |

Renin inhibition potency of the compounds (I) of the invention was determined in vitro and in vivo according to the procedure described in the following Experiments.

Experiment 1 Potency in vitro

Commercially available lyophilized human plasma (Ortho, Bi-Level Plasma Renin Control) was renatured by dissolving in water. Angiotensinogen was allowed to react with intrinsic renin contained in the renatured plasma to generate angiotensin I (AI), which was quantitatively measured with radioimmunoassay (RIA). Thus, potency of the plasma renin was determined on the basis of the AI production. For this purpose, Renin RIA kit (RENIN' RIABEAD®) manufacture by Dinabott was used. All of the reagents necessary for the measurement of the AI production were available from the attachment of the kit, and the measurement was conducted according to the manufacturer's direction.

To the plasma (0.2 ml) were added all of the reagents, and the mixture was combined with either of sample solutions (0.002 ml) of various concentrations which had been prepared by dissolving a test compound in different amount of ethanol. Ethanol (0.002 ml) containing no test compound was used as a control solution. The amount of AI produced was measured after 60 minutes incubation. Renin inhibition potency of test compound was determined by comparing the amount of AI produced by a sample solution with that produced by a control solution. The concentrations of the test compounds which inhibit renin activity by 50% ($IC_{50}$) are summarized in Table 11.

TABLE 11

| | Renin Inhibition in vitro | | | | |
|---|---|---|---|---|---|
| Test Compound (Example No.) | $IC_{50}$ | Test Compound (Example No.) | $IC_{50}$ | Test Compound (Example No.) | $IC_{50}$ |
| 1 | 6.09 | 22 | 39.2 | 42 | 13 |
| 2 | 5.87 | 23 | 2.07 | 43 | 0.51 |
| 3 | 4.44 | 24 | 1.56 | 44 | 1.53 |
| 4 | 3.21 | 25 | 3.17 | 45 | 0.31 |
| 5 | 29.0 | 26 | 1.32 | 46 | 3.16 |
| 6 | 4.22 | 27 | 1.78 | 47 | 5.90 |
| 8 | 6.17 | 28 | 0.52 | 48 | 1.98 |
| 9 | 12.0 | 29 | 3.31 | 49 | 2.34 |

TABLE 11-continued

| | Renin Inhibition in vitro | | | | |
|---|---|---|---|---|---|
| Test Compound (Example No.) | $IC_{50}$ | Test Compound (Example No.) | $IC_{50}$ | Test Compound (Example No.) | $IC_{50}$ |
| 10 | 10.9 | 30 | 1.07 | 50 | 14.8 |
| 11 | 9.1 | 31 | 11.6 | 51 | 4.51 |
| 12 | 4.56 | 32 | 6.72 | 52 | 1.69 |
| 13 | 53.9 | 33 | 4.65 | 53 | 0.36 |
| 14 | 9.3 | 34 | 9.53 | 55 | 0.60 |
| 15 | 12.6 | 35 | 0.63 | 56 | 0.70 |
| 16 | 71.3 | 36 | 4.98 | 57 | 0.80 |
| 17 | 259 | 37 | 14.5 | 58 | 0.19 |
| 18 | 22.8 | 38 | 39.2 | 59 | 0.41 |
| 19 | 3.75 | 39 | 7.52 | 62 | 1.24 |
| 20 | 7.36 | 40 | 18.1 | 64 | 0.70 |
| 21 | 2.73 | 41 | 4.98 | 69 | 0.53 |
| | | | | (1)(KRI-1314) | 21.3 |
| | | | | (2)(ES-6864) | 3.75 |

$IC_{50}$ nM (1) KRI-1314

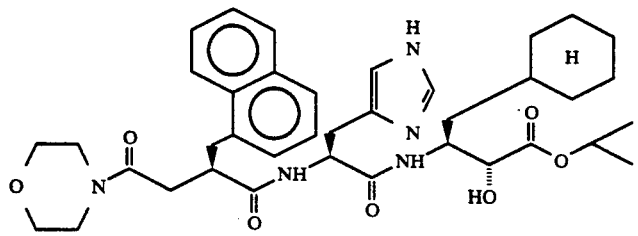

(2) ES-6864

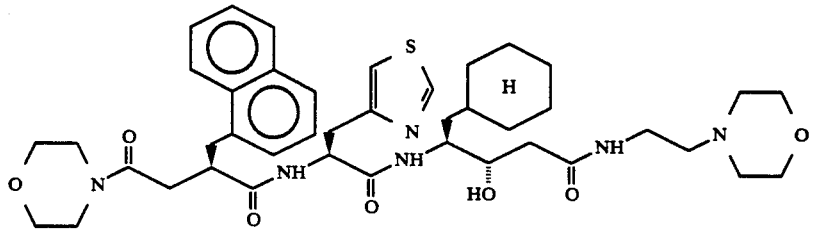

Experiment 2 Potency in vivo

Crab-eating monkeys (Cynomolgus monkeys) (2.8–5.0 kg) were fed on low sodium diet (Na 7.15 mg/100 g feed) for six days, during which the monkeys intramuscularly received furosemide (2 mg/kg body weight) every other day from the second day of the experiment, in order to make the monkeys hyperrenin condition.

After seven days from the low sodium feeding, the monkeys were restrained on a monkey chair. Compounds to be tested are dissolved in 0.1 M citric acid/physiological saline or suspended in water with addition of β-cyclodextrin, and orally administered to the monkeys using a stomach probe (15 mg/kg body weight). Two milliliters of blood was collected from femoral vein before administration of the compounds and 0.5, 1.5, 2.5 and 4 hours after the administration. For the blood collection, an injection syringe containing 30 μl of 6% aqueous EDTA·2Na solution was used. The collected blood was transferred into a test tube and centrifuged (3000 rpm, 10 minutes) at 4° C., and the resultant supernatant was used to determine the renin content. Plasma renin activity (AI(ng)/ml/h value) was measured using Radioimmunoassy kit commercially available from Dinabott Co. in the same manner as in the foregoing in vitro test. Renin inhibition potencies of the compounds tested, which were expressed as a percentage of renin activity relative to the activity before the administration, are listed in Table 12.

TABLE 12

| Compound Example No. | Max | Mean | 4 h | 6 h | 8 h | 24 h |
|---|---|---|---|---|---|---|
| 1 | 33 | 22 | 22 | | | |
| 2 | 49 | 46 | 49 | | | |
| 8 | 60 | 52 | 60 | | | |
| 21 | 55 | 37 | 55 | | | |
| 24 | 99 | 90 | 77 | 56 | 42 | 28 |
| 26 | 83 | 71 | 69 | 99 | | |
| 27 | 81 | 65 | 81 | 73 | 64 | 28 |
| 28 | 97 | 74 | 97 | 89 | 83 | 53 |
| 33 | 95 | 85 | 68 | 82 | | |
| 35 | 39 | 30 | 39 | 23 | 24 | 14 |
| 39 | 46 | 28 | 12 | | | |
| 40 | 44 | 30 | 44 | | | |
| 41 | 95 | 89 | 87 | 76 | 54 | 18 |
| 43 | 98 | 86 | 95 | 83 | 70 | 11 |
| 44 | 99 | 97 | 91 | 81 | 71 | 21 |
| 47 | 59 | 47 | 55 | 6 | 18 | 34 |
| 48 | 98 | 88 | 88 | 63 | 33 | 0 |
| 49 | 92 | 84 | 78 | 72 | 51 | 12 |
| 50 | 93 | 59 | 58 | 42 | 29 | 0 |
| 51 | 80 | 48 | 35 | 0 | 0 | 0 |
| 53 | 96 | 85 | 94 | | 73 | |
| 56 | 93 | 72 | 82 | | 85 | |
| 57 | 100 | 97 | 89 | | 80 | |
| 58 | 83 | 71 | 82 | | 67 | |

1) Administration rate of compound No. 1 is 30 mg/kg.
2) Furosemide was not administered in case of Nos. 2 and 8.

The compounds of the invention which are not listed in Table 12 showed similar inhibition potencies.

Vasodepressor activity of the compounds of the invention was also measured with direct technique using an conscious monkey, where a monkey was administered a compound of the invention orally or intravenously (a solution in Tween 20). The test results are shown in Table 13.

TABLE 13

| Compound Example No. | Administration route | Dose (mg/kg) | Maximum reduced BP ($-\Delta$mmHg) |
|---|---|---|---|
| 43 | p.o. | 100 | 35 |
| | | 30 | 10 |

TABLE 13-continued

| Compound Example No. | Administration route | Dose (mg/kg) | Maximum reduced BP ($-\Delta$mmHg) |
|---|---|---|---|
| | | 10 | 5 |
| 43 | i.v. | 3 | — |
| | | 1 | 20 |
| | | 0.3 | 5 |
| 44 | i.v. | 3 | 20 |
| | | 1 | 8 |
| | | 0.3 | 5 |

The above test results show that the compounds of the present invention have renin inhibition potency both in vitro and in vivo.

The compounds of the invention are thus useful for the treatment of hypertension due to the renin inhibition when orally administered. However, other administration routes may be also effective.

As discussed previously, the compounds of the invention can be formulated into a pharmaceutical composition together with suitable carriers or excipients. When the compounds of the invention are used as a hypotensive agent, suitable dosage is 0.01-50 mg/kg/day in one to three divided does, preferably 0.05-10 mg/kg/day, when orally administered, and 1-5000 μg/kg/day, preferably 5-500 μg/kg/day, when parenterally administered.

What is claimed is:

1. A compound of formula (II):

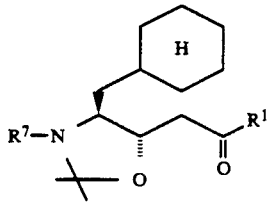

wherein, $R^1$ is dimethylamino, $C_1$–$C_{12}$ alkyl, $C_2$–$C_6$ alkenyl, $C_2$–$C_6$ alkynl, $C_3$–$C_{10}$ cycloalkyl, aryl, 2-thienyl, 3-thienyl, 2-furyl, 3-furyl, 2-pyrrolyl, 3-pyrrolyl, 2-imidazolyl, 1-pyrazolyl, 2-pyridyl, 3-pyridyl, 4-pyridyl, 2-pyrimidyl, 3-pyridazinyl, 2-pyrazinyl, 3-triazolyl, 2-thiazolyl, 4-thiazolyl, 5-tetrazolyl, 3-isothiazolyl, 2-pyrrolidinyl, 2-imidazolidinyl, 4-pyrazolidinyl, 4-piperidyl, 2-piperadinyl, 4-indolyl, 7-indolyl, 5-quinolyl, 8-quinolyl, 8-isoquinolyl, or morpholino; and $R^7$ is hydrogen or an amino protecting group.

* * * * *